(12) United States Patent
Simon et al.

(10) Patent No.: US 10,512,769 B2
(45) Date of Patent: Dec. 24, 2019

(54) NON-INVASIVE MAGNETIC OR ELECTRICAL NERVE STIMULATION TO TREAT OR PREVENT AUTISM SPECTRUM DISORDERS AND OTHER DISORDERS OF PSYCHOLOGICAL DEVELOPMENT

(71) Applicant: Electrocore, LLC, Basking Ridge, NJ (US)

(72) Inventors: Bruce J. Simon, Mountain Lakes, NJ (US); Joseph P. Errico, Warren, NJ (US); John T. Raffle, Austin, TX (US)

(73) Assignee: ElectroCore, Inc., Basking Ridge, NJ (US)

( * ) Notice: Subject to any disclaimer, the term of this patent is extended or adjusted under 35 U.S.C. 154(b) by 0 days.

(21) Appl. No.: 13/783,319

(22) Filed: Mar. 3, 2013

(65) Prior Publication Data

US 2013/0184792 A1    Jul. 18, 2013

Related U.S. Application Data

(63) Continuation-in-part of application No. 13/731,035, filed on Dec. 30, 2012, now Pat. No. 9,403,001, (Continued)

(51) Int. Cl.
*A61N 1/04* (2006.01)
*A61N 1/36* (2006.01)
(Continued)

(52) U.S. Cl.
CPC ......... *A61N 1/0408* (2013.01); *A61N 1/0456* (2013.01); *A61N 1/36014* (2013.01);
(Continued)

(58) Field of Classification Search
CPC ........................ A61N 1/36082; A61N 1/36025
See application file for complete search history.

(56) References Cited

U.S. PATENT DOCUMENTS 3,590,810 A * 7/1971 Kopecky .............. A61B 5/0408
204/403.06
4,196,737 A    4/1980 Bevilacqua
(Continued)

FOREIGN PATENT DOCUMENTS

EP    1967226    9/2008
EP    2777764    8/2015
(Continued)

OTHER PUBLICATIONS

Miyoshi, K. and Morimura, Y. "Clinical Manifestations of Neuropsychiatric Disorders," 2010, Neuropsychiatric Disorders, Springer, XIV, pp. 1-15.*
(Continued)

*Primary Examiner* — Michael W Kahelin
(74) *Attorney, Agent, or Firm* — Farber LLC

(57) ABSTRACT

Devices, systems and methods are disclosed for treating or preventing an autism spectrum disorder, a pervasive developmental disorder, or a disorder of psychological development. The methods comprise transmitting impulses of energy non-invasively to selected nerve fibers, particularly those in a vagus nerve. The nerve stimulation may be used as a behavior conditioning tool, by producing euphoria in an autistic individual. Vagus nerve stimulation is also used to modulate circulating serotonin levels in a pregnant woman so as to reduce the risk of having an autistic child; modulate the levels of growth factors within a child; promote balance of neuronal excitation/inhibition; modulate the activity of abnormal resting state neuronal networks; increase respiratory sinus arrhythmia; and avert episodes of motor stereotypies with the aid of forecasting methods.

18 Claims, 12 Drawing Sheets

Related U.S. Application Data which is a continuation-in-part of application No. 13/603,781, filed on Sep. 5, 2012, now Pat. No. 8,983,628, which is a continuation-in-part of application No. 13/222,087, filed on Aug. 31, 2011, now Pat. No. 9,174,066, which is a continuation-in-part of application No. 13/183,765, filed on Jul. 15, 2011, now Pat. No. 8,874,227, which is a continuation-in-part of application No. 13/183,721, filed on Jul. 15, 2011, now Pat. No. 8,676,324, which is a continuation-in-part of application No. 13/109,250, filed on May 17, 2011, now Pat. No. 8,676,330, which is a continuation-in-part of application No. 13/075,746, filed on Mar. 30, 2011, now Pat. No. 8,874,205, which is a continuation-in-part of application No. 13/024,727, filed on Feb. 10, 2011, now Pat. No. 9,089,719, which is a continuation-in-part of application No. 13/005,005, filed on Jan. 12, 2011, now Pat. No. 8,868,177, which is a continuation-in-part of application No. 12/964,050, filed on Dec. 9, 2010, now abandoned, which is a continuation-in-part of application No. 12/859,568, filed on Aug. 19, 2010, now Pat. No. 9,037,247, which is a continuation-in-part of application No. 12/408,131, filed on Mar. 20, 2009, now Pat. No. 8,812,112, and a continuation-in-part of application No. 12/612,177, filed on Nov. 4, 2009, now Pat. No. 8,041,428.

(60) Provisional application No. 61/488,208, filed on May 20, 2011, provisional application No. 61/487,439, filed on May 18, 2011, provisional application No. 61/471,405, filed on Apr. 4, 2011, provisional application No. 61/451,259, filed on Mar. 10, 2011, provisional application No. 61/415,469, filed on Nov. 19, 2010.

(51) Int. Cl.
  A61N 1/40 (2006.01)
  A61N 2/00 (2006.01)
  A61N 2/02 (2006.01)

(52) U.S. Cl.
  CPC .......... A61N 1/36025 (2013.01); A61N 1/40 (2013.01); A61N 2/006 (2013.01); A61N 2/02 (2013.01)

(56) References Cited

U.S. PATENT DOCUMENTS

| | | | |
|---|---|---|---|
| 4,989,605 A | 2/1991 | Rossen | |
| 5,109,847 A | 5/1992 | Liss et al. | |
| 5,458,141 A | 10/1995 | Neil | |
| 5,487,759 A | 1/1996 | Bastyr et al. | |
| 5,782,874 A | 7/1998 | Loos | |
| 5,899,922 A | 5/1999 | Loos | |
| 5,983,131 A | 11/1999 | Weaver et al. | |
| 6,341,236 B1 | 1/2002 | Osorio et al. | |
| 6,366,814 B1* | 4/2002 | Boveja ............ A61N 1/3605 | 607/45 |
| 6,463,327 B1 | 10/2002 | Lurie et al. | |
| 6,587,719 B1 | 7/2003 | Barrett et al. | |
| 6,610,713 B2 | 8/2003 | Tracey | |
| 6,631,297 B1 | 10/2003 | Mo | |
| 7,734,340 B2* | 6/2010 | De Ridder ........... A61N 1/0531 | 607/2 |
| 7,797,041 B2 | 9/2010 | Libbus et al. | |
| 2002/0099417 A1 | 7/2002 | Naritoku et al. | |
| 2002/0183237 A1 | 12/2002 | Puskas | |
| 2002/0183804 A1 | 12/2002 | Malaney et al. | |
| 2003/0212311 A1 | 11/2003 | Nova et al. | |
| 2004/0073271 A1 | 4/2004 | Harry et al. | |
| 2004/0243182 A1 | 12/2004 | Cohen et al. | |
| 2004/0249416 A1 | 12/2004 | Yun et al. | |
| 2005/0021092 A1 | 1/2005 | Yun et al. | |
| 2005/0065574 A1 | 3/2005 | Rezai | |
| 2005/0113630 A1 | 5/2005 | Fox et al. | |
| 2005/0137644 A1 | 6/2005 | Bojeva et al. | |
| 2005/0187590 A1* | 8/2005 | Boveja et al. ............ | 607/45 |
| 2005/0216062 A1 | 9/2005 | Herbst | |
| 2005/0267544 A1 | 12/2005 | Lee et al. | |
| 2006/0015153 A1* | 1/2006 | Gliner et al. ............ | 607/45 |
| 2006/0074284 A1 | 4/2006 | Juola et al. | |
| 2006/0074450 A1* | 4/2006 | Boveja et al. ............ | 607/2 |
| 2006/0100668 A1 | 5/2006 | Ben-David et al. | |
| 2006/0100671 A1 | 5/2006 | Ridder | |
| 2006/0173510 A1 | 8/2006 | Besio et al. | |
| 2006/0178703 A1 | 8/2006 | Huston et al. | |
| 2007/0027496 A1 | 2/2007 | Parnis et al. | |
| 2007/0038264 A1* | 2/2007 | Jaax et al. ............ | 607/45 |
| 2007/0106337 A1 | 5/2007 | Errico et al. | |
| 2007/0123952 A1 | 5/2007 | Strother et al. | |
| 2007/0142886 A1 | 6/2007 | Fischell et al. | |
| 2007/0150006 A1 | 6/2007 | Libbus et al. | |
| 2007/0156182 A1 | 7/2007 | Castel et al. | |
| 2007/0276449 A1 | 11/2007 | Gunter et al. | |
| 2008/0021512 A1 | 1/2008 | Knudson et al. | |
| 2008/0027513 A1 | 1/2008 | Carbunaru | |
| 2008/0045776 A1 | 2/2008 | Fischell et al. | |
| 2008/0051852 A1 | 2/2008 | Dietrich et al. | |
| 2008/0077192 A1 | 3/2008 | Harry et al. | |
| 2008/0114199 A1 | 5/2008 | Riehl et al. | |
| 2008/0132964 A1 | 6/2008 | Cohen et al. | |
| 2008/0177190 A1 | 7/2008 | Libbus et al. | |
| 2008/0208266 A1 | 8/2008 | Lesser et al. | |
| 2008/0306325 A1 | 12/2008 | Burnett et al. | |
| 2009/0112283 A1 | 4/2009 | Kriksunov et al. | |
| 2009/0132018 A1 | 5/2009 | DiUbaldi et al. | |
| 2009/0157149 A1 | 6/2009 | Wahlgren et al. | |
| 2009/0234417 A1 | 9/2009 | Pastena et al. | |
| 2009/0234419 A1 | 9/2009 | Maschino et al. | |
| 2009/0240297 A1 | 9/2009 | Shavit et al. | |
| 2009/0287035 A1 | 11/2009 | Dietrich et al. | |
| 2010/0030299 A1 | 2/2010 | Covalin | |
| 2010/0152794 A1 | 6/2010 | Radivojevic et al. | |
| 2010/0286553 A1 | 11/2010 | Feler et al. | |
| 2011/0046432 A1 | 2/2011 | Simon et al. | |
| 2011/0152967 A1 | 6/2011 | Simon et al. | |
| 2011/0213295 A1 | 9/2011 | Henley et al. | |
| 2011/0224749 A1 | 9/2011 | Ben-David et al. | |
| 2011/0230701 A1 | 9/2011 | Simon et al. | |
| 2012/0029591 A1* | 2/2012 | Simon ................ A61N 1/40 | 607/42 |
| 2012/0029601 A1 | 2/2012 | Simon et al. | |
| 2012/0283697 A1 | 11/2012 | Kim et al. | |
| 2012/0303080 A1 | 11/2012 | Ben-David et al. | |
| 2013/0006322 A1 | 1/2013 | Tai | |
| 2013/0060304 A1 | 3/2013 | LaTendresse et al. | |
| 2013/0204741 A1 | 8/2013 | Underwood | |
| 2013/0245486 A1 | 9/2013 | Simon et al. | |
| 2014/0005743 A1 | 1/2014 | Giuffrida et al. | |
| 2014/0222102 A1 | 8/2014 | Lemus et al. | |
| 2015/0165226 A1 | 6/2015 | Simon et al. | |
| 2015/0190637 A1 | 7/2015 | Simon et al. | |

FOREIGN PATENT DOCUMENTS

| | | |
|---|---|---|
| JP | 2009-125263 | 6/2009 |
| JP | 2009-233024 | 10/2009 |
| KR | 101242190 | 3/2013 |
| WO | WO 1993/01862 | 2/1993 |
| WO | WO 2005/007120 | 1/2005 |
| WO | WO 2007/092062 | 8/2007 |
| WO | WO 2008/042902 | 4/2008 |
| WO | WO 2007/058780 | 5/2008 |
| WO | WO 2009/021080 | 2/2009 |
| WO | WO2009/064641 | 5/2009 |

(56) References Cited

FOREIGN PATENT DOCUMENTS

| | | |
|---|---|---|
| WO | WO 2009/135693 | 11/2009 |
| WO | WO2012/121750 | 9/2012 |
| WO | WO2013066135 | 5/2013 |

OTHER PUBLICATIONS

Greicius et al., Functional connectivity in the resting brain: A network analysis of the default mode hypothesis, PNAS, Jan. 2003, vol. 100, No. 1, pp. 253-258.

Heneka et al., Locus ceruleus controls Alzheimer's disease pathology by modulating microglial functions through norepinephrine, PNAS, Mar. 2010, vol. 107, No. 13, pp. 6058-6063.

Lee et al., Clustering of Resting State Networks, PLoS One, Jul. 2012, vol. 7, Issue 7, pp. 1-12.

International Search Report and Written Opinion dated Mar. 26, 2008 in related PCT Application No. PCT/US2006/042752 filed Nov. 1, 2006 (7 pages).

International Search Report and Written Opinion dated Sep. 17, 2007 in related PCT Application No. PCT/US2006/042828 filed Nov. 2, 2006 (5 pages).

International Search Report and Written Opinion dated May 8, 2007 in related PCT Application No. PCT/US2006/042823 filed Nov. 2, 2006 (5 pages).

International Search Report and Written Opinion dated Dec. 22, 2011 in related PCT Application No. PCT/US2011/049844 filed Aug. 31, 2011 (9 pages).

International Search Report and Written Opinion dated Apr. 30, 2013 in related PCT Application No. PCT/US2013/023014 filed Jan. 24, 2013 (7 pages).

International Search Report and Written Opinion dated Dec. 11, 2013 in related PCT Application No. PCT/US2013/058079 filed Sep. 4, 2013 (8 pages).

International Search Report and Written Opinion dated Jan. 29, 2014 in related PCT Application No. PCT/US2013/068804 filed Nov. 6, 2013 (10 pages).

International Search Report and Written Opinion dated Aug. 25, 2015 in related Application No. PCT/US15/31847 filed May 20, 2015 (10 pages).

Europe Office Action dated Apr. 24, 2018 in related Application No. 15796247.3 filed May 20, 2015 (6 pages).

KR101242190 dated Mar. 25, 2013, Espacenet computer generated English translation (11 pages).

Europe Office Action dated Jul. 26, 2018 in related Application No. 11818591.7 filed Aug. 12, 2011 (8 pages).

Al-Kaisy et al., Poster, the American Academy of Pain Medicine. Analgeia of axial low back pain with novel spinal neuromodulation. Poster presentation #202 at the 2011 meeting of the American Academy of Pain Medicine, held in National Harbor, MD, 2011.

Albert et al., Deep brain stimulation, vagal nerve stimulation and transcranial stimulation: An overview of stimulation parameters and neurotransmitter release. Neuroscience and Biobehavioral Reviews 2009, 33, pp. 1042-1060.

Amin et al., Peripheral nerve stimulator for the treatment of supraorbital neuralgia: a retrospective case series. Cephalalgia 28, 2008, pp. 355-359.

Andrews, Neuromodulation. I. Techniques-deep brain stimulation, vagus nerve stimulation, and transcranial magnetic stimulation. Ann. N. Y. Acad. Sci. 993, 2003, pp. 1-13.

Asensio-Sampler et al., Peripheral neurostimulation in supraorbital neuralgia refractory to conventional therapy. Pain Pract 8, 2008, pp. 120-124.

Bennetto et al., Trigeminal neuralgia and its management. BMJ 334(7586), 2007, pp. 201-205.

Boinagrov et al., Strength-Duration Relationship for Extracellular Neural Stimulation: Numerical and Analytical Models. J Neurophysiol 104 2010, pp. 2236-2248.

Buchman, Nonlinear dynamics, complex systems, and the pathobiology of critical illness. Curr Opin Crit Care 10, 2004, pp. 378-382.

Cefaly Device, Food and Drug Administration Submission No. K122566, Transcutaneous Electrical Nerve Stimulator to Treat Headache, Dec. 2012 (15 pages).

Conder et al., Android Wireless Application Development, Second Edition. Upper Saddle River, NJ: Addison-Wesley, 2011.

Conway et al., Cerebral blood flow changes during vagus nerve stimulation for depression. Psychiatry Res. 146, 2006, pp. 179-184.

Cruccu et al., Unmyelinated trigeminal pathways as assessed by laser stimuli in humans. Brain 126, 2003, (Pt. 10), pp. 2246-2256.

Datta et al., Transcranial current stimulation focality using disc and ring electrode configurations: FEM analysis. J. Neural Eng. 5, 2008, pp. 163-174.

Delitto et al., Electrical stimulation of the quadriceps femoris in an elite weight lifter: a single subject experiment. Int J Sports Med 10, 1989, pp. 187-191.

Dimarzio, Android—A Programmer's Guide. New York: McGraw-Hill, 2008, pp. 1-319.

Evans et al., Intraoperative human vagus nerve compound action potentials. Acta Neurol Scand 110, 2004, pp. 232-238.

Falluco et al., The anatomical morphology of the supraorbital notch: clinical relevance to the surgical treatment of migraine headaches. Plast Reconstr Surg 130, 2012, pp. 1227-1233.

George et al., Noninvasive techniques for probing neurocircuitry and treating illness: vagus nerve stimulation (VNS), transcranial magnetic stimulation (TMS) and transcranial direct current stimulation (tDCS). Neuropsychopharmacology 35, 2010, pp. 301-316.

Gerardy et al., A pilot study on supra-orbital surface electrotherapy in migraine. Cephalalgia 29, 2009, 134 (poster session).

Grill et al., Stimulus waveforms for selective neural stimulation. IEEE Eng. Med. Biol. 14, 1995, pp. 375-385.

Groves et al., Vagal nerve stimulation: a review of its applications and potential mechanisms that mediate its clinical effects, Neurosci Biobehav Rev 29, 2005, pp. 493-500.

Hennings, Selective Electrical Stimulation of Peripheral Nerve Fibers: Accommodation Based Methods. Ph.D. Thesis, Center for Sensory-Motor Interaction, Aalborg University, Aalborg, Denmark, 2004.

Huston et al., Transcutaneous vagus nerve stimulation reduces serum high mobility group box 1 levels and improves survival in murine sepsis. Crit Care Med35, 2007, pp. 2762-2768.

Janis et al., Anatomy of the supratrochlear nerve: implications for the surgical treatment of migraine headaches. Plast Reconstr Surg 131, 2013, pp. 743-750.

Jasper et al., Implanted occipital nerve stimulators. Pain Physician 11, 2008, pp. 187-200.

Jenkins et al., Neurostimulation for primary headache disorders, part 1: pathophysiology and anatomy, history of neuromodulation in headache treatment, and review of peripheral neuromodulation in primary headaches. Headache 51, 2011, pp. 1254-1266.

Johnson et al., Analgesic effects of different pulse patterns of transcutaneous electrical nerve stimulation on cold-induced pain in normal subjects, Journal of Psychosomatic Research 35, 1991, pp. 313-321.

Jurgens et al., Pearls and pitfalls: neurostimulation in headache. Cephalalgia 33, 2013, pp. 512-525.

Keller et al., Electrodes for transcutaneous (surface) electrical stimulation. Journal of Automatic Control, University of Belgrade 18, 2008, pp. 35-45.

Kraus et al., Bold fMRI deactivation of limbic and temporal brain structures and mood enhancing effect by transcutaneous vagus nerve stimulation. J Neural Transm114, 2007, pp. 1485-1493.

Labiner et al., Vagus nerve stimulation therapy in depression and epilepsy: therapeutic parameter settings. Acta. Neurol. Scand. 115, 2007, pp. 23-33.

Lambru et al., Peripheral neurostimulation in primary headaches. Neurological Sciences 35, 2014, pp. 77-81.

Laufer et al., Effect of Burst Frequency and Duration of Kilohertz-Frequency Alternating Currents and of Low- Frequency Pulsed Currents on Strength of Contraction, Muscle Fatigue, and Perceived Discomfort. Physical Therapy 88, 2008, pp. 1167-1176.

Li et al., Patents, software and hardware for PID control: an overview and analysis of the current art. IEEE Control Systems Magazine, 26, 2006, pp. 42-54.

(56) References Cited

OTHER PUBLICATIONS

Magis et al., Advances and challenges in neurostimulation for headaches. Lancet Neurol 11, 2012, pp. 708-719.
Magis et al., Safety and patients' satisfaction of transcutaneous Supraorbital NeuroStimulation (tSNS) with the Cefaly® device in headache treatment: a survey of 2,313 headache sufferers in the general population, J Headache Pain, 1, 2013, pp. 1-8.
Mapstone, Vagus nerve stimulation: current concepts. Neurosurg Focus 25, 3rd edition, 2008, E9, pp. 1-4.
Moore, Electrical Stimulation for pain suppression: mathematical and physical models. Thesis, School of Engineering, Cornell University, 2007.
Narouze et al., Supraorbital nerve electric stimulation for the treatment of intractable chronic cluster headache: a case report. Headache 47, 2007, pp. 1100-1102.
Perlmutter et al., Deep brain stimulation. Annu. Rev. Neurosci 29, 2006, pp. 229-257.
Petrofsky et al., The transfer of current through skin and muscle during electrical stimulation with sine, square, Russian and interferential waveforms. Journal of Medical Engineering and Technology 33, 2009, pp. 170-181.
Piquet et al., Supraorbital transcutaneous neurostimulation has sedative effects in healthy subjects. BMC Neurol 11, 2011, pp. 1-7.
Rasskazoff et al., Neuromodulation for cephalgias. Surg Neurol Int., 2013, Suppl. 3; S136-S150.
Rattay, Analysis of models for extracellular fiber stimulation. IEEE Trans. Biomed. Eng. 36, 1989, pp. 676-682.
Rattay, The basic mechanism for the electrical stimulation of the nervous system. Neuroscience 89, 1999, pp. 335-346.
Reilly, Electrical models for neural excitation studies. Johns Hopkins APL Technical Digest 9, 1988, pp. 44-59.
Sawicki et al., Mathematical Modelling of Vagus Nerve Stimulation. Krawczyk, A. Electromagnetic Field, Health and Environment: Proceedings of EHE'07. Amsterdam, IOS Press, 2008, pp. 92-97.
Schoenen et al., Migraine prevention with a supraorbital transcutaneous stimulator: a randomized controlled trial. Neurology 80, 2013, pp. 697-704.
Schwarz et al., The Android Developer's Cookbook. Building Applications with the Android SDK, Second Edition. Upper Saddle River, NJ: Addison-Wesley, 2013.
Schwedt, Neurostimulation for Primary Headache Disorders. Curr Neurol Neurosci Rep 9, 2009, pp. 101-107.
Sein et al., Peripheral nerve stimulator placement with ultrasound guidance for the treatment of intractable postherpetic neuralgia: A case report., Poster 267, Proceedings of the 17th Annual. Meeting of the North American Neuromodulation Society. Las Vegas, Nevada, USA 20, 2013.
Silberstein, Migraine. Lancet 363, 2004, pp. 381-391.
Simopoulos et al., Implanted auriculotemporal nerve stimulator for the treatment of refractory chronic migraine. Headache 50, 2010, pp. 1064-1069.
Slavin et al., Trigeminal and occipital peripheral nerve stimulation for craniofacial pain: a single-institution experience and review of the literature. Neurosurg Focus 21, 2006, E6, pp. 1-5.
Spinner et al., Accuracy of ultrasound-guided superficial trigeminal nerve blocks using methylene blue in cadavers. Pain Med 13, 2012, pp. 1469-1473.
Swett et al., Electrical stimulation of peripheral nerve. Electrical Stimulation Research Techniques, Michael M. Patterson and Raymond P. Kesner, eds. Academic Press. New York, 1981, pp. 243-295.
Terry, Jr., Vagus nerve stimulation: a proven therapy for treatment of epilepsy strives to improve efficacy and expand applications. Conf Proc IEEE Eng Med Biol Soc., 2009, 4631-4634.
Vaisman et al., The treatment of medically intractable trigeminal autonomic cephalalgia with supraorbital/supratrochlear stimulation: a retrospective case series. Neuromodulation 15, 2012. pp. 374-380.
Vargas et al., The Face of Chronic Migraine: Epidemiology, Demographics, and Treatment Strategies. Neurol Clin 27, 2009, pp. 467-479.
Vuckovic et al., A comparative study of three techniques for diameter selective fiber activation in the vagal nerve: anodal block, depolarizing prepulses and slowly rising pulses. J. Neural Eng. 5, 2008, pp. 275-286.
Vuckovic et al., Different Pulse Shapes to Obtain Small Fiber Selective Activation by Anodal Blocking- A Simulation Study. IEEE Transactions on Biomedical Engineering 51, 2004, pp. 698-706.
Ward, Electrical Stimulation Using Kilohertz-Frequency Alternating Current. Physical Therapy 89, 2009, pp. 181-190.
Ward et al., Russian Electrical Stimulation: The Early Experiments. Physical Therapy 82, 2002, pp. 1019-1030.
White et al., Electroanalgesia: Its Role in Acute and Chronic Pain Management. Anesth Analg 92, 2001, pp. 505-513.
Wolfson, Android Developer Tools Essentials. Sebastopol, California: O'Reilly Media Inc., 2013.

\* cited by examiner

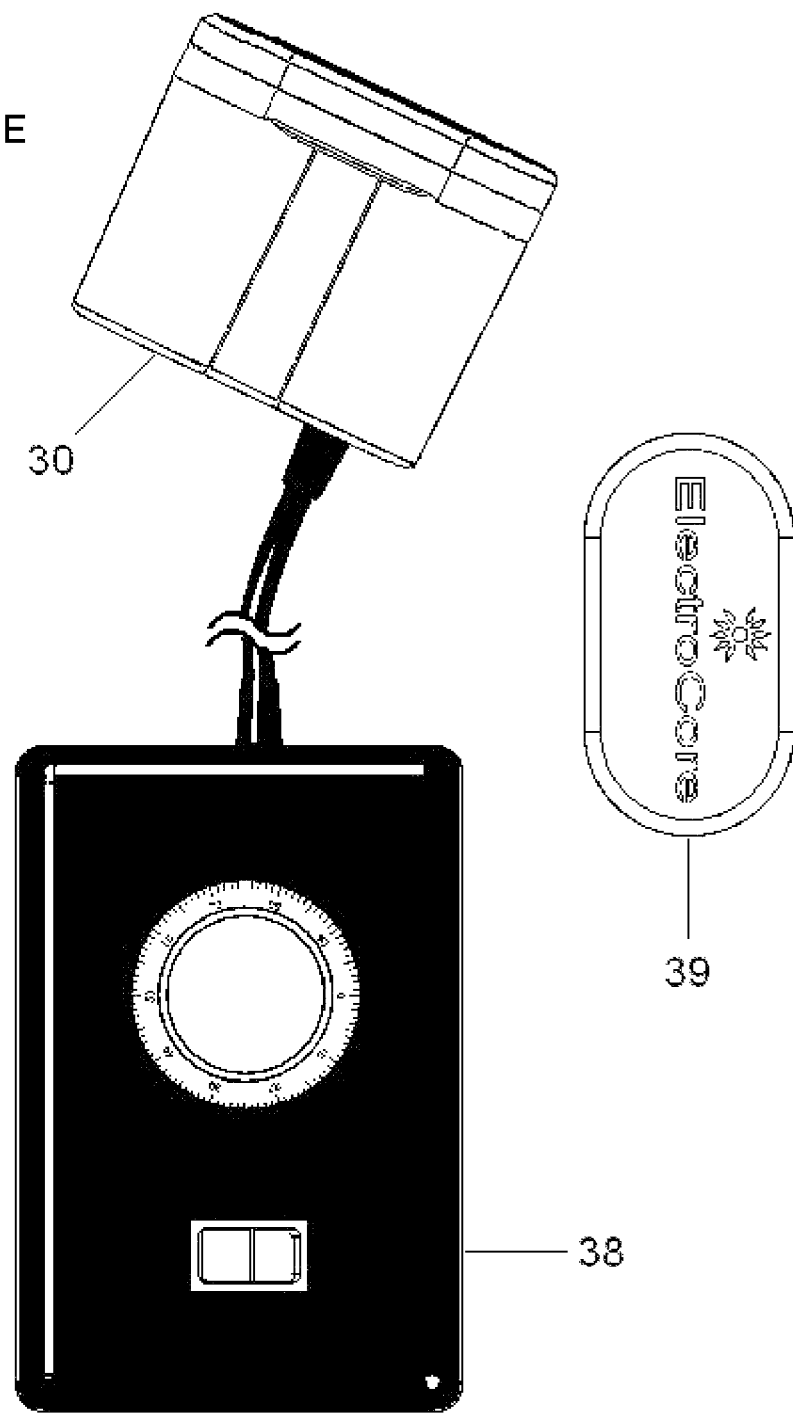

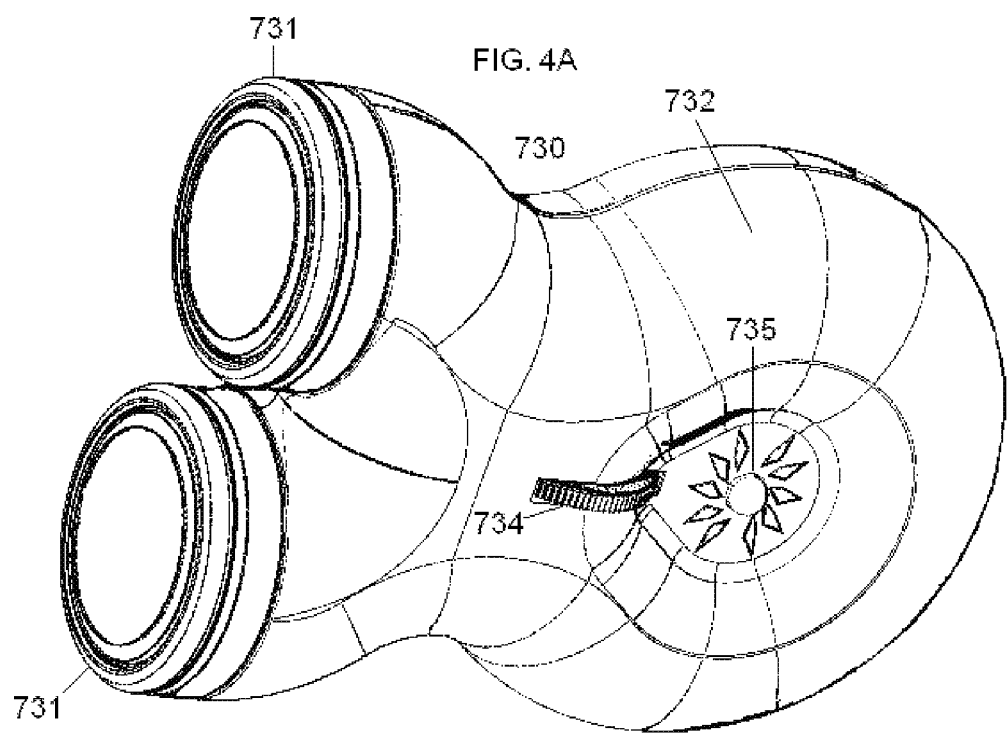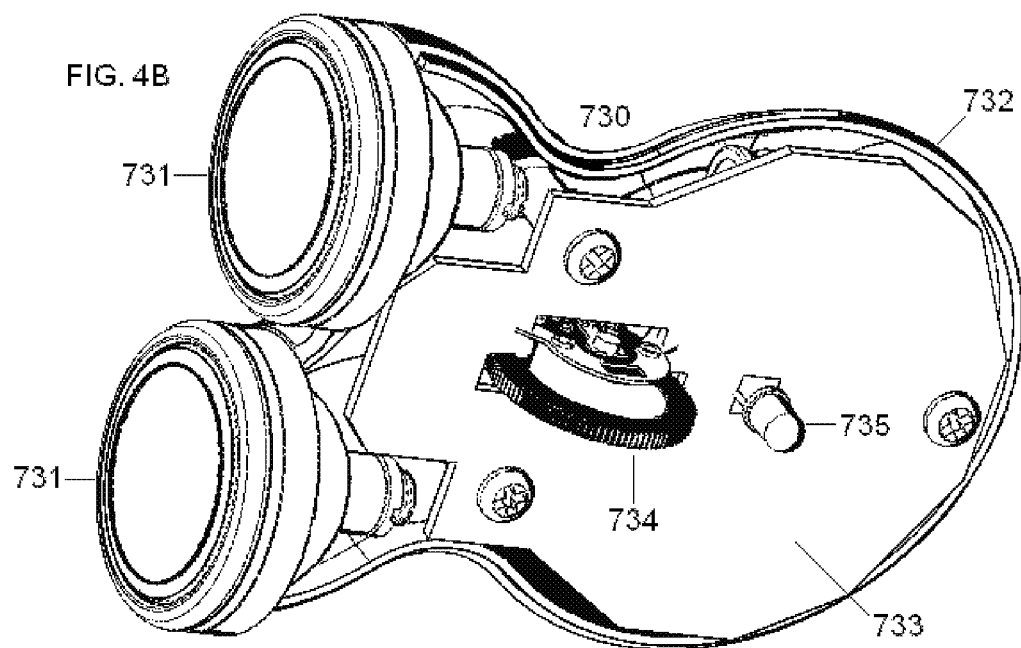

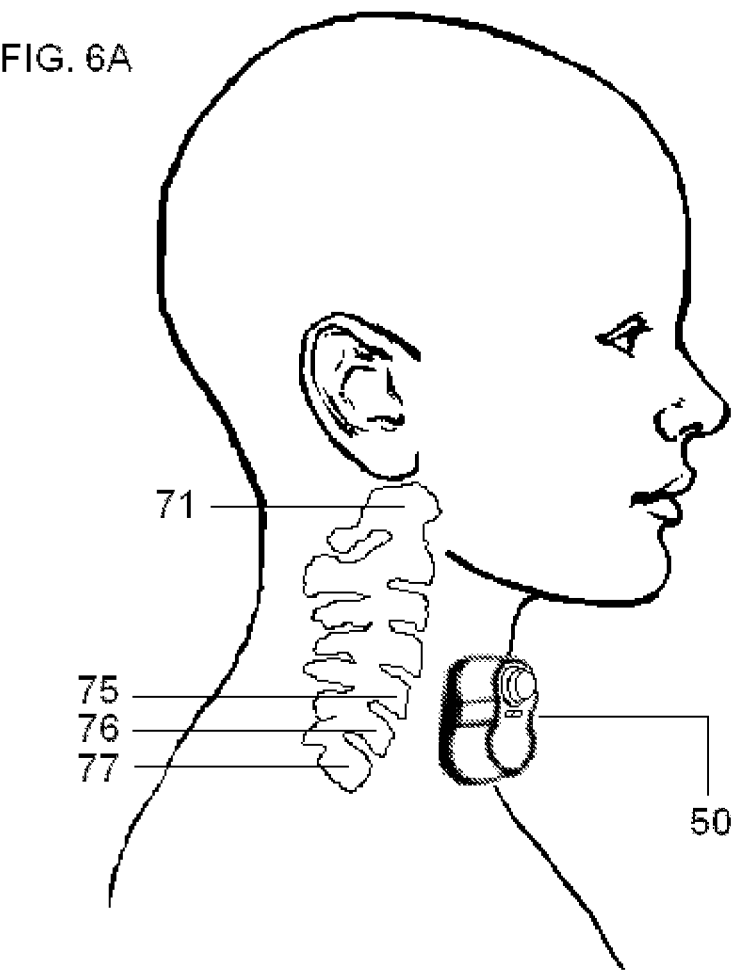

NON-INVASIVE MAGNETIC OR ELECTRICAL NERVE STIMULATION TO TREAT OR PREVENT AUTISM SPECTRUM DISORDERS AND OTHER DISORDERS OF PSYCHOLOGICAL DEVELOPMENT

CROSS REFERENCE TO RELATED APPLICATIONS

This application is a continuation-in-part of U.S. patent application Ser. No. 13/731,035 filed Dec. 30, 2012 now U.S. Pat. No. 9,403,001 issued Aug. 2, 2016, which application is a continuation-in-part of U.S. patent application Ser. No. 13/603,781 filed Sep. 5, 2012 now U.S. Pat. No. 8,983,628 issued Mar. 17, 2015, which is a continuation-in-part of U.S. patent application Ser. No. 13/222,087 filed Aug. 31, 2011 now U.S. Pat. No. 9,174,006 issued Nov. 3, 2015, which is a continuation-in-part of U.S. patent application Ser. No. 13/183,765 filed Jul. 15, 2011 now U.S. Pat. No. 8,874,227 issued Oct. 28, 2014, which claims the benefit of priority of U.S. Provisional Patent Application No. 61/488,208 filed May 20, 2011 and is a continuation-in-part of U.S. patent application Ser. No. 13/183,721 filed Jul. 15, 2011 now U.S. Pat. No. 8,676,324 filed Mar. 18, 2014, which claims the benefit of priority of U.S. Provisional Patent Application No. 61/487,439 filed May 18, 2011 and is a continuation-in-part of U.S. patent application Ser. No. 13/109,250 filed May 17, 2011 now U.S. Pat. No. 8,676,330 issued Mar. 18, 2014, which claims the benefit of priority of U.S. Provisional Patent Application No. 61/471,405 filed Apr. 4, 2011 and is a continuation-in-part of U.S. patent application Ser. No. 13/075,746 filed Mar. 30, 2011 now U.S. Pat. No. 8,874,205 issued Oct. 28, 2015, which claims the benefit of priority of U.S. provisional patent application 61/451,259 filed Mar. 10, 2011 and is a continuation-in-part of U.S. patent application Ser. No. 13/005,005 filed Jan. 12, 2011 now U.S. Pat. No. 8,868,177 issued Oct. 21, 2014, which is a continuation-in-part of U.S. patent application Ser. No. 12/964,050 filed Dec. 9, 2010, which claims the benefit of priority of U.S. Provisional Patent Application No. 61/415,469 filed Nov. 19, 2010 and is a continuation-in-part of U.S. patent application Ser. No. 12/859,568 filed Aug. 19, 2010 now U.S. Pat. No. 9,037,247 issued May 19, 2015, which is a continuation-in-part application of U.S. patent application Ser. No. 12/612,177 filed Nov. 4, 2009, now U.S. Pat. No. 8,041,428 issued Oct. 18, 2011, which is a continuation-in-part of U.S. patent application Ser. No. 12/408,131 filed Mar. 20, 2009 now U.S. Pat. No. 8,812,112 issued Aug. 19, 2014, the entire disclosures of which are hereby incorporated by reference.

This application is also related to commonly assigned co-pending U.S. patent application Ser. No. 13/357,010 filed Jan. 24, 2012, U.S. patent application Ser. No. 13/357,025 filed Jan. 24, 2012, U.S. patent application Ser. No. 13/655,716 filed Jan. 24, 2012, U.S. Provisional Patent Application No. 61/585,668 filed Jan. 12, 2012 and U.S. patent application Ser. No. 13/671,859 filed Nov. 8, 2012 the complete disclosures of which are incorporated herein by reference for all purposes.

BACKGROUND OF THE INVENTION

The field of the present invention relates to the delivery of energy impulses (and/or fields) to bodily tissues for therapeutic purposes. The invention relates more specifically to devices and methods for treating conditions associated with autism and other disorders of psychological development. The energy impulses (and/or fields) that are used to treat those conditions comprise electrical and/or electromagnetic energy, delivered non-invasively to the patient.

The use of electrical stimulation for treatment of medical conditions is well known. For example, electrical stimulation of the brain with implanted electrodes (deep brain stimulation) has been approved for use in the treatment of various conditions, including pain and movement disorders such as essential tremor and Parkinson's disease [Joel S. PERLMUTTER and Jonathan W. Mink. Deep brain stimulation. Annu. Rev. Neurosci 29 (2006):229-257].

Another application of electrical stimulation of nerves is the treatment of radiating pain in the lower extremities by stimulating the sacral nerve roots at the bottom of the spinal cord [Paul F. WHITE, Shitong Li and Jen W. Chiu. Electroanalgesia: Its Role in Acute and Chronic Pain Management. Anesth Analg 92 (2001):505-513; U.S. Pat. No. 6,871,099, entitled Fully implantable microstimulator for spinal cord stimulation as a therapy for chronic pain, to WHITEHURST, et al].

The form of electrical stimulation that is most relevant to the present invention is vagus nerve stimulation (VNS, also known as vagal nerve stimulation). It was developed initially for the treatment of partial onset epilepsy and was subsequently developed for the treatment of depression and other disorders. The left vagus nerve is ordinarily stimulated at a location within the neck by first surgically implanting an electrode there and then connecting the electrode to an electrical stimulator [U.S. Pat. No. 4,702,254 entitled Neurocybernetic prosthesis, to ZABARA; U.S. Pat. No. 6,341,236 entitled Vagal nerve stimulation techniques for treatment of epileptic seizures, to OSORIO et al; U.S. Pat. No. 5,299,569 entitled Treatment of neuropsychiatric disorders by nerve stimulation, to WERNICKE et al; G. C. ALBERT, C. M. Cook, F. S. Prato, A. W. Thomas. Deep brain stimulation, vagal nerve stimulation and transcranial stimulation: An overview of stimulation parameters and neurotransmitter release. Neuroscience and Biobehavioral Reviews 33 (2009):1042-1060; GROVES D A, Brown V J. Vagal nerve stimulation: a review of its applications and potential mechanisms that mediate its clinical effects. Neurosci Biobehav Rev 29 (2005):493-500; Reese TERRY, Jr. Vagus nerve stimulation: a proven therapy for treatment of epilepsy strives to improve efficacy and expand applications. Conf Proc IEEE Eng Med Biol Soc. 2009; 2009:4631-4634; Timothy B. MAPSTONE. Vagus nerve stimulation: current concepts. Neurosurg Focus 25 (3, 2008):E9, pp. 1-4; ANDREWS, R. J. Neuromodulation. I. Techniques-deep brain stimulation, vagus nerve stimulation, and transcranial magnetic stimulation. Ann. N.Y. Acad. Sci. 993 (2003):1-13; LABINER, D. M., Ahern, G. L. Vagus nerve stimulation therapy in depression and epilepsy: therapeutic parameter settings. Acta. Neurol. Scand. 115 (2007):23-33].

Many such therapeutic applications of electrical stimulation involve the surgical implantation of electrodes within a patient. In contrast, devices used for the procedures that are disclosed here do not involve surgery. Instead, the present devices and methods stimulate nerves by transmitting energy to nerves and tissue non-invasively. A medical procedure is defined as being non-invasive when no break in the skin (or other surface of the body, such as a wound bed) is created through use of the method, and when there is no contact with an internal body cavity beyond a body orifice (e.g, beyond the mouth or beyond the external auditory meatus of the ear). Such non-invasive procedures are distinguished from invasive procedures (including minimally invasive procedures) in that the invasive procedures insert a substance or device into or through the skin (or other surface of the body, such as a wound bed) or into an internal body cavity beyond a body orifice.

For example, transcutaneous electrical stimulation of a nerve is non-invasive because it involves attaching electrodes to the skin, or otherwise stimulating at or beyond the surface of the skin or using a form-fitting conductive garment, without breaking the skin [Thierry KELLER and Andreas Kuhn. Electrodes for transcutaneous (surface) electrical stimulation. Journal of Automatic Control, University of Belgrade 18(2, 2008):35-45; Mark R. PRAUSNITZ. The effects of electric current applied to skin: A review for transdermal drug delivery. Advanced Drug Delivery Reviews 18 (1996) 395-425]. In contrast, percutaneous electrical stimulation of a nerve is minimally invasive because it involves the introduction of an electrode under the skin, via needle-puncture of the skin.

Another form of non-invasive electrical stimulation is magnetic stimulation. It involves the induction, by a time-varying magnetic field, of electrical fields and current within tissue, in accordance with Faraday's law of induction. Magnetic stimulation is non-invasive because the magnetic field is produced by passing a time-varying current through a coil positioned outside the body. An electric field is induced at a distance, causing electric current to flow within electrically conducting bodily tissue. The electrical circuits for magnetic stimulators are generally complex and expensive and use a high current impulse generator that may produce discharge currents of 5,000 amps or more, which is passed through the stimulator coil to produce a magnetic pulse. The principles of electrical nerve stimulation using a magnetic stimulator, along with descriptions of medical applications of magnetic stimulation, are reviewed in: Chris HOVEY and Reza Jalinous, The Guide to Magnetic Stimulation, The Magstim Company Ltd, Spring Gardens, Whitland, Carmarthenshire, SA34 0HR, United Kingdom, 2006. In contrast, the magnetic stimulators that are disclosed here are relatively simpler devices that use considerably smaller currents within the stimulator coils. Accordingly, they are intended to satisfy the need for simple-to-use and less expensive non-invasive magnetic stimulation devices, for use in treating autism and other developmental conditions, as well as use in treating other conditions.

Potential advantages of such non-invasive medical methods and devices relative to comparable invasive procedures are as follows. The patient may be more psychologically prepared to experience a procedure that is non-invasive and may therefore be more cooperative, resulting in a better outcome. Non-invasive procedures may avoid damage of biological tissues, such as that due to bleeding, infection, skin or internal organ injury, blood vessel injury, and vein or lung blood clotting. Non-invasive procedures are generally painless and may be performed without the dangers and costs of surgery. They are ordinarily performed even without the need for local anesthesia. Less training may be required for use of non-invasive procedures by medical professionals. In view of the reduced risk ordinarily associated with non-invasive procedures, some such procedures may be suitable for use by the patient or family members at home or by first-responders at home or at a workplace. Furthermore, the cost of non-invasive procedures may be significantly reduced relative to comparable invasive procedures.

In the present invention, noninvasive electrical and/or magnetic stimulation of a vagus nerve is used to treat or manage pervasive developmental disorders, such as autism, which are neuro-developmental disorders characterized by problems involving a child's socialization, communication, and repetitive or other unusual behavior. Such disorders are listed in entry F84 in the International Statistical Classification of Diseases and Related Health Problems, 10th Revision (ICD-10). They include childhood autism (F84.0), atypical autism (F84.1), Rett syndrome (F84.2), other childhood disintegrative disorder (F84.3), overactive disorder associated with mental retardation and stereotyped movements (F84.4), Asperger syndrome (F84.5), other pervasive developmental disorders (F84.8), and unspecified pervasive developmental disorder (F84.9) [World Health Organization. International Statistical Classification of Diseases and Related Health Problems 10th Revision (ICD-10) Geneva, Switzerland: The WHO (English edition: 10th revision, 2008), entry F84].

A similar classification of pervasive developmental disorders appears in The Diagnostic and Statistical Manual of Mental Disorders, 4th edition (DSM-IV)—Autistic Disorder (299.00), Pervasive Developmental Disorder, Not Otherwise Specified (299.80), Asperger's Disorder (299.80), Rett's Disorder (299.80), and Childhood Disintegrative Disorder (299.10) [American Psychiatric Association. Criteria for Autism in: Diagnostic and Statistical Manual of Mental disorders (4th ed., text rev.; DSM-IV). Washington, D.C.: The Association (2000), code 299]. However, the 5th edition of The Diagnostic and Statistical Manual of Mental Disorders (DSM-V), which will be forthcoming in 2013, will combine several of these disorders (including Asperger syndrome and Pervasive Developmental Disorder Not Otherwise Specified—abbreviated as PDD-NOS) into a single entity, namely, autism spectrum disorders (ASD).

According to the proposed DSM-V revised criteria for autism spectrum disorders, an autistic spectrum individual must meet the following A, B, C and D criteria. (A). Persistent deficits in social communication and social interaction across contexts, not accounted by general developmental delays and manifest by all three of the following: (1) Deficits in social-emotional reciprocity . . . ; (2) Deficits in nonverbal communicative behaviors used for social interaction . . . ; (3) Deficits in developing and maintaining relationships appropriate to developmental level, beyond those with caregivers. (B). Restricted, repetitive patterns of behavior, interests or activities as manifested by at least two of the following. (1) Stereotyped or repetitive speech, motor movements, or use of objects . . . ; (2) Excessive adherence to routines, ritualized patterns of verbal or nonverbal behavior, or excessive resistance to change . . . ; (3) Highly restricted, fixated interests that are abnormal in intensity or focus . . . ; (4) Hyper- or hypo-reactivity to sensory input or unusual interests in sensory aspects of environment . . . ; (C). Symptoms must be present in early childhood . . . ; (D). Symptoms together limit and impair everyday functioning.

Although ASD is already in widespread use as a term, the reconceptualization of ASD in DSM-V is controversial for at least the following reason. Currently, the most common diagnosis among autistic spectrum individuals is PDD-NOS, which is sometimes referred to as atypical "mild autism". Similarly, Asperger syndrome is sometimes referred to as a "higher functioning autism". Some individuals who are presently diagnosed with Asperger syndrome, as well as PDD-NOS individuals without repetitive or ritualized behaviors, may not be considered autistic under the revised DSM-V criteria. This may affect the availability of services in the United States that they currently obtain (e.g., special schooling, health care, and behavioral therapies). [HAPPE, F. Criteria, categories, and continua: Autism and related disorders in DSM-5. Journal of the American Academy of Child & Adolescent Psychiatry 50 (2011): 540-542;

McPARTLAND, J. C., Reichow, B., and Volkmar, F. R. Sensitivity and specificity of proposed DSM-5 diagnostic criteria for autism spectrum disorder. Journal of the American Academy of Child & Adolescent Psychiatry 51 (2012): 368-383; WORLEY, A. and Matson, J. L. Comparing symptoms of autism spectrum disorders using the current DSM-IV-TR diagnostic criteria and the proposed DSM-V diagnostic criteria. Research in Autism Spectrum Disorders 6 (2012):965-970; FRAZIER, T. W., Youngstrom, E. A., Speer, L., Embacher, R., Law, P., Constantino, J . . . . Eng, C. Validation of proposed DSM-5 criteria for autism spectrum disorder. Journal of the American Academy of Child and Adolescent Psychiatry 51 (2012):28-40].

The diagnosis of a particular pervasive developmental disorder, such as autism, is made after extended observation and interaction with a child. Best practices include an initial routine developmental surveillance of the child, in which a professional looks for certain age-specific developmental milestones. If the surveillance reveals clinical clues of possible autism, it is followed by the diagnosis and evaluation. A screening test for autism in young children, often the Checklist for Autism in Toddlers (CHAT), is then conducted. If the CHAT screening suggests possible autism, further assessment is performed. The diagnosis of autism (or other developmental disorder) often does not occur until the child reaches the age of 3 or 4 [Pauline A. FILIPEK, Pasquale J. Accardo, Grace T. Baranek, et al. The screening and diagnosis of autistic spectrum disorders. J Autism Dev Disord. 29(6, 1999):439-484; FILIPEK P A, Accardo P J, Ashwal S, et al. Practice parameter: screening and diagnosis of autism: report of the Quality Standards Subcommittee of the American Academy of Neurology and the Child Neurology Society. Neurology 55(4, 2000):468-479; New York State Department of Health (NYSDH). Clinical practice guideline: Quick Reference Guide for Parents and Professionals. Autism/Pervasive developmental disorders assessment and intervention for young children (age 0-3 years). Publication No. 4216, Albany, N.Y. 1999, pp. 1-97; BAIRD, T Charman, A Cox, S Baron-Cohen, J Swettenham, S Wheelwright, and A Drew. Screening and surveillance for autism and pervasive developmental disorders. Arch Dis Child 84(6, 2001): 468-475; KLIN, A., Saulnier, C. D., Tsatsanis, K. D., & Volkmar, F. R. (2005) Clinical evaluation in autism spectrum disorders: Psychological assessment within a transdisciplinary framework. In F. R. Volkmar, R. Paul, A. Klin, & D. Cohen (Eds.), Handbook of autism and pervasive developmental disorders: 3rd Edition, John Wiley & Sons, pp. 772-798; Sara Jane WEBB and Emily J. H. Jones. Early Identification of Autism—Early Characteristics, Onset of Symptoms, and Diagnostic Stability Infants & Young Children 22(2, 2009):100-118].

Several testing instruments are commonly used to assess the likelihood of autism, including The Autism Behavior Checklist (ABC), Autism Diagnostic Interview-Revised (ADI-R), The Childhood Autism Rating Scale (CARS), The Pre-Linguistic Autism Diagnostic Observation Schedule (PL-ADOS), and The Autism Diagnostic Observation Schedule and its generic version (ADOS-G) [SCHOPLER E, Reichler R J, DeVellis R F, Daly K. Toward objective classification of childhood autism: Childhood Autism Rating Scale (CARS). J Autism Dev Disord 10(1, 1980):91-103; RELLINI E, Tortolani D, Trillo S, Carbone S, Montecchi F. Childhood Autism Rating Scale (CARS) and Autism Behavior Checklist (ABC) correspondence and conflicts with DSM-IV criteria in diagnosis of autism. J Autism Dev Disord 34(6, 2004):703-708. LORD C, Rutter M, Goode S, Heemsbergen J, Jordan H, Mawhood L, Schopler E. Autism diagnostic observation schedule: a standardized observation of communicative and social behavior. J Autism Dev Disord 19(2, 1989):185-212; LORD C, Rutter M, Le Couteur A. Autism Diagnostic Interview-Revised: a revised version of a diagnostic interview for caregivers of individuals with possible pervasive developmental disorders. J Autism Dev Disord 24(5, 1994):659-685; DILAVORE P C, Lord C, Rutter M. The pre-linguistic autism diagnostic observation schedule. J Autism Dev Disord 25(4, 1995):355-379; LORD C, Risi S, Lambrecht L, Cook E H Jr, Leventhal B L, DiLavore P C, Pickles A, Rutter M. The autism diagnostic observation schedule-generic: a standard measure of social and communication deficits associated with the spectrum of autism. J Autism Dev Disord 30(3, 2000):205-223].

An individual might be diagnosed as having Asperger syndrome under the ICD-10 criteria, and autism spectrum disorder under the DSM-V criteria, or Asperger syndrome under DSM-IV criteria. In that regard, a diagnostic complication is that under the hierarchical rules of DSM-IV, a dual diagnosis of autism spectrum disorder with attention-deficit hyperactivity disorder (ADHD) is not possible, because signs for the ADHD must not be due to the course of a pervasive developmental disorder. In contrast, under ICD-10, a dual Asperger and ADHD diagnosis is possible, provided that the Asperger syndrome individual also exhibits traits of ADHD such as hyperactivity, impulsiveness, short attention span, and executive function deficits. This illustrates the diagnostic confusion that is inherent in the use of different disease classifications (ICD versus DSM), which is significant because different diagnoses may require different treatments [Michael FITZGERALD and Aiden Corvin. Diagnosis and differential diagnosis of Asperger syndrome. Advances in Psychiatric Treatment 7(2001): 310-318]. The confusion might be avoided if diagnosis could be made on the basis of laboratory tests rather than solely on the basis of behavioral criteria, but biomarkers that would be useful for that purpose are not yet available [WALSH P, Elsabbagh M, Bolton P, Singh I. In search of biomarkers for autism: scientific, social and ethical challenges. Nat Rev Neurosci 12(10, 2011):603-612; VEENSTRA-VanderWeele J, Blakely R D. Networking in autism: leveraging genetic, biomarker and model system findings in the search for new treatments. Neuropsychopharmacology 37(1, 2012):196-212; RATAJCZAK H V. Theoretical aspects of autism: biomarkers—a review. J Immunotoxicol 8(1, 2011):80-94; HENDREN R L, Bertoglio K, Ashwood P, Sharp F. Mechanistic biomarkers for autism treatment. Med Hypotheses 73(6, 2009): 950-954; SKJELDAL O H, Sponheim E, Ganes T, Jellum E, Bakke S. Childhood autism: the need for physical investigations. Brain Dev 20(4, 1998):227-233].

Before the 1990s, the prevalence of autism spectrum disorders was thought to be no more than 5 per 10,000 individuals. Many recent epidemiological studies tend to conclude that prevalence of autistic disorder falls between 10 and 20 per 10,000. Some reports find that the incidence is 60 per 10,000 or more. Boys are affected with ASDs more frequently than are girls by a ratio of 4.3:1. The incidence of all pervasive developmental disorders has been estimated to be between 30 and 116 per 10,000, with a prevalence of 2.5 per 10,000 for Asperger syndrome and 15 per 10,000 for PDD-NOS. The data do not show significant prevalence differences according to geographic region, ethnic/cultural factors, or socioeconomic factors. The increasing prevalence is most likely due to the broadening concept of autistic spectrum disorder over the years and to a greater awareness of these disorders among professionals and the public at large. The lifetime per capita incremental cost of autism has been estimated to be $3.2 million, with adult care and lost productivity being the largest components of costs [ELSABBAGH M, Divan G, Koh Y J, et al. Global prevalence of autism and other pervasive developmental disorders. Autism Res 5(3, 2012):160-179; NEWSCHAFFER C J, Croen L A, Daniels J, et al. The epidemiology of autism spectrum disorders. Annu Rev Public Health 28 (2007):235-258; RUTTER M. Incidence of autism spectrum disorders: changes over time and their meaning. Acta Paediatr 94(1, 2005):2-15; GANZ M L. The lifetime distribution of the incremental societal costs of autism. Arch Pediatr Adolesc Med 161(4, 2007):343-349].

Many environmental risk factors have been investigated as potential causes of ASD, including certain foods, infectious disease, heavy metals, solvents, diesel exhaust, PCBs, phthalates and phenols used in plastic products, pesticides, brominated flame retardants, alcohol, smoking, illicit drugs, vaccines, and prenatal stress. However, only a few such as rubella exposure have been shown to be significant causative agents [NEWSCHAFFER C J, Croen L A, Daniels J, et al. The epidemiology of autism spectrum disorders. Annu Rev Public Health 28 (2007):235-258].

Autism has a strong genetic basis, as evidenced by the study of twins and other relatives of individuals with ASD. However, the genetics of autism is complex. The number of gene mutations found to carry risk for ASD is now well into the hundreds, with no single locus accounting for more than 1% of cases. Furthermore, these mutations may be associated not only with ASD, but also with disorders such as epilepsy, mental retardation, and schizophrenia. Some such mutations are particularly associated with genetic disorders in which autism is common, such as Joubert Syndrome, Smith-Lemli-Opitz syndrome, Tuberous Sclerosis and Fragile X. Practical use of these genetic markers may have to wait until it is better understood how expression of the genes occurs at different times during the embryological development of the brain [FREITAG C M. The genetics of autistic disorders and its clinical relevance: a review of the literature. Mol Psychiatry 12(1, 2007):2-22; KUMAR R A, Christian S L. Genetics of autism spectrum disorders. Curr Neurol Neurosci Rep 9(3, 2009):188-197; GESCHWIND D H. Genetics of autism spectrum disorders. Trends Cogn Sci 15(9, 2011):409-416; STATE M W, Šestan N. Neuroscience. The emerging biology of autism spectrum disorders. Science 337(6100, 2012):1301-1303].

In addition to the above-mentioned genetic syndromes, such as Fragile X and tuberous sclerosis, autism is frequently comorbid with mood disorders, phobias, obsessive compulsive disorders, anxiety disorders, and psychosis. As noted above, it is also frequently comorbid with attention deficit hyperactivity disorder, provided that ICD-10 criteria are used [MATSON J L, Nebel-Schwalm M S. Comorbid psychopathology with autism spectrum disorder in children: an overview. Res Dev Disabil 28(4, 2007):341-352]. Intellectual disability or mental handicap (previously known as mental retardation) may occur in as many as 75% of autistic children, although special testing methods may be necessary to distinguish autism from intellectual disability [OSTERLING J A, Dawson G, Munson J A. Early recognition of 1-year-old infants with autism spectrum disorder versus mental retardation. Dev Psychopathol 14(2, 2002):239-251]. Many other medical symptoms or disorders are commonly reported in children with autism, including epilepsy, immune system dysregulation, gastrointestinal symptoms, motor impairment, sensory dysfunction, feeding difficulties/eating disorders, and sleep disorders [NEWSCHAFFER C J, Croen L A, Daniels J, et al. The epidemiology of autism spectrum disorders. Annu Rev Public Health 28 (2007):235-258; TUCHMAN R, Cuccaro M, Alessandri M. Autism and epilepsy: historical perspective. Brain Dev 32 (2010):709-718; TUCHMAN R, Rapin I. Epilepsy in autism. Lancet Neurol 1(6, 2002):352-358; BOLTON P F, Carcani-Rathwell I, Hutton J, Goode S, Howlin P, Rutter M. Epilepsy in autism: features and correlates. Br J Psychiatry 198(4, 2011):289-294; STAFSTROM C E, Hagerman P J, Pessah I N. Pathophysiology of Epilepsy in Autism Spectrum Disorders. In: Noebels J L, Avoli M, Rogawski M A, Olsen R W, Delgado-Escueta A V, editors. Jasper's Basic Mechanisms of the Epilepsies. 4th edition. Bethesda (MD): National Center for Biotechnology Information (US), 2012, pp. 1-19; PARDO C A, Vargas D L, Zimmerman A W. Immunity, neuroglia and neuroinflammation in autism. Int Rev Psychiatry 17(6, 2005):485-495; ERICKSON C A, Stigler K A, Corkins M R, Posey D J, Fitzgerald J F, McDougle C J. Gastrointestinal factors in autistic disorder: a critical review. J Autism Dev Disord 35(6, 2005):713-727; MING X, Brimacombe M, Wagner G C. Prevalence of motor impairment in autism spectrum disorders. Brain Dev 29(9, 2007):565-570; ROGERS S J, Ozonoff S. Annotation: what do we know about sensory dysfunction in autism? A critical review of the empirical evidence. J Child Psychol Psychiatry 46(12, 2005):1255-1268].

In the remainder of this background section, current methods for treating or managing pervasive developmental disorders, such as autism, are described. Methods that have been used to treat autism and related developmental disorders were reviewed extensively and recently in the Comparative Effectiveness Review No. 26 of the Agency for Healthcare Research and Quality of the U.S. Department of Health and Human Services. That review also analyzes the efficacy of the treatment methods [WARREN Z, Veenstra-VanderWeele J, Stone W, et al. Therapies for Children With Autism Spectrum Disorders. Comparative Effectiveness Review No. 26. (Prepared by the Vanderbilt Evidence-based Practice Center under Contract No. 290-2007-10065-I.) AHRQ Publication No. 11-EHC029-EF. Rockville, Md.: Agency for Healthcare Research and Quality. April 2011, 908 pp]. In that publication, treatment methods are organized into four groups: Behavioral Interventions, Educational Interventions, Medical Interventions (including dietary methods), Allied Health Interventions (e.g., language, sensory, and auditory interventions), and Complementary and Alternative Medicine (CAM) Interventions.

Behavioral interventions were the first to show that it is in fact possible to treat autistic children. The interventions may take place at home, at school, and/or at a clinic and may involve a trained professional as well as the parents of the autistic child, often for several years of 40 hours per week of one-on-one sessions. Many such programs make use of applied behavior analysis in which there is (1) a request for the child to perform an action, (2) a response on the part of the child, and (3) a consequence which can range from strong positive reinforcement to strong negative reinforcement. As ordinarily practiced nowadays, only positive reinforcement is given (typically, verbal praise, a favored snack food, or time with a preferred toy). The design of the program includes selecting the behaviors or skills that are to be achieved. Thus, the child may be taught social, motor, and verbal behavior and cognitive skills, and can also be taught not to engage in undesirable behaviors. The program is preferably individualized to the needs of each child. Individual requests to the child are selected after having first dissected an overall behavior that is desired into component parts, and the training may consist of reinforcing the individual components, then reinforcing the chain of components so as to achieve the desired overall behavior.

An intervention program will also design the way that reinforcement is applied at different stages of conditioning the child (e.g., eventually eliminating reinforcement after the child has fully acquired the desired behavior). Skills may also be exercised in a more natural setting than the controlled home or clinical environment in which it was first taught. The UCLA/Lovaas-based interventions are perhaps the best known such interventions, but other behavioral intervention programs include special social skills interventions, play/interaction-based interventions, the Early Start Denver Model (ESDM), less intensive interventions focusing on providing parent training, cognitive behavioral therapy, neurofeedback, and sleep interventions. Whatever intervention method is used, it is advised to begin therapy at as early an age as practical, possibly age 2 or 3 [ROGERS S J, Vismara L A. Evidence-based comprehensive treatments for early autism. J Clin Child Adolesc Psychol 37(1, 2008): 8-38; VISMARA L A, Rogers S J. Behavioral treatments in autism spectrum disorder: what do we know? Annu Rev Clin Psychol 6 (2010):447-468]

Educational interventions are also often based on applied behavior analysis and are sometimes intended for special-needs instruction in elementary schools. Ten such educational programs are reviewed in a publication of the National Research Council. Those programs are as follows: Children's Unit, Denver Community Based Approach, Developmental Intervention Model, Douglass, Individualized Support Program, LEAP, Pivotal response training, TEACCH, UCLA Young Autism Project, and Walden [Catherine LORD and James P. McGee, Eds., and National Research Council Committee on Educational Interventions for Children with Autism. Educating children with autism. Washington, D.C.: National Academy Press (2001)].

There are a few medical interventions for ASD, but no medications are currently available to treat its core symptoms. However, there is preliminary evidence that the diuretic bumetanide might be helpful [LEMONNIER E, Degrez C, Phelep M, Tyzio R, Josse F, Grandgeorge M, Hadjikhani N, Ben-Ari Y. A randomised controlled trial of bumetanide in the treatment of autism in children. Transl Psychiatry 2 (2012):e202, pp. 1-8]. Also, evidence favors the use of medications to address challenging behaviors of autistic children, using risperidone and aripiprazole (for tantrums, disruptive behavior, aggression towards others, self-injury, quickly changing moods, and irritability) [LESKOVEC T J, Rowles B M, Findling R L. Pharmacological treatment options for autism spectrum disorders in children and adolescents. Hary Rev Psychiatry 16(2, 2008): 97-112; McPHEETERS M L, Warren Z, Sathe N, Bruzek J L, Krishnaswami S, Jerome R N, Veenstra-Vanderweele J. A systematic review of medical treatments for children with autism spectrum disorders. Pediatrics 127(5, 2011):e1312-e1321]. Drugs are also used to treat co-morbid conditions of autism, such as epilepsy.

A large number of dietary supplement, special diet, language, sensory, and auditory interventions, as well as complementary and alternative medicine interventions have been used to treat the symptoms of autism. According to ROSSIGNOL, melatonin, antioxidants, acetylcholinesterase inhibitors, naltrexone, and music therapy appear to show benefits. LEVY recommended the use of melatonin but found that there was insufficient evidence to recommend the use of other such therapies [ROSSIGNOL D A. Novel and emerging treatments for autism spectrum disorders: a systematic review. Ann Clin Psychiatry 21(4, 2009):213-236; LEVY S E, Hyman S L. Complementary and alternative medicine treatments for children with autism spectrum disorders. Child Adolesc Psychiatr Clin N Am 17(4, 2008): 803-820].

When acupuncture is used to treat autistic individuals, the points of stimulation are LI4 on the hand where the thumb and first finger meet, PC6 on the palm-side of the forearm above the crease of the wrist, ST36 on the calf near the knee, and SP6 on the calf near the ankle. The putative mechanism of such acupuncture treatment is via changes in levels of arginine-vasopressin and oxytocin [ZHANG R, Jia M X, Zhang J S, Xu X J, Shou X J, Zhang X T, Li L, Li N, Han S P, Han J S. Transcutaneous electrical acupoint stimulation in children with autism and its impact on plasma levels of arginine-vasopressin and oxytocin: a prospective single-blinded controlled study. Res Dev Disabil 33(4, 2012):1136-1146]. Apparently, no acupuncture point in the vicinity of a vagus nerve is used.

Magnetic stimulation has been used in an attempt to treat, diagnose, or characterize potentially autistic individuals. However, those magnetic stimulation methods, transcranial magnetic stimulation and transcranial direct current stimulation, have been applied only to the brain of those individuals, and not to a peripheral nerve, as disclosed here [DEMIRTAS-Tatlidede A, Vahabzadeh-Hagh A M, Pascual-Leone A. Can noninvasive brain stimulation enhance cognition in neuropsychiatric disorders? Neuropharmacology 64 (2013):566-578; Xuejun KONG. Clinical significance of functional MRI guided transcranial magnetic stimulation for autism. N A J Med Sci. 2(2, 2009):64-66; OBERMAN L, Eldaief M, Fecteau S, Ifert-Miller F, Tormos J M, Pascual-Leone A. Abnormal modulation of corticospinal excitability in adults with Asperger's syndrome. Eur J Neurosci 36(6, 2012):2782-2788; SOKHADZE E, Baruth J, Tasman A, Mansoor M, Ramaswamy R, Sears L, Mathai G, El-Baz A, Casanova M F. Low-frequency repetitive transcranial magnetic stimulation (rTMS) affects event-related potential measures of novelty processing in autism. Appl Psychophysiol Biofeedback 35(2, 2010):147-161; SOKHADZE E M, El-Baz A, Baruth J, Mathai G, Sears L, Casanova M F. Effects of low frequency repetitive transcranial magnetic stimulation (rTMS) on gamma frequency oscillations and event-related potentials during processing of illusory figures in autism. J Autism Dev Disord 39(4, 2009):619-634; STAMOULIS C, Oberman L M, Praeg E, Bashir S, Pascual-Leone A. Single pulse TMS-induced modulations of resting brain neurodynamics encoded in EEG phase. Brain Topogr 24(2, 2011):105-113].

Invasive vagus nerve stimulation (VNS) is currently approved for the treatment of epilepsy in children older than 12 years, including children with autism spectrum disorders (also including Asperger syndrome children) and other pervasive developmental disorders such as Rett's syndrome. VNS may also be used investigationally in younger children as well, also including children with autism spectrum disorders [James W. WHELESS. Vagus nerve stimulation in pediatrics: determining appropriate candidates. Advanced Studies in Medicine 5(5B, 2005): S474-S476; BLOUNT J P, Tubbs R S, Kankirawatana P, Kiel S, Knowlton R, Grabb P A, Bebin M Vagus nerve stimulation in children less than 5 years old. Child's Nervous System 22(9, 2006):1167-1169]. Approximately 30% of epileptic children also have autism spectrum disorders, and approximately 30% of individuals with autism spectrum disorders have epilepsy [TUCHMAN R, Cuccaro M, Alessandri M. Autism and epilepsy: historical perspective. Brain Dev 32 (2010):709-718; TUCHMAN R, Rapin I. Epilepsy in autism. Lancet Neurol 1(6, 2002):

352-358; BOLTON P F, Carcani-Rathwell I, Hutton J, Goode S, Howlin P, Rutter M. Epilepsy in autism: features and correlates. Br J Psychiatry 198(4, 2011):289-294]. Consequently, some data exist not only as to whether VNS is useful for the treatment of epilepsy in autistic children, but also whether the VNS affects the childrens' austic symptoms. However, the parameters of the electrical stimulation were chosen to treat the epilepsy, and not the autism, so the data concerning changes of autistic symptoms are essentially accounts of the side effects of the epilepsy treatment.

DANIELSSON et al. used invasive VNS to treat eight autistic children, four of which had also been diagnosed as having attention deficit hyperactivity disorder. They reported that two years of VNS treatment did not decrease the frequency of epileptic seizures in the children and had no positive cognitive effects. In one child, negative changes of general functioning were observed, but in three children, minor improvements in general functioning were measured through use of standard tests (Autistic Behavior Checklist; Autism Diagnostic Observation Schedule, Children's Global Assessment Scale, and Clinical Global Impressions-Improvement scale). The number of children was small, and there was no control group, so it is not clear from these data whether any changes in austistic symptoms were due to the VNS treatment, to other diverse treatments that the children were also receiving, or to the natural progression of autistic symptoms [DANIELSSON S, Viggedal G, Gillberg C, Olsson I. Lack of effects of vagus nerve stimulation on drug-resistant epilepsy in eight pediatric patients with autism spectrum disorders: a prospective 2-year follow-up study. Epilepsy Behav 12(2, 2008):298-304].

MURPHY et al. performed invasive VNS with six patients with medically refractory epilepsy secondary to hypothalamic hamartomas, four of which had severe autistic behaviors. Seizure control was found in three of the patients, and improved behavior was observed in all four of the autistic children [MURPHY J V, Wheless J W, Schmoll C M. Left vagal nerve stimulation in six patients with hypothalamic hamartomas. Pediatr Neurol 23(2, 2000):167-168]. In patent application US20050187590, entitled Method and system for providing therapy for autism by providing electrical pulses to the vagus nerve(s), to BOJEVA et al, the publication by MURPHY was noted, and it was further disclosed that an implanted vagus nerve stimulator could be used to treat autism. However, unlike the present disclosure, their application did not disclose any step that is unique to the treatment of autism or to a related neuro-developmental disorder.

LEVY et al examined a registry of patients with implanted VNS stimulators and found that after treatment, patients with autism have epileptic symptoms that are similar to those of patients without autism. Among quality of life indicators only the one, improved mood after 12 months of treatment, was found to be better in autistic patients as compared with non-autistic patients [LEVY M L, Levy K M, Hoff D, Amar A P, Park M S, Conklin J M, Baird L, Apuzzo M L. Vagus nerve stimulation therapy in patients with autism spectrum disorder and intractable epilepsy: results from the vagus nerve stimulation therapy patient outcome registry. J Neurosurg Pediatr 5(6, 2010):595-602].

PARK investigated 59 epileptic patients with autism, nineteen of whom had Lennox-Gastaut syndrome. He found that more than half of the patients had a reduction in seizure frequency after 12 months and that the quality of life generally improved in the patients, with some 76% of them experiencing an improved alertness [PARK Y D. The effects of vagus nerve stimulation therapy on patients with intractable seizures and either Landau-Kleffner syndrome or autism. Epilepsy Behav 4(3, 2003):286-290].

WARWICK et al described the case of one epileptic patient with Asperger syndrome. After six months of treatment using invasive VNS, the number of seizures and the duration of seizures were reduced. Furthermore, using modified Yale-Brown Obsessive Compulsive Scale and quality of life scales, after six months of VNS treatment, the patient was found to have improved Abnormal Nonverbal, Social Interaction, and Emotional Scores, as well as improved mood and memory [WARWICK T C, Griffith J, Reyes B, Legesse B, Evans M. Effects of vagus nerve stimulation in a patient with temporal lobe epilepsy and Asperger syndrome: case report and review of the literature. Epilepsy Behav 10(2, 2007):344-347].

WILFONG described the use of VNS treatment for epilepsy in seven Rett syndrome patients. The investigators found that after 12 months of treatment, there was a decrease in seizure frequency in six of them, that the patients were more alert, but there were not changes in mood or communication abilities [WILFONG A A, Schultz R J. Vagus nerve stimulation for treatment of epilepsy in Rett syndrome. Dev Med Child Neurol 48(8, 2006):683-686].

The publications that were cited above suggest that invasive vagus nerve stimulation may be useful in the treatment of autistic children who have epilepsy. WALKER et al performed animal experiments that addressed the issue of whether there are common neural pathways relating to seizures and autism-like behaviors, which may explain why epilepsy is found in approximately 30% of autistic children. They made lesions in rats that specifically target forebrain and cerebellar neurons, in order to create behaviors in rats that are similar to behavioral deficits seen in epilepsy and autism. They conclude that epilepsy and autism may have common neural pathways, and when that is the case, VNS might be used as a treatment for the autism [WALKER B R, Diefenbach K S, Parikh T N. Inhibition within the nucleus tractus solitarius (NTS) ameliorates environmental exploration deficits due to cerebellum lesions in an animal model for autism. Behav Brain Res 176(1, 2007):109-120].

However, there is no suggestion in these publications that vagus nerve stimulation could be used to treat autistic children who do not have epilepsy, and in fact, the parameters of the nerve stimulation (pulse width, frequency, etc.) were chosen to treat the epilepsy, without regard to the symptoms of autism. Furthermore, there is no suggestion that the vagus nerve stimulation could be applied noninvasively. Similarly, the use of deep brain stimulation to treat autism has only been mentioned in connection with the primary treatment of another disorder such as epilepsy or movement disorders [Anya McLAREN. Deep brain stimulation: a potential therapy for epilepsy and movement disturbances in autism spectrum disorders? Journal on Developmental Disabilities 13 (3, 2007): 167-186]. However, something similar to deep brain stimulation for the treatment of autism was disclosed in U.S. Pat. No. 7,623,927, entitled Modulation of the brain to affect psychiatric disorders, to REZAI, and in application US20090326605, entitled Treatment of language, behavior and social disorders, to MORRELL.

The psychology literature also refers to vagus nerve stimulation in young children who are at risk for developmental difficulties, but that stimulation consists of massage, kangaroo care, and similar tactile interventions, not electrical stimulation of the vagus nerve. The rationale for such tactile intervention is that the vagus nerve in the at-risk children has low tone, as evidenced primarily by unusually low respiratory sinus arrhythmia. The tactile stimulation is thought to increase the vagal tone, resulting in more normal attentiveness, facial expressions and vocalizations [FIELD T, Diego M. Vagal activity, early growth and emotional development. Infant Behav Dev 31(3, 2008):361-373].

PORGES and colleagues expand on that concept, arguing that developmental disorders are caused by, or are associated with, abnormalities in the autonomic nervous system generally, because the autonomic nervous system modulates affective experience, emotional expression, facial gestures, vocal communication and contingent social behavior. As an example, PORGES points to rocking and swinging of an autistic child, in which the position of the head is changed relative to the position of the heart. This will stimulate the baroreceptors and thereby engage autonomic heartrate/blood pressure feedback control loops. According to PORGES, this suggests that the frequently observed rocking and swinging behaviors in autistic individuals may reflect a naturally occurring biobehavioral strategy to stimulate and regulate a vagal system that is not efficiently functioning. However, despite his recognition of the potential of vagus nerve stimulation to help epileptic individuals with autistic-like behavior as described above in the publication by MURPHY, PORGES did not develop vagus nerve stimulation interventions to treat autonomic dysfunction in autistic children. Instead, he disclosed a behavioral intervention that uses acoustic stimulation to improve social behavior, and tested the approach with children diagnosed with autism. With that intervention, computer altered acoustic stimulation was presented in 45-min sessions, during which attempts were made to maintain the child in a calm behavioral state [PORGES S W. The polyvagal theory: phylogenetic substrates of a social nervous system. Int J Psychophysiol 42(2, 2001):123-46; PORGES S W. The Polyvagal Theory: phylogenetic contributions to social behavior. Physiol Behav 79(3, 2003):503-513; PORGES S W, Furman S A. The Early Development of the Autonomic Nervous System Provides a Neural Platform for Social Behavior: A Polyvagal Perspective. Infant Child Dev 20(1, 2011):106-118].

In the present disclosure, applicants teach the use of noninvasive vagus nerve stimulation (VNS) to treat autism spectrum disorders and other pervasive developmental disorders, irrespective of whether the patient also experiences epileptic seizures. One problem that may arise in performing the VNS noninvasively is that it requires the cooperation of the patient when applying the stimulator for an extended period of time to the patient's neck. For children with behavioral problems, the invention teaches that restraining the problematic child to apply the stimulator may not be necessary, provided that the child is initially taught or trained to actually want the stimulator to be applied. Thus, in one aspect of the invention, the child is initially stimulated noninvasively in such a way as to feel euphoric and therefore will not resist subsequent applications of the stimulator. Methods for creating a euphoric mental state using VNS were disclosed in a commonly assigned, co-pending application Ser. No. 13/024,727, entitled Non-invasive methods and devices for inducing euphoria in a patient and their therapeutic application, to SIMON et al, which is hereby incorporated by reference.

Having achieved the willingness of the child to undergo the noninvasive VNS through the induction of euphoria, the euphoric stimulation might then be provided only when the child performs a desirable task, thereby using the VNS as a conditioning stimulus for behavioral therapy. In another aspect of the invention, disclosed waveforms of the VNS are selected to inhibit or activate particular neural networks of the brain that are associated with autistic behavior and that become abnormal during the course of a child's development. That is to say, the invention is intended to provide a much-needed medical intervention. The methods may also be applicable to psychological developmental disorders generally. Such disorders include disorders of psychological development other than pervasive developmental disorders (i.e., ICD 10 classifications F80-F89 other than F84) and Intellectual Developmental Disorders (i.e. ICD 10 classifications F70-F79) which, like autism, have a strong genetic basis for causing developmental cognitive abnormalities (e.g., Down syndrome, Klinefelter's syndrome, Fragile X syndrome, neurofibromatosis, congenital hypothyroidism, Williams syndrome, phenylketonuria and Prader-Willi syndrome). The methods may also be applicable to some behavioral and emotional disorders with onset usually occurring in childhood and adolescence (ICD 10 classifications F90-F98), which are commonly comorbid with autism. This would include disturbances of activity and attention (attention deficit disorder, F90.0).

SUMMARY OF THE INVENTION

The present invention involves devices and methods for the treatment or prevention of autism and other neurodevelopmental disorders. The patient may be a pregnant mother who is at risk for having an autistic child, an individual who is potentially autistic, or an individual who is actually diagnosed as being autistic. For such individuals, the treatment may be as a newborn, an infant, a toddler, a young child, an older child, a young adult, or an adult. In certain aspects of the invention, a device or system comprises an energy source of magnetic and/or electrical energy that is transmitted non-invasively to, or in close proximity to, a selected nerve of the patient to temporarily stimulate and/or modulate the signals in the selected nerve. In preferred embodiments of the invention, the selected nerve is a vagus nerve in the patient's neck.

In one aspect of the invention, an autistic child is stimulated noninvasively in such a way as to feel euphoric so that he or she will not resist subsequent applications of the stimulator. Methods for creating a euphoric mental state using vagus nerve stimulation were disclosed in a commonly assigned, co-pending application Ser. No. 13/024,727, entitled Non-invasive methods and devices for inducing euphoria in a patient and their therapeutic application, to SIMON et al. Having achieved the willingness of the child to undergo the noninvasive VNS through the induction of euphoria, the euphoric stimulation may then be provided as a conditioning stimulus for treatment of the autism. The disclosure describes treating impairment in the use of nonverbal behaviors and in improving development of peer relationships. It also describes methods for promoting the sharing of interests with others, increased social reciprocity, the use of spoken or nonverbal language, the non-repetition of words, engagement in conversation, novelty in pretend play, interest in a new subject, flexibility in routines or the loss of ritual behavior, the loss of repetitive or stereotyped behavior, and the loss of preoccupation with particular objects.

In another aspect of the invention, vagus nerve stimulation is performed on a pregnant woman, preferably during the first trimester, in order to prevent abnormal neurodevelopment of the fetus. The intervention modulates the mother's circulating levels of serotonin by stimulating enterochromaffin cells in the gut. This intervention is intended especially for women who are taking serotonin reuptake inhibitors or who are using cocaine. It may also be useful for women who may pass on an autism gene variant to her child, the gene variant being one that results in an overactive serotonin transporter.

In another aspect of the invention, vagus nerve stimulation of a newborn or infant is used to increase the activity of raphe nuclei to produce more serotonin in the newborn's brain, especially among those newborns who have demonstrable hyper-serotonemia due to an overactive serotonin transporter.

In another aspect of the invention, vagus nerve stimulation is used as a prophylaxis or countermeasure against unusual patterns of a child's growth, especially during the first and second years, through modulation of the activity of growth factors, comprising BDNF, FGF-2, FGF-7, FGF-22, HGF/SF, IGF-1, VEGF, and serotonin.

In another aspect of the invention, vagus nerve stimulation is used to promote neuronal excitation-inhibition balance, particularly by increasing the number of inhibitory GABAergic synapses throughout the developing brain of a newborn or young child who is at risk for becoming autistic. The parameters of the vagus nerve stimulation may be selected or adjusted in such a way as to prevent or reduce abnormal high frequency components in the EEG of the child, which is a measure of excitation-inhibition imbalance.

For children and adults who are autistic, vagus nerve stimulation may also be used to promote neuronal excitation-inhibition balance, by acting in opposition to glutamate-mediated excitation of nerve tissue, through the inhibitory effects of GABA, and/or serotonin, and/or norepinephrine that are released from the periaqueductal gray, raphe nucei, and locus coeruleus, respectively.

The brain contains several neural networks that can be identified by brain imaging, which are known as resting state networks. Examples of such networks include the default mode network (DMN), the ventral attention network (VAN), and networks that include the anterior insula (AI) and anterior cingulate cortex (ACC). The locus ceruleus is thought to project to all of the resting state networks. Vagus stimulation methods of the present invention increase norepinephrine levels in a resting state network, wherein a particular resting state network may be preferentially stimulated via the locus ceruleus, by using a vagus nerve stimulation waveform that entrains to the signature EEG pattern of that network. Depending on the distribution of adrenergic receptor subtypes within the resting state network, the vagus nerve stimulation may deactivate or activate the network. Deactivation of a resting state network may also be accomplished by activating another resting state network, which causes deactivation of other networks.

Resting state networks may be abnormal in individuals with autism, which may be identified using fMRI measurement. The measurements may point to abnormalities in particular networks such as the default mode network and networks related attention, salience, and the processing of sensory information. They may also point to abnormalities in the switching or toggling between networks. The present invention modulates the activity such resting state networks via the locus ceruleus, by training an abnormal resting state network to become more normal. For example, the training increases the activity of a resting state network that is abnormally inactive. It may also attempt to change the signature EEG pattern of a network, by slowly changing the frequency content of the stimulation & EEG pattern of the network to which the stimulator is entrained. The training may be accompanied by other modalities of sensory stimulation, such as sound, successive pictures of faces, etc.

For some patients, the stimulation may be performed for 30 minutes, and the treatment is initially performed several times a week for 12 weeks or longer to observe its effect on behavior, EEG, respiratory sinus arrhythmia, or other biomarkers. If the patient is a pregnant woman, the treatment is preferably performed during the first trimester. For children or adults who are potentially or actually autistic, the treatment may in some cases be essentially continuous. For patients experiencing intermittent behavioral symptoms, the treatment may be performed only when the patient is symptomatic. However, it is understood that parameters of the stimulation protocol may be varied in response to heterogeneity in the symptoms of patients. Different stimulation parameters may also be selected as the course of the patient's neurodevelopment changes. In preferred embodiments, the disclosed methods and devices do not produce clinically significant side effects, such as agitation or anxiety, or changes in heart rate or blood pressure. It is understood that the stimulation may also make use of an implanted vagus nerve stimulator, particularly in children who are otherwise being treated for epilepsy (but generally using stimulation parameters to treat the autism rather than the epilepsy), or in non-epileptic children who cannot adapt to the use of a noninvasive stimulator.

In one embodiment, the method of treatment includes positioning the coil of a magnetic stimulator non-invasively on or above a patient's neck and applying a magnetically-induced electrical impulse non-invasively to the target region within the neck to stimulate or otherwise modulate selected nerve fibers. In another embodiment, surface electrodes are used to apply electrical impulses non-invasively to the target region within the neck to likewise stimulate or otherwise modulate selected nerve fibers. Preferably, the target region is adjacent to, or in close proximity with, the carotid sheath that contains a vagus nerve.

The non-invasive magnetic stimulator device is used to modulate electrical activity of a vagus nerve, without actually introducing a magnetic field into the patient. The preferred stimulator comprises two toroidal windings that lie side-by-side within separate stimulator heads, wherein the toroidal windings are separated by electrically insulating material. Each toroid is in continuous contact with an electrically conducting medium that extends from the patient's skin to the toroid. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described below, shaping an elongated electrical field of effect.

In another embodiment of the invention, the stimulator comprises a source of electrical power and two or more remote electrodes that are configured to stimulate a deep nerve. The stimulator may comprise two electrodes that lie side-by-side within a hand-held enclosure, wherein the electrodes are separated by electrically insulating material. Each electrode is in continuous contact with an electrically conducting medium that extends from the interface element of the stimulator to the electrode. The interface element also contacts the patient's skin when the device is in operation.

Current passing through an electrode may be about 0 to 40 mA, with voltage across the electrodes of about 0 to 30 volts. The current is passed through the electrodes in bursts of pulses. There may be 1 to 20 pulses per burst, preferably five pulses. Each pulse within a burst has a duration of about 20 to 1000 microseconds, preferably 200 microseconds. A burst followed by a silent inter-burst interval repeats at 1 to 5000 bursts per second (bps, similar to Hz), preferably at 15-50 bps, and even more preferably at 25 bps. The preferred shape of each pulse is a full sinusoidal wave.

A source of power supplies a pulse of electric charge to the electrodes or magnetic stimulator coil, such that the electrodes or magnetic stimulator produce an electric current and/or an electric field within the patient. The electrical or magnetic stimulator is configured to induce a peak pulse voltage sufficient to produce an electric field in the vicinity of a nerve such as a vagus nerve, to cause the nerve to depolarize and reach a threshold for action potential propagation. By way of example, the threshold electric field for stimulation of the nerve may be about 8 V/m at 1000 Hz. For example, the device may produce an electric field within the patient of about 10 to 600 V/m (preferably less than 100 V/m) and an electrical field gradient of greater than 2 V/m/mm. Electric fields that are produced at the vagus nerve are generally sufficient to excite all myelinated A and B fibers, but not necessarily the unmyelinated C fibers. However, by using a reduced amplitude of stimulation, excitation of A-delta and B fibers may also be avoided.

The preferred stimulator shapes an elongated electric field of effect that can be oriented parallel to a long nerve, such as a vagus. By selecting a suitable waveform to stimulate the nerve, along with suitable parameters such as current, voltage, pulse width, pulses per burst, inter-burst interval, etc., the stimulator produces a correspondingly selective physiological response in an individual patient. Such a suitable waveform and parameters are simultaneously selected to avoid substantially stimulating nerves and tissue other than the target nerve, particularly avoiding the stimulation of nerves in the skin that produce pain.

Treating or averting autism or other neurodevelopmental disorders may be implemented within the context of control theory. A controller comprising, for example, one of the disclosed vagus nerve stimulators, a PID, and a feedforward model, provides input to the patient via stimulation of one or both of the patient's vagus nerves. In one embodiment, the vagus nerve stimulation is varied as a function of the phase of respiration, in order to train the patient's autonomic nervous system so as to increase his abnormally low respirator sinus arrhythmia. Feedforward models may be black box models, particularly models that make use of support vector machines. Data for training and exercising the models are from noninvasive physiological and/or environmental signals obtained from sensors located on or about the patient. A disclosed model predicts the imminent onset of motor stereotypies (e.g., hand flapping, or rocking and swinging), which may be averted through use of vagus nerve stimulation. If the symptoms are in progress, the vagus nerve stimulation may be used to terminate them.

The novel systems, devices and methods for treating autism and other neuro-developmental disorders are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

INCORPORATION BY REFERENCE

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 3E illustrates the magnetic stimulator coil of FIGS. 3A-3D attached via cable to a box containing the device's impulse generator, control unit, and power source.

FIG. 4A is a perspective view of a dual-electrode stimulator according to another embodiment of the present invention.

FIG. 4B is a cut-a-way view of the dual-electrode stimulator of FIG. 4A.

FIG. 6A illustrates the approximate position of the housing of the stimulator according one embodiment of the present invention, when used to stimulate the right vagus nerve in the neck of an adult patient.

DETAILED DESCRIPTION OF THE PREFERRED EMBODIMENTS

Figure 1:
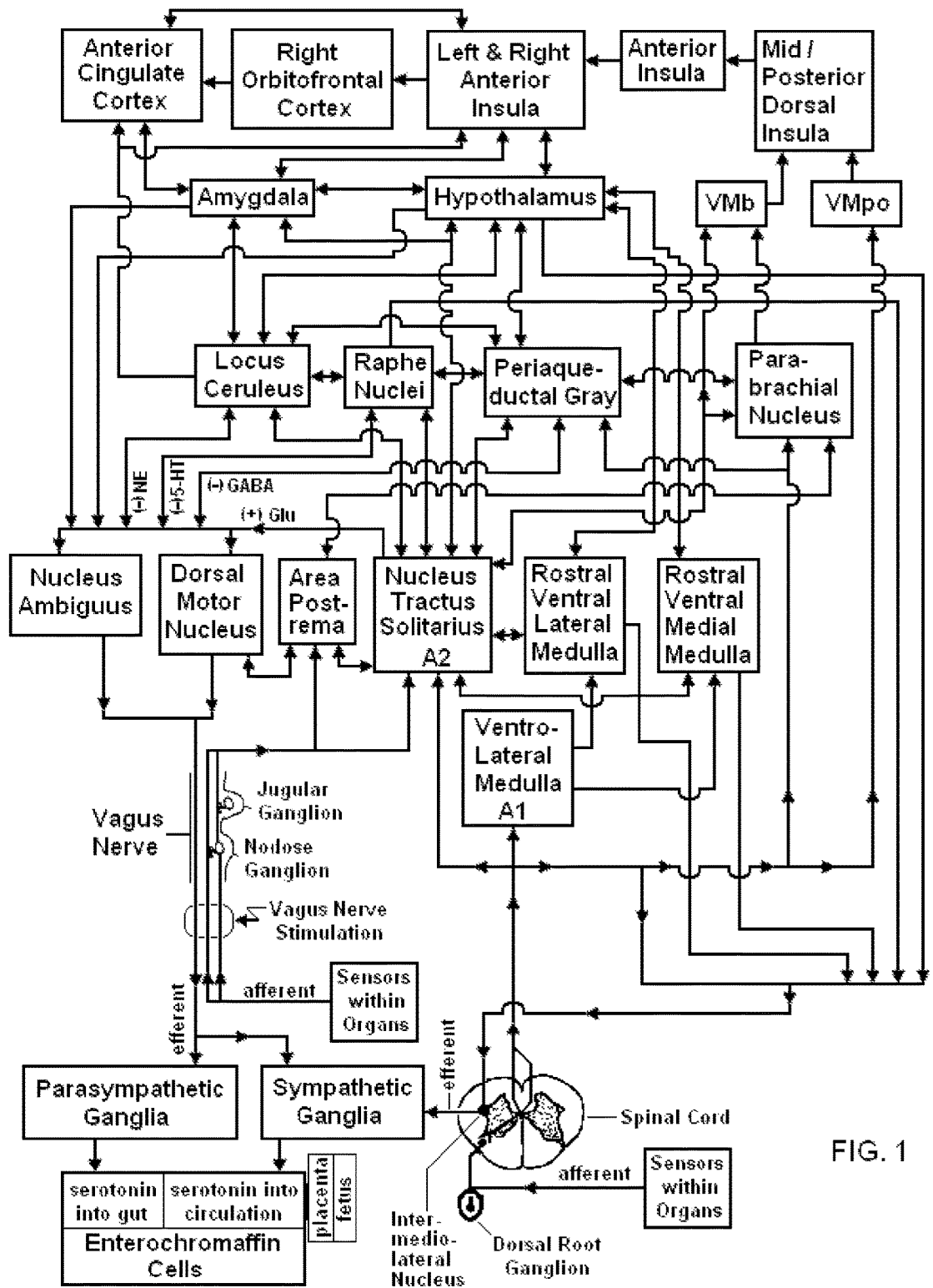
FIG. 1 shows structures within a patient's nervous system that may be abnormal in autistic patients, or within a pregnant woman who is at risk for having an autistic child, the physiology of which may be modulated by electrical stimulation of a vagus nerve.

In one embodiment of the invention, a time-varying magnetic field, originating and confined to the outside of a patient, generates an electromagnetic field and/or induces eddy currents within tissue of the patient. In another embodiment, electrodes applied to the skin of the patient generate currents within the tissue of the patient. An objective of the invention is to produce and apply the electrical impulses so as to interact with the signals of one or more nerves, in order to achieve the therapeutic result of altering a disorder of psychological development, more particularly a pervasive developmental disorder, and even more particularly, the disorder of autism. In the disclosure that follows, the developmental condition is usually referred to as autism, but with the understanding that unless otherwise indicated, the discussion could apply to other conditions of psychological development as well [Geraldine DAWSON and Karen Toth. Autism spectrum disorders. Chapter 8 (pp. 317-357) In: Developmental Psychopathology. Vol 3. Risk, Disorder, and Adaptation, 2nd Edn., Dante Cicchetti and Donald J Cohen, eds. Hoboken: N.J.: John Wiley & Sons: (2006); LEVY S E, Mandell D S, Schultz R T. Autism. Lancet 374(9701, 2009):1627-1638; William J BARBARESI. Autism: a review of the state of the science for pediatric primary health care clinicians. Arch Pediatr Adolesc Med 160 (2006):1167-1175; RAPIN I, Tuchman R F. Autism: definition, neurobiology, screening, diagnosis. Pediatr Clin North Am 55(5, 2008):1129-1146; VOLKMAR F R, Lord C, Bailey A, Schultz R T, Klin A. Autism and pervasive developmental disorders. J Child Psychol Psychiatry 45(1, 2004):135-170; Ami KLIN. Autism and Asperger syndrome: an overview. Rev Bras Psiquiatr 28(Supl I, 2006):S3-S11].

Much of the disclosure will be directed specifically to treatment of a patient by electromagnetic stimulation in or around a vagus nerve, with devices positioned non-invasively on or near a patient's neck. However, it will also be appreciated that the devices and methods of the present invention can be applied to other tissues and nerves of the body, including but not limited to other parasympathetic nerves, sympathetic nerves, spinal or cranial nerves. As recognized by those having skill in the art, the methods should be carefully evaluated prior to use in patients known to have preexisting cardiac issues.

In some embodiments, the technologies disclosed herein are used to provide therapy or treat or control medical, psychiatric, or neurological disorders, or of any of several types of neuropsychiatric disorders, such as schizophrenia, depression, and borderline personality disorder.

In some embodiments, a method stimulates the vagus nerve using the toroidal magnetic stimulation device. The position and angular orientation of the device are adjusted about that location until the patient perceives stimulation when current is passed through the stimulator coils. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position. The stimulator signal may have a frequency and other parameters that are selected to influence the therapeutic result. For example, a pulse width may be from about 0.01 ms to 500.0 ms, typically 200 ms. The pulses may be delivered at a frequency of 0.5 to 500 Hz., typically 20 Hz. The stimulation may be performed for 1 to 200 minutes, typically for 30 minutes. Typically, the treatment is performed repeatedly, e.g., once a week for six months. However, parameters of the stimulation may be varied in order to obtain a beneficial response, as indicated, for example, by the measurement of levels and/or activities of TGF-beta, neurotrophic factors, retinoic acid, and/or TNF-alpha in the patient's peripheral circulation and/or in the patient's cerebrospinal fluid, during and subsequent to each treatment.

FIG. 1 shows the location of the stimulation as "Vagus Nerve Stimulation," relative to its connections with other anatomical structures that are affected by the stimulation. In different embodiments of the invention, various brain and brainstem structures are preferentially modulated by the stimulation, and in another embodiment of the invention the objective is to stimulate certain cells located in the gut (enterochromaffin cells). These structures will be described in sections of the disclosure that follow, along with the rationale for modulating their activity as a prophylaxis or treatment for autism or other neurodevelopmental disorders. As a preliminary, we first describe the vagus nerve itself and its most proximal connections, which are particularly relevant to the disclosure below of the electrical waveforms that are used to perform the stimulation.

The vagus nerve (tenth cranial nerve, paired left and right) is composed of motor and sensory fibers. The vagus nerve leaves the cranium, passes down the neck within the carotid sheath to the root of the neck, then passes to the chest and abdomen, where it contributes to the innervation of the viscera, including the gut that contains enterochromaffin cells.

A vagus nerve in man consists of over 100,000 nerve fibers (axons), mostly organized into groups. The groups are contained within fascicles of varying sizes, which branch and converge along the nerve. Under normal physiological conditions, each fiber conducts electrical impulses only in one direction, which is defined to be the orthodromic direction, and which is opposite the antidromic direction. However, external electrical stimulation of the nerve may produce action potentials that propagate in orthodromic and antidromic directions. Besides efferent output fibers that convey signals to the various organs in the body from the central nervous system, the vagus nerve conveys sensory (afferent) information about the state of the body's organs back to the central nervous system. Some 80-90% of the nerve fibers in the vagus nerve are afferent (sensory) nerves, communicating the state of the viscera to the central nervous system. Propagation of electrical signals in efferent and afferent directions are indicated by arrows in FIG. 1. If communication between structures is bidirectional, this is shown in FIG. 1 as a single connection with two arrows, rather than showing the efferent and afferent nerve fibers separately.

The largest nerve fibers within a left or right vagus nerve are approximately 20 μm in diameter and are heavily myelinated, whereas only the smallest nerve fibers of less than about 1 μm in diameter are completely unmyelinated. When the distal part of a nerve is electrically stimulated, a compound action potential may be recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories, with approximate diameters as follows: A-alpha fibers (afferent or efferent fibers, 12-20 µm diameter), A-beta fibers (afferent or efferent fibers, 5-12 µm), A-gamma fibers (efferent fibers, 3-7 µm), A-delta fibers (afferent fibers, 2-5 µm), B fibers (1-3 µm) and C fibers (unmyelinated, 0.4-1.2 µm). The diameters of group A and group B fibers include the thickness of the myelin sheaths. It is understood that the anatomy of the vagus nerve is developing in newborns and infants, which accounts in part for the maturation of autonomic reflexes. Accordingly, it is also understood that the parameters of vagus nerve stimulation in the present invention are chosen in such a way as to account for this age-related maturation [PEREYRA P M, Zhang W, Schmidt M, Becker L E. Development of myelinated and unmyelinated fibers of human vagus nerve during the first year of life. J Neurol Sci 110(1-2, 1992): 107-113; SCHECHTMAN V L, Harper R M, Kluge K A. Development of heart rate variation over the first 6 months of life in normal infants. Pediatr Res 26(4, 1989):343-346].

The vagus (or vagal) afferent nerve fibers arise from cell bodies located in the vagal sensory ganglia. These ganglia take the form of swellings found in the cervical aspect of the vagus nerve just caudal to the skull. There are two such ganglia, termed the inferior and superior vagal ganglia. They are also called the nodose and jugular ganglia, respectively (See FIG. 1). The jugular (superior) ganglion is a small ganglion on the vagus nerve just as it passes through the jugular foramen at the base of the skull. The nodose (inferior) ganglion is a ganglion on the vagus nerve located in the height of the transverse process of the first cervical vertebra.

Vagal afferents traverse the brainstem in the solitary tract, with some eighty percent of the terminating synapses being located in the nucleus of the tractus solitarius (or nucleus tractus solitarii, nucleus tractus solitarius, or NTS, see FIG. 1). The NTS projects to a wide variety of structures in the central nervous system, such as the amygdala, raphe nuclei, periaqueductal gray, nucleus paragigantocellurlais, olfactory tubercule, locus ceruleus, nucleus ambiguus and the hypothalamus. The NTS also projects to the parabrachial nucleus, which in turn projects to the hypothalamus, the thalamus, the amygdala, the anterior insula, and infralimbic cortex, lateral prefrontal cortex, and other cortical regions [JEAN A. The nucleus tractus solitarius: neuroanatomic, neurochemical and functional aspects. Arch Int Physiol Biochim Biophys 99(5, 1991):A3-A52]. Such central projections are discussed below in connection with the interoception and resting state neural networks.

With regard to vagal efferent nerve fibers, two vagal components have evolved in the brainstem to regulate peripheral parasympathetic functions. The dorsal vagal complex, consisting of the dorsal motor nucleus and its connections (see FIG. 1), controls parasympathetic function primarily below the level of the diaphragm (e.g. gut and its enterochromaffin cells), while the ventral vagal complex, comprised of nucleus ambiguus and nucleus retrofacial, controls functions primarily above the diaphragm in organs such as the heart, thymus and lungs, as well as other glands and tissues of the neck and upper chest, and specialized muscles such as those of the esophageal complex. For example, the cell bodies for the preganglionic parasympathetic vagal neurons that innervate the heart reside in the nucleus ambiguus, which is relevant to potential cardiovascular side effects that may be produced by vagus nerve stimulation.

With the foregoing as preliminary information about the vagus nerve, the topics that are presented below in connection with the disclosure of the invention include the following: (1) Use of the vagus nerve stimulator to condition the behavior of a child; (2) Overview of physiological mechanisms through which the disclosed vagus nerve stimulation methods may be used to modulate the neuronal circuitry of individuals with pervasive developmental disorders; (3) Description of Applicant's magnetic and electrode-based nerve stimulating devices, describing in particular the electrical waveform used to stimulate a vagus nerve; (4) Preferred embodiments of the magnetic stimulator; (5) Preferred embodiments of the electrode-based stimulator; (6) Application of the stimulators to the neck of the patient; (7) Use of the devices with feedback and feedforward to improve treatment of individual patients.

Use of the Vagus Nerve Stimulator to Condition the Behavior of a Child

The first aspect of the present invention is an application of an earlier invention that we disclosed in a commonly assigned, co-pending application Ser. No. 13/024,727, entitled Non-invasive methods and devices for inducing euphoria in a patient and their therapeutic application, to SIMON et al, which is incorporated by reference. As disclosed in that earlier application, vagus nerve stimulation may be used to create a state of euphoria in an individual. That is to say, with appropriate devices and electrical stimulus parameters, the stimulation can create a euphoric sensation in the stimulated individual. This discovery is used in the present invention as a conditioning tool, with which improved behavior on the part of a child is rewarded or positively reinforced. For example, when the child exhibits a desired behavior, such as making eye contact with the therapist or some other individual, the child is rewarded with euphoric stimulation through the vagus nerve stimulator. When the child is not behaving in a developmentally desirable fashion, the euphoric stimulation is generally withheld. It is understood that undesirable behavior could in principle be punished with unpleasant, aversive electrical stimulation as well, but such aversive stimuli are discouraged in the present invention [U.S. Pat. No. 4,440,160, entitled Self-injurious behavior inhibiting system, to FISCHELL et al.; LICHSTEIN K L, Schreibman L. Employing electric shock with autistic children. A review of the side effects. J Autism Child Schizophr 6(2, 1976):163-173]. On the other hand, a therapeutically beneficial signal that is neutral with regard to its sensed pleasantness versus unpleasantness may be administered alone or in combination with euphoric stimulation, as described in the following section.

Even if the child is to be treated with vagus nerve stimulation that is directed to neural circuits other than those involved in producing the euphoria (as disclosed in the following section), the treatment may ordinarily begin with, or be accompanied by, euphoric vagus nerve stimulation anyway. The reason is that the children to be treated will often be uncooperative and will resist the placement and long-term application of the noninvasive vagus nerve stimulator on their neck, unless they are motivated to cooperate. The prospect of the euphoric stimulation provides that motivation. However, it is understood that some children will always resist the application of a noninvasive vagus nerve stimulator, and for them euphoric conditioning methods might only be feasible if a stimulation electrode is implanted about the vagus nerve, or if deep brain stimulation is used instead in an attempt to produce the euphoric state of mind, but this would ordinarily be undertaken only if there were other primary reasons for performing such invasive procedures.

Turning now to the methods of conditioning children with autism or another developmental disorder—the vagus nerve stimulator, ordinarily situated in a neck collar, is placed on the child's neck. Such a collar and device will be described below (see FIG. 6B), along with methods that compensate for changes in the position of the stimulator relative to the vagus nerve, for example, as the child moves his neck within the limits of constraint of the collar. The stimulation parameters that produce a euphoric sense are then determined empirically for each child. Control of the stimulator parameters (on/off, frequency, pulse width, etc.) will ordinarily be accomplished remotely, using a controller that communicates with the stimulator wirelessly and that can be adjusted by the therapist or parent.

The presence or absence of the euphoric vagus nerve stimulation is then controlled by the therapist or parent, as required by the situation at hand and by the goals of the therapy. Intermediate stimulation magnitudes may also be used, if different levels of euphoria are desired. Ordinarily, the therapist or parent will have already indicated to the child what type of behavior is desired. In general, the therapy is directed towards promoting developmentally appropriate social interaction and communication, as well as the absence of restricted interests and repetitive behavior. Examples of different categories of conditioning using the stimulator are as follows.

As an example of treating impairment in the use of non-verbal behaviors, the child is conditioned to improve and increase eye-to-eye gaze with the therapist or with other individuals. When the autistic child makes eye contact, the euphoric stimulation is applied promptly thereafter, and when eye contact is not made or is lost, the euphoric stimulation is promptly turned off. Once the euphoric reward for some activity, such as making eye contact, has produced a significant result over the course of prolonged therapy, the reward for that activity may be made less frequent or with a reduced amplitude ("fading" or "thinning", e.g., stimulate on every other eye contact, or only when making eye contact with different individuals, etc), unless there is regression on the part of the child.

As an example of improving development of peer relationships, the euphoric stimulation is applied when the autistic child interacts with a child of roughly the same age, but not when the autistic child interacts with an adult or with a much younger or much older child.

As an example of promoting the sharing of interests with others, euphoric stimulation is applied when there is a demonstration of joint attention, e.g. when the autistic child points to something, to call the therapist's or parent's attention to that object.

As an example of promoting an increased social reciprocity, euphoric stimulation is applied when the autistic child heeds the suggestion of another child.

As an example of promoting the use of spoken or non-verbal language, euphoric stimulation is applied depending on developmental stage, e.g., when the autistic child uses a spoken word or facial expression or gesture.

As an example of promoting non-repetition of words, euphoric stimulation is applied when the child responds to words spoken to the child, but only when the response is not simply a repetition of those same words.

As an example of promoting engagement in conversation, euphoric stimulation is applied when the autistic child makes multiple statements in a conversation, as in statement), response1, statement2, response2 . . . .

As an example of promoting novelty in pretend play, euphoric stimulation is applied when the autistic child uses of a new doll or object, or plays with the doll or object in a new way.

As an example of promoting interest in a new subject, euphoric stimulation is applied when the autistic child asks a question that is different than a question that has been repeatedly asked and answered in the past; or when the child takes an interest in a new television program.

As an example of promoting flexibility in routines or the loss of ritual behavior, euphoric stimulation is applied when the autistic child does not complain that his clothing has a color other than the preferred color, or that the drive to the store takes a new route.

As an example of promoting the loss of repetitive or stereotyped behavior, euphoric stimulation is withheld when the autistic child exhibits stereotypic behavior such as arm flapping, rocking, toe-walking, the assumption of odd postures, etc.

As an example of promoting the loss of preoccupation with particular objects, euphoric stimulation is withheld when the autistic child lines objects in a row, opens and closes doors repeatedly, turns lights on and off repeatedly, transfers water repeatedly from one vessel to another, spins the wheels of a toy repeatedly, etc.

It is understood that positive reinforcement for producing developmentally appropriate behavior is already part of applied behavior analysis programs that treat autism [VISMARA L A, Rogers S J. Behavioral treatments in autism spectrum disorder: what do we know? Annu Rev Clin Psychol 6 (2010):447-468; WARREN Z, Veenstra-VanderWeele J, Stone W, et al. Therapies for Children With Autism Spectrum Disorders. Comparative Effectiveness Review No. 26. (Prepared by the Vanderbilt Evidence-based Practice Center under Contract No. 290-2007-10065-I.) AHRQ Publication No. 11-EHC029-EF. Rockville, Md.: Agency for Healthcare Research and Quality. April 2011, 908 pp]. Perhaps the best known example of such applied behavior analysis is the UCLA/Lovaas-based intervention, which involves discrete-trial teaching, breaking skills down into their most basic components, then rewarding positive performance with praise and reinforcers. According to the present invention, euphoric vagus nerve stimulation may be used as a reinforcer in all such programs, replacing or complementing conventional reinforcers that are already used in such programs.

The euphoric stimulation may also be used as a reward in learning programs for autistic children, when the child has acquired new skills or knowledge. Advantages in regard to the euphoric stimulation as a reinforcer include the properties: that by varying stimulation amplitudes, gradations of euphoric stimulation reinforcement may be possible (variable or contingent reinforcement); and it is possible to use concomitant or alternating stimulation waveforms that are directed to the particular neural networks that are implicated in autistic behavior, in addition to the euphoric neural networks. Thus, in a preferred embodiment, the vagus nerve stimulation is not only pleasant to the child and useful for conditioning developmentally appropriate social interaction and communication, as well as the absence of restricted interests and repetitive behavior, but it may also compensate for imbalances or other abnormalities in the child's neural networks that may be responsible for the behavior that is being conditioned, as described in the next section. That is to say, in the preferred embodiment, the vagus nerve stimulator is used not only as a behavioral or educational reinforcer, but also as a medical tool.

Overview of Physiological Mechanisms Through which the Disclosed Vagus Nerve Stimulation Methods May be Used to Modulate the Neuronal Circuitry of Individuals with Pervasive Developmental Disorders We now disclose methods and devices for electrically stimulating a vagus nerve noninvasively, in order to provide medical treatment to an individual having or developing a pervasive developmental disorder such as autism. Although the treatment is medical, it should be understood at the outset that autism is not a disease. It is instead a disorder in which anatomical components of the cerebral cortex that are responsible for the emergence of cognitive properties do not develop and connect to one another normally.

Neurodevelopmental disorders such as autism are characterized by a series of missed developmental milestones that would normally occur before birth and during early childhood. The natural history of autism may involve three components: (1) there is an underlying vulnerability to the development of the child's brain, particularly a set of genetic abnormalities; (2) there are exogenous stressors; and (3) brain structures and connections that would normally form at critical times during development of the brain do not form normally, resulting in a cascade of pathological events that are significantly influenced by environmental factors. It is understood that such milestones may be interpretable ultimately in terms of the spatio-temporal sequences of gene expression in the developing brain [KANG H J, Kawasawa Y I, Cheng F, et al. Spatio-temporal transcriptome of the human brain. Nature 478(7370, 2011):483-489].

Underlying brain alterations in autism occur well before corresponding symptoms are manifest. The initial neurodevelopmental disruption that is responsible for autism may begin as early as embryonic day 40 and is generally thought to arise during the first trimester of a pregnancy. Thus, in utero exposure to valproic acid and other anticonvulsants significantly increase the risk for manifesting autism or autistic-like traits postnatally. Other drugs that affect the likelihood of a fetus developing into an autistic child include thalidomide, misoprostol, selective serotonin reuptake inhibitors, cocaine, and ethanol. Rubella exposure during the first trimester also increases the risk of autism. The timing of the underlying insult (e.g., first trimester) may be of equal, if not greater importance, than the anatomical loci affected. However, the likelihood of developing autism is also a function of additional factors, particularly the genetics of the child [DUFOUR-Rainfray D, Vourc'h P, Tourlet S, Guilloteau D, Chalon S, Andres C R. Fetal exposure to teratogens: evidence of genes involved in autism. Neurosci Biobehav Rev 35(5, 2011):1254-65; MEYER U, Yee B K, Feldon J. The neurodevelopmental impact of prenatal infections at different times of pregnancy: the earlier the worse? Neuroscientist 13(3, 2007):241-256].

Autism has a strong genetic component. Studies of twins suggest that heritability is as high as 0.9 for autism spectrum disorders, and siblings of those with autism are about 25 times more likely to be autistic than the general population. Common alleles that increase relative risk for autism by 2-fold or more have been sought intensely, but alleles of putative risk genes that are found frequently in the population (e.g., MACROD2, KIAA0564, PLD5, POU6F2, ST8SIA2 and TAF1C) have failed to demonstrate such risk. More likely, the genetic roots of autism trace to hundreds of rare de novo and inherited copy number variants, suggesting a key role for gene dosage in susceptibility to autism, often in genes that encode proteins affecting neuronal development such as those involved in synaptic cell adhesion.

Nevertheless, it is worth testing for abnormal genes that are associated with genetic syndromes that may be comorbid with autism, such as FMR1 (fragile X syndrome), TSC1 and TSC2 (tuberous sclerosis), PTEN (hamartoma tumor syndrome) and MECP2 (Rett syndrome) [Ravinesh A KUMAR. Genetics of autism spectrum disorders. Curr Neurol Neurosci Rep 9(2009):188-197; GESCHWIND D H. Genetics of autism spectrum disorders. Trends Cogn Sci 15(9, 2011): 409-416; Judith H. MILES. Autism spectrum disorders—A genetics review. Genet Med 13(4, 2011):278-294; SHEN Y, Dies K A, Holm I A, et al. Clinical genetic testing for patients with autism spectrum disorders. Pediatrics 125(4, 2010):e727-e735]. Disorders with autistic spectrum features often derive from compromised regulation of mTOR-linked signaling pathways (mammalian target of rapamycin, mTOR, which is a protein encoded by the FRAP1 gene). Notably, mTOR is the hub of a signaling pathway that includes PTEN, TSC1, and TSC2. The mTOR-signalling pathways are connected to glutamate signaling pathways via the gene mGluR5.

In view of the likelihood that the brain of an autistic child may miss a series of neuro-developmental milestones that can occur during only during particular time-windows, both in utero and after birth, a prophylactic intervention that would stop or redirect the abnormal developmental progression should take into account the then-existing developmental state of the child's brain. Once a time-window for a particular developmental stage has closed, the abnormal brain structure may have become irreversibly formed, and the intervention to treat the abnormality would be then characterized as an attempt to induce a compensatory structure, function, or loss of function. Accordingly, the present invention generally contemplates two types of interventions, prophylactic and compensatory. With a compensatory intervention, the developmental neuroanatomical abnormalities are not prevented, but the functional defects arising from such abnormalities are preferably minimized or reversed using a countermeasure involving vagus nerve stimulation [MEREDITH R M, Dawitz J, Kramvis I. Sensitive time-windows for susceptibility in neurodevelopmental disorders. Trends Neurosci 35(6, 2012):335-344; HENSCH T. K. Critical period plasticity in local cortical circuits. Nature Reviews Neuroscience, 6(2005): 877-888; EHNINGER D, Li W, Fox K, Stryker M P, Silva A J. Reversing neurodevelopmental disorders in adults. Neuron 60(6, 2008):950-960].

Because the earliest stages of abnormal autistic neurodevelopment occur in utero, the invention considers using vagus nerve stimulation of the mother, in order to prevent abnormal neurodevelopment of the fetus. The vagus nerve stimulation is preferably performed during the first trimester, in an attempt to modulate the mother's circulating levels of serotonin (5-HT). The current literature does not discourage such an intervention, because vagus nerve stimulation of a pregnant mother does not have any known deleterious effect on the developing fetus, at least as it is ordinarily performed [HUSAIN M M, Stegman D, Trevino K. Pregnancy and delivery while receiving vagus nerve stimulation for the treatment of major depression: a case report. Ann Gen Psychiatry 4(2005):16, pp. 1-7; HOUSER M V, Hennessy M D, Howard B C. Vagal nerve stimulator use during pregnancy for treatment of refractory seizure disorder. Obstet Gynecol 115(2 Pt 2, 2010):417-419].

Pregnant women who are taking serotonin reuptake inhibitors are at increased risk of having an autistic child.

Cocaine, which is a competitive antagonist of the serotonin transporter and has an action similar to selective serotonin reuptake inhibitors, is also a significant risk factor for autism [CROEN L A, Grether J K, Yoshida C K, Odouli R, Hendrick V. Antidepressant use during pregnancy and childhood autism spectrum disorders. Arch Gen Psychiatry 68(11, 2011):1104-1112; DAVIS E, Fennoy I, Laraque D, Kanem N, Brown G, Mitchell J. Autism and developmental abnormalities in children with perinatal cocaine exposure. J Natl Med Assoc 84(4, 1992):315-319]. Consequently, to the extent that a depressed pregnant women use vagus nerve stimulation in lieu of taking serotonin reuptake inhibitors or cocaine to treat depression, that in and of itself may be considered to be an intervention to prevent autism in the child.

Vagus nerve stimulation may also be used to prevent autism in pregnant women irrespective of whether they are taking serotonin reuptake inhibitors or cocaine. This is because the known role of 5-HT in brain development raises the possibility that increased 5-HT levels reaching the fetus via the placenta may result in more normal neuronal migration or neurite outgrowth. In fact, in the earliest stages of development, almost all of the fetus's serotonin comes from the mother, although some might also come from de novo synthesis from tryptophan in the placenta itself [COTE F, Fligny C, Bayard E, Launay J M, Gershon M D, Mallet J, Vodjdani G. Maternal serotonin is crucial for murine embryonic development. Proc Natl Acad Sci USA. 2007 Jan. 2; 104(1, 2007):329-334].

Approximately 90% of the human body's total serotonin is located in the enterochromaffin cells in the gut, where it is used to regulate intestinal movements and control circulating serotonin levels. Release of the serotonin from the enterochromaffin cells is regulated by the vagus nerve, and its release into the portal circulation is controlled by vagal efferent adrenergic nerve fibers [GRONSTAD K O, Zinner M J, Nilsson O, Dahlström A, Jaffe B M, Ahlman H. Vagal release of serotonin into gut lumen and portal circulation via separate control mechanisms. J Surg Res 44(2, 1988):146-151; PETTERSSON G. The neural control of the serotonin content in mammalian enterochromaffin cells. Acta Physiol Scand Suppl 470(1979):1-30]. Thus, by electrically stimulating the vagus nerve in such a way as to increase the activity of vagal efferent adrenergic nerve fibers, the release of serotonin into the circulation of the mother and placenta will also be increased. The mechanism is illustrated in FIG. 1 and is described more completely in paragraphs below.

Stimulation of the cervical (or thoracic) vagus nerve at the site shown in the FIG. 1 causes the release of serotonin into the gut by a cholinergic pathway, and into the portal circulation by an adrenergic pathway. The adrenergic pathway is abolished when the superior cervical sympathetic ganglia are removed. The adrenergic nerve stimulation may be direct, along efferent vagus nerve fibers, or it may be indirect wherein afferent vagal fibers are stimulated that indirectly increase the activity of the efferent adrenergic nerve fibers via central feedback mechanisms involving loops in the neural circuitry shown in FIG. 1, through the intermediolateral nucleus of the spinal cord. We note that similar effects might be obtained by electrically simulating the splanchnic nerve [LARSSON I, Ahlman H, Bhargava H N, Dahlström A, Pettersson G, Kewenter J. The effects of splanchnic nerve stimulation on the plasma levels of serotonin and substance P in the portal vein of the cat. J Neural Transm 46(2, 1979):102-112].

Almost all of the serotonin that is released into the portal circulation is sequestered by platelets via serotonin transporters. The platelets are thought to release the serotonin in the placenta, whereupon the maternal serotonin is actively transported through the placental brush border cells via serotonin transporters [COTE F, Fligny C, Bayard E, Launay J M, Gershon M D, Mallet J, Vodjdani G. Maternal serotonin is crucial for murine embryonic development. Proc Natl Acad Sci USA. 2007 Jan. 2; 104(1, 2007):329-334; YAVARONE M S, Shuey D L, Sadler T W, Lauder J M. Serotonin uptake in the ectoplacental cone and placenta of the mouse. Placenta 14(2, 1993):149-161]. If the mother is taking serotonin reuptake inhibitors that target the serotonin transporter, then the platelet sequestration and placental transport of serotonin will be reduced, such that there would be decreased availability of serotonin to the developing fetus. Thus, the platelets would then contain abnormally low levels of serotonin, and the transport of serotonin across the placenta would also be reduced. In such a situation, the vagus nerve stimulation is an intervention to increase the maternal circulating levels of serotonin as compensation for the inactivity of the serotonin transporters, brought about by the use of serotonin reuptake inhibitors or cocaine.

The opposite problem may occur in families that are genetically predisposed to autism by virtue of a mutation in the serotonin transporter, wherein the problem lies not in the difficulty of getting serotonin into the platelet, but in the difficulty of getting serotonin out of the platelet (as well as out of a presynaptic nerve body and across a synapse). In that case, the serotonin transporter is overactive, such that the platelets will develop abnormally high levels of serotonin, because the overactive transporter antagonizes, counteracts or reabsorbs any release of serotonin from the platelets [VEENSTRA-VanderWeele J, Muller C L, Iwamoto H, et al. Autism gene variant causes hyperserotonemia, serotonin receptor hypersensitivity, social impairment and repetitive behavior. Proc Natl Acad Sci USA 109(14, 2012): 5469-5474]. In such a case, the use of serotonin reuptake inhibitors may actually be useful. Vagus nerve stimulation of the mother may still also be helpful, in an effort to downregulate the production of the overactive maternal serotonin transporters. Thus, the synthesis of serotonin transporters is a function of the plasma serotonin concentration, such that at the relatively high levels of plasma serotonin that would be induced by vagus nerve stimulation, the production of maternal serotonin transporters would be inhibited, so that less of any released serotonin could be reabsorbed [MERCADO C P, Kilic F. Molecular mechanisms of SERT in platelets: regulation of plasma serotonin levels. Mol Interv 10(4, 2010):231-241].

It is advisable to confirm that the maternal and fetal genetics are consistent with such an autism gene variant, because there are potential causes of elevated circulating serotonin levels in autistic individuals, other than the heritable overactive serotonin transporter that is associated with the autism-related variant serotonin transporter gene [JANUSONIS S. Origin of the blood hyperserotonemia of autism. Theor Biol Med Model 22(2008); 5:10, pp 1-16]. Otherwise, the vagus nerve stimulation might not have its intended effect [WHITAKER-Azmitia P M. Behavioral and cellular consequences of increasing serotonergic activity during brain development: a role in autism? Int J Dev Neurosci 23(1, 2005):75-83]. Thus, after an analysis like that described by JANUSONIS, it may be concluded that the mother's circulating serotonin levels would best be decreased. In that case, by electrically stimulating the vagus nerve in such a way as to decrease the activity of vagal efferent adrenergic nerve fibers through application of blocking or inhibiting electrical pulses (directly or indirectly via central feedback mechanisms), the release of serotonin into the circulation of the mother and placenta would be decreased.

Another caveat is the following. Because serotonin does not cross the blood-brain barrier, this intervention would not be expected to lead to cognitive side effects in the mother, but because serotonin levels affect blood pressure and have other cardiovascular effects, those side effects should be anticipated and possibly treated [WATTS S W, Morrison S F, Davis R P, Barman S M. Serotonin and blood pressure regulation. Pharmacol Rev 64(2, 2012):359-388].

A prophylactic or compensatory intervention involving electrical stimulation of the fetus itself is also conceivable, because embryogenesis makes use of endogenously produced electric fields, and externally applied electric fields have been used experimentally to modulate embryogenesis [Colin LOWRY. The Electric Embryo: How Electric Fields Mold the Embryo's Growth Pattern and Shape, 21st Century Science & Technology, Spring 1999, pp. 56-70]. Such externally applied electromagnetic fields have apparently never been considered in connection with preventing autism. The only investigations concerning the effect of endogenous electric fields on developing fetuses, as it relates to autism, have dealt with safety and mechanism issues, such as whether fetal brain tissue can demodulate microwave radiation at 217 Hz via oscillation of magnetite crystals [Richard LATHE. Microwave electromagnetic radiation and autism. Electronic Journal of Applied Psychology: Innovations in Autism. 5(1, 2009):11-30].

If treatment of the potentially autistic child does not begin in utero, then prophylactic or compensatory treatment could begin shortly after the birth of the child. In order to justify treating a newborn, there must be a reasonable likelihood that the child is or will become autistic. If a sibling has already been diagnosed with autism, the likelihood that the newborn is or will be autistic is significantly increased. At some point, it may even become possible to predict neuro-developmental abnormalities at birth through a comprehensive analysis of a placental or neonatal genetics [KNICK-MEYER R C, Wang J, Zhu H, Geng X, Woolson S, Hamer R M, Konneker T, Lin W, Styner M, Gilmore J H. Common Variants in Psychiatric Risk Genes Predict Brain Structure at Birth. Cereb Cortex. 2013 Jan. 2. (Epub ahead of print)]. However, it is currently difficult to diagnose autistic children before the age of two on the basis of behavior alone, by which time many neuro-developmental time-windows may have already closed. One problem in that regard is that some children behave normally shortly after birth, but retrogress after a year or more (false negatives). Another problem is that the child may have a different problem, such as retardation (false positives). It has been proposed that the best behavioral predictors of autism in infants are the frequency with which the child looked at other person, the abnormal ability to disengage and move his focus of attention, neo-natal auditory brainstem responses, and 4-month arousal-modulated attention visual preference [STONE W L, Lee E B, Ashford L, Brissie J, Hepburn S L, Coonrod E E, Weiss B H. Can autism be diagnosed accurately in children under 3 years? J Child Psychol Psychiatry 40(2, 1999):219-226; WERNER E, Dawson G, Osterling J, Dinno N. Brief report: Recognition of autism spectrum disorder before one year of age: a retrospective study based on home videotapes. J Autism Dev Disord 30(2, 2000):157-162; ZWAIGEN-BAUM L, Bryson S, Rogers T, Roberts W, Brian J, Szatmari P. Behavioral manifestations of autism in the first year of life. Int J Dev Neurosci 23(2-3, 2005):143-152; OSTER-LING J A, Dawson G, Munson J A. Early recognition of 1-year-old infants with autism spectrum disorder versus mental retardation. Dev Psychopathol 14(2, 2002):239-251; BRYSON S E, Zwaigenbaum L, McDermott C, Rombough V, Brian J. The Autism Observation Scale for Infants: scale development and reliability data. J Autism Dev Disord 38(4, 2008):731-738; JOHNSON C P. Recognition of autism before age 2 years. Pediatr Rev 29(3, 2008):86-96; COHEN I L, Gardner J M, Karmel B Z, Phan H T, Kittler P, Gomez T R, Gonzalez M G, Lennon E M, Parab S, Barone A. Neonatal Brainstem Function and 4-Month Arousal-Modulated Attention Are Jointly Associated With Autism. Autism Res. 2012 Nov. 16. (Epub ahead of print)].

The suspicion of autism in a newborn may be confirmed or contradicted to some extent with evidence provided by biomarker data [WALSH P, Elsabbagh M, Bolton P, Singh I. In search of biomarkers for autism: scientific, social and ethical challenges. Nat Rev Neurosci 12(10, 2011):603-612; VEENSTRA-VanderWeele J, Blakely R D. Networking in autism: leveraging genetic, biomarker and model system findings in the search for new treatments. Neuropsychopharmacology 37(1, 2012):196-212; RATAJCZAK H V. Theoretical aspects of autism: biomarkers—a review. J Immunotoxicol 8(1, 2011):80-94; HENDREN R L, Bertoglio K, Ashwood P, Sharp F. Mechanistic biomarkers for autism treatment. Med Hypotheses 73(6, 2009):950-954; SKJELDAL O H, Sponheim E, Ganes T, Jellum E, Bakke S. Childhood autism: the need for physical investigations. Brain Dev 20(4, 1998):227-233]. Genetic biomarkers were mentioned above, which would be considered in conjunction with family history. Another consideration is the anatomy of the child's brain. Diffusion tensor imaging may be used to evaluate whether aberrant development of white matter pathways is present in the brain of a 6-month old child, which appears to be a useful predictor of whether the child will become diagnosed with autism [WOLFF J J, Gu H, Gerig G, et al. Differences in white matter fiber tract development present from 6 to 24 months in infants with autism. Am J Psychiatry 169(6, 2012):589-600].

Another useful biomarker that was mentioned above has been recognized for over 50 years—elevated whole-blood serotonin (5-HT), which is unique to autism among developmental disorders. Although circulating 5-HT will not cross the blood-brain barrier of the newborn, it is presumed that the protein networks regulating peripheral 5-HT homeostasis are conserved in the brain, such that serotonergic raphe nuclei of the brain, which release serotonin to the rest of the brain, may be likewise abnormal. Changes in brain 5-HT homeostasis during development of the newborn's brain may then result in altered neuronal migration or neurite outgrowth that contributes to autism. Accordingly, in one aspect of the invention, vagus nerve stimulation of the newborn or infant is intended to increase the activity of raphe nuclei (see FIG. 1) to produce more serotonin in the newborn's brain, among those newborns who have demonstrable hyper-serotonemia due to an overactive serotonin transporter that is associated with an autism-related variant serotonin transporter gene, especially if they are also considered to be at high risk of developing autism for other reasons [Adrienne E. DORR and Guy Debonnel. Effect of vagus nerve stimulation on serotonergic and noradrenergic transmission. J Pharmacol Exp Ther 318(2, 2006):890-898; MANTA S, Dong J, Debonnel G, Blier P. Enhancement of the function of rat serotonin and norepinephrine neurons by sustained vagus nerve stimulation. J Psychiatry Neurosci 34(4, 2009):272-280; MANTA S, El Mansari M, Blier P. Novel attempts to optimize vagus nerve stimulation parameters on serotonin neuronal firing activity in the rat brain. Brain Stimul 5(3, 2012):422-429].

The brain size at 6 months is not a good predictor of whether an infant has or will develop autism [HAZLETT H C, Gu H, McKinstry R C, et al. Brain volume findings in 6-month-old infants at high familial risk for autism. Am J Psychiatry 169(6, 2012):601-608]. On the other hand, in autistic children, the brain undergoes a period of precocious growth during early postnatal life followed by a deceleration in age-related growth, such that the rate of growth of the brain in infants is a recognized biomarker for autism [COURCHESNE E, Carper R, Akshoomoff N. Evidence of brain overgrowth in the first year of life in autism. JAMA 290(2003): 337-344; DAWSON G, Munson J, Webb S J, Nalty T, Abbott R, Toth K. Rate of head growth decelerates and symptoms worsen in the second year of life in autism. Biol Psychiatry 61(4, 2007):458-464].

A variety of candidate processes have been proposed to explain brain overgrowth and deceleration in autistic children, most of which focus on factors that affect the rate of neuronal development. However, the more likely explanation is that autistic children not only have an unusual pattern of brain growth and deceleration, but they also have a more general pattern of whole body (e.g., skeletal and body weight) overgrowth followed by deceleration [CHAWARSKA K, Campbell D, Chen L, Shic F, Klin A, Chang J. Early generalized overgrowth in boys with autism. Arch Gen Psychiatry 68(10, 2011):1021-1031]. Accordingly, there appears to be an abnormality of growth stimulating factors during the child's first year, followed by a reversal of such factors in the second year (e.g., FGF-2, IGF-1, BDNF, and VEGF). Furthermore, serotonin, which is often held at elevated levels in the platelets of individuals with autism, has an important role not only in neuronal development, but also in bone and skeletal development. In fact, brain overgrowth in autism is correlated with the unusual variant of the serotonin transporter in autistic children [WASSINK T H, Hazlett H C, Epping E A, Arndt S, Dager S R, Schellenberg G D, Dawson G, Piven J. Cerebral cortical gray matter overgrowth and functional variation of the serotonin transporter gene in autism. Arch Gen Psychiatry 64(2007):709-717]. As noted above, the biochemistry of autism may involve defects surrounding the gene mTOR, which is the hub of a signaling pathway that includes PTEN and that is connected to glutamate signaling pathways via the gene mGluR5. It is therefore noteworthy that the autism-related serotonin transporter allele works with PTEN to influence brain size [PAGE D T, Kuti O J, Prestia C, Sur M. Haploinsufficiency for Pten and serotonin transporter cooperatively influences brain size and social behavior. Proc Natl Acad Sci USA 106(2009): 1989-1994].

Therefore, in another aspect of the invention, vagus nerve stimulation is used as a prophylaxis or countermeasure against unusual patterns of growth during the first and second years, through modulation of growth factors such as those mentioned above. BDNF appears to be involved in regulating key aspects of both metabolism and energy balance. Vagus nerve stimulation has been observed to simultaneously increase BDNF levels and decrease body weight. It also activates BDNF receptor TrkB [BANNI S, Carta G, Murru E, Cordeddu L, Giordano E, Marrosu F, Puligheddu M, Floris G, Asuni G P, Cappai A L, Deriu S, Follesa P. Vagus nerve stimulation reduces body weight and fat mass in rats. PLoS One 7(9, 2012):e44813, pp. 1-10; FURMAGA H, Carreno F R, Frazer A. Vagal nerve stimulation rapidly activates brain-derived neurotrophic factor receptor TrkB in rat brain. PLoS One 7(5, 2012):e34844, pp. 1-10]. Consequently, to the extent that an insufficiency in BDNF levels or activity contribute to the body overgrowth seen in autistic children during the first year, vagus nerve stimulation of the infant may simultaneously increase the BNDF levels and activity and counteract the abnormal growth rate of autistic infants. The vagus nerve stimulation may also induce an increased expression of other growth factors, such as FGF-2, which may likewise promote a more normal growth rate pattern in autistic children [FOLLESA P, Biggio F, Gorini G, Caria S, Talani G, Dazzi L, Puligheddu M, Marrosu F, Biggio G. Vagus nerve stimulation increases norepinephrine concentration and the gene expression of BDNF and bFGF in the rat brain. Brain Res 1179(2007):28-34]. Hepatocyte growth factor/scatter factor (HGF/SF) is another growth factor that is implicated in autism and that might be modulated by vagus nerve stimulation [LEVITT P. Disruption of interneuron development. Epilepsia 46(Suppl 7, 2005):22-28]. In regards to the manipulation of serotonin levels to promote a more normal growth rate, this may be done by modulating the activity of raphe nuclei in the infant's brain with vagus nerve stimulation, as described above.

Two more growth factor levels that might be modulated by vagus nerve stimulation, members of the fibroblast growth factor family FGF-22 and FGF-7, are known to influence the balance between excitation and inhibition in the brain, respectively, by promoting the organization of excitatory and inhibitory presynaptic terminals through activation of different signaling pathways via their specific receptors [TERAUCHI A, Johnson-Venkatesh E M, Toth A B, Javed D, Sutton M A, Umemori H. Distinct FGFs promote differentiation of excitatory and inhibitory synapses. Nature 465(7299, 2010):783-787; TERAUCHI A, Umemori H. Specific sets of intrinsic and extrinsic factors drive excitatory and inhibitory circuit formation. Neuroscientist 18(3, 2012):271-286]. The neurodevelopmental abnormalities in autism are thought to produce an imbalance between excitatory and inhibitory neurons, giving rise to inappropriate excitation [RUBENSTEIN J L, Merzenich M M. Model of autism: increased ratio of excitation/inhibition in key neural systems. Genes Brain Behav 2(5, 2003):255-267]. Much of what is known about such excitation-inhibition imbalance comes from investigating the role of genes that cause Fragile X and Rett syndromes, whose carriers often experience autistic-like symptoms. Fragile X syndrome is a disease of excitation-dominance, whereas in Rett syndrome the balance between cortical excitation and inhibition is shifted to favor inhibition over excitation.

To understand the mechanisms and consequences of excitation-inhibition imbalance in autism, consider that the cerebral cortex consists of two main classes of neurons, pyramidal cells and interneurons, which respectively use glutamate and c-aminobutyric acid (GABA) as their main neurotransmitters. In the adult cortex, pyramidal cells are excitatory while GABA-containing (GABAergic) interneurons are typically inhibitory. There are many subtypes of GABA-containing interneurons. Minicolumns represent the cellular and functional organization of glutamatergic and GABAergic neurons in the cerebral cortex, which are anatomically characterized by vertical arrays of pyramidal neurons with their dentrides and axon projections. Pyramidal cells arrays are accompanied by their GABAergic interneurons that establish synapses with pyramidal cells bodies, their axon emergences and dentrides. A narrowing of cortical minicolumns (i.e., a reduced distance between columns) has been shown in autistic patients. This reduced intercolumnar distance is thought to depend on structural/anatomical defects in GABAergic interneurons surrounding principal pyramidal cortical neurons [AMRAL D G, Schumann C M, Nordahl C W. Neuroanatomy of autism. Trends Neurosci 31(3, 2008):137-145; CASANOVA M F. The neuropathology of autism. Brain Pathol 17(4, 2007):422-433; PICKETT J, London E. The neuropathology of autism: a review. J Neuropathol Exp Neurol 64(11, 2005):925-935].

In autism, mutations that increase the activity or number of glutamate receptors, that increase the amount of glutamate in the synapse, or that amplify glutamate-mediated synaptic potentiation can increase the excitatory state of the brain. This may involve defects surrounding the gene mTOR, which is the hub of a signaling pathway that includes PTEN and that is connected to glutamate signaling pathways via the gene mGluR5. Likewise, mutations that increase the activity or number of GABA receptors, that increase the amount of GABA in the synapse, or that amplify GABA-mediated synaptic potentiation can decrease the excitatory state of the brain. GABAergic inhibition can be affected in two ways, presynaptically by a reduction in GABA release into the synapse or postsynaptically by an alteration in GABA receptor function. This may involve, for example, defects in the GABA-A receptor [GATTO C L, Broadie K. Genetic controls balancing excitatory and inhibitory synaptogenesis in neurodevelopmental disorder models. Front Synaptic Neurosci 2(2010):4, pp. 1-19; Rocco PIZZARELLI and Enrico Cherubini. Alterations of GABAergic signaling in autism spectrum disorders. Neural Plasticity 2011: Article 297153, pp. 1-12; RAMAMOORTHI K, Lin Y. The contribution of GABAergic dysfunction to neurodevelopmental disorders. Trends Mol Med 17(8, 2011):452-462]. However, many other types of genes are now known to play a role in the balance between the formation of excitatory and inhibitory synapses, mutations in any of which could contribute to autism. This is because synaptogenesis is a highly controlled process, involving a vast array of players which include cell adhesion molecules, scaffolding and signaling proteins, neurotransmitter receptors and proteins associated with the synaptic vesicle machinery (e.g., fibroblast growth factors, neuroligins, ephrins/Ephs, netrin-G ligands, LRRTMs, SynCAMs, and Wnts) [LEVINSON J N, El-Husseini A. New players tip the scales in the balance between excitatory and inhibitory synapses. Mol Pain 23(2005); 1:12, pp. 1-6].

The initial formation of GABAergic synapses is thought to be independent of neuronal activity, occurring through elaborate cell-cell recognition processes mediated by transmembrane cell adhesion molecules such as neurexin and neuroligin family members. However, postnatal development of synapses in brain regions such as the primary sensory cortex is modified by neuronal activity and sensory experience, such that the number and strength of glutamatergic and GABAergic synapses dynamically change in response to neural activity. The number of glutamatergic synapses appears to be controlled by relative activity among neurons, but the number of GABAergic synapses appears to be dependent on general activity [LETO K, Bartolini A, Rossi F. Development of cerebellar GABAergic interneurons: origin and shaping of the "minibrain" local connections. Cerebellum 7(4, 2008):523-529; TERAUCHI A, Umemori H. Specific sets of intrinsic and extrinsic factors drive excitatory and inhibitory circuit formation. Neuroscientist 18(3, 2012):271-286; DORRN A L, Yuan K, Barker A J, Schreiner C E, Froemke R C. Developmental sensory experience balances cortical excitation and inhibition. Nature 465(7300, 2010):932-936; BURRONE J, O'Byrne M, Murthy V N. 2002. Multiple forms of synaptic plasticity triggered by selective suppression of activity in individual neurons. Nature 420:414-418; HARTMAN K N, Pal S K, Burrone J, Murthy V N. Activity-dependent regulation of inhibitory synaptic transmission in hippocampal neurons. Nat Neurosci 9(5, 2006):642-649].

Consequently, it is disclosed that vagus nerve stimulation shortly after birth may be used to increase the number of inhibitory GABAergic synapses throughout the developing brain, so as to promote excitation-inhibition balance in a child that is, or would become, autistic with an excitation imbalance. The stimulation may be accompanied by other modalities of sensory stimulation, such as sound, successive pictures of faces, etc. Such nerve stimulation is intended to counteract neuronal inactivity during development, which would lead to reduced inhibition. However, because the resulting specific synaptic changes depend on the developmental stage at which the stimulation is performed, it is important that the stimulation be performed as soon after birth as it is determined that the child will likely become autistic, then continue at least to approximately the age of two, when synaptic modification would be most efficacious. After approximately two years of age, the effect of vagus nerve stimulation may have more to do with the inhibition of synaptic pruning than the formation of inhibitory synapses. The parameters of the vagus nerve stimulation may be selected or adjusted in such a way as to prevent or reduce abnormal high frequency components in the EEG of the child, which is a measure of excitation-inhibition imbalance [YIZHAR O, Fenno L E, Prigge M, et al. Neocortical excitation/inhibition balance in information processing and social dysfunction. Nature 477(7363, 2011):171-178; OREKHOVA, E. V. et al. Excess of high frequency electroencephalogram oscillations in boys with autism. Biol. Psychiatry 62(2007):1022-1029; CORNEW L, Roberts T P, Blaskey L, Edgar J C. Resting-state oscillatory activity in autism spectrum disorders. J Autism Dev Disord 42(9, 2012):1884-1894]. Those high frequency oscillations are also an indication of excessive short-range neural connections and insufficient long rang neural connections, as described below in connection with resting state networks. Some randomness in the vagus nerve stimulation parameters may also be introduced in order to promote differential development of GABAergic synapses, exploiting the tendency of glutamatergic synapses to be controlled by relative activity among neurons, but with the number of GABAergic synapses being dependent on general activity.

For children and adults who already exhibit autistic behavior, the time-window for the balancing intervention described above might be closing. Nevertheless, stimulation of the vagus nerve may be helpful for them as well, but in this case the promotion of inhibition may involve neurotransmitters in addition to GABA. Even in such a case, parameters of the vagus nerve stimulation may be selected or adjusted in such a way as to prevent or reduce abnormal high frequency components in the EEG of the individual, which is used as a measure of excitation-inhibition imbalance. Excitatory nerves within the dorsal vagal complex generally use glutamate as their neurotransmitter. To inhibit neurotransmission within the dorsal vagal complex, the present invention makes use of the bidirectional connections that the nucleus of the solitary tract (NTS) has with structures that produce inhibitory neurotransmitters, or it makes use of connections that the NTS has with the hypothalamus, which in turn projects to structures that produce inhibitory neurotransmitters. The inhibition is produced as the result of the stimulation waveforms that are described below. Thus, acting in opposition to glutamate-mediated activation by the NTS of the area postrema and dorsal motor nucleus are:

GABA, and/or serotonin, and/or norepinephrine from the periaqueductal gray, raphe nucei, and locus coeruleus, respectively. FIG. 1 shows how those excitatory and inhibitory influences combine to modulate the output of the dorsal motor nucleus. Similar influences combine within the NTS itself, and the combined inhibitory influences on the NTS and dorsal motor nucleus produce a general inhibitory effect.

The activation of inhibitory circuits in the periaqueductal gray, raphe nucei, and locus coeruleus by the hypothalamus or NTS may also cause circuits connecting each of these structures to modulate one another. Thus, the periaqueductal gray communicates with the raphe nuclei and with the locus coeruleus, and the locus coeruleus communicates with the raphe nuclei, as shown in FIG. 1 [PUDOVKINA O L, Cremers T I, Westerink B H. The interaction between the locus coeruleus and dorsal raphe nucleus studied with dual-probe microdialysis. Eur J Pharmacol 7(2002); 445(1-2):37-42.; REICHLING D B, Basbaum A I. Collateralization of periaqueductal gray neurons to forebrain or diencephalon and to the medullary nucleus raphe magnus in the rat. Neuroscience 42(1, 1991):183-200; BEHBEHANI M M. The role of acetylcholine in the function of the nucleus raphe magnus and in the interaction of this nucleus with the periaqueductal gray. Brain Res 252(2, 1982):299-307].

In another embodiment of the invention, vagus nerve stimulation is used to modulate the activity of particular neural networks known as resting state networks, many of which are thought to be abnormal in individuals with autism. The individual may be a child or an adult. A neural network in the brain is accompanied by oscillations within the network. Low frequency oscillations are likely associated with connectivity at the largest scale of the network, while higher frequencies are exhibited by smaller sub-networks within the larger network, which may be modulated by activity in the slower oscillating larger network. The default network, also called the default mode network (DMN), default state network, or task-negative network, is one such network that is characterized by coherent neuronal oscillations at a rate lower than 0.1 Hz. Other large scale networks also have this slow-wave property, as described below [BUCKNER R L, Andrews-Hanna J R, Schacter D L. The brain's default network: anatomy, function, and relevance to disease. Ann N Y Acad Sci 1124(2008):1-38; PALVA J M, Palva S. Infra-slow fluctuations in electrophysiological recordings, blood-oxygenation-level-dependent signals, and psychophysical time series. Neuroimage 62(4, 2012):2201-2211; STEYN-ROSS M L, Steyn-Ross D A, Sleigh J W, Wilson M T. A mechanism for ultra-slow oscillations in the cortical default network. Bull Math Biol 73(2, 2011):398-416].

The default mode network corresponds to task-independent introspection (e.g., daydreaming), or self-referential thought. When the DMN is activated, the individual is ordinarily awake and alert, but the DMN may also be active during the early stages of sleep and during conscious sedation. During goal-oriented activity, the DMN is deactivated and one or more of several other networks, so-called task-positive networks (TPN), are activated. DMN activity is attenuated rather than extinguished during the transition between states, and is observed, albeit at lower levels, alongside task-specific activations. Strength of the DMN deactivation appears to be inversely related to the extent to which the task is demanding. Thus, DMN has been described as a task-negative network, given the apparent antagonism between its activation and task performance. The posterior cingulate cortex (PCC) and adjacent precuneus and the medial prefrontal cortex (mPFC) are the two most clearly delineated regions within the DMN [RAICHLE M E, Snyder A Z. A default mode of brain function: a brief history of an evolving idea. Neuroimage 37(4, 2007):1083-1090; BROYD S J, Demanuele C, Debener S, Helps S K, James C J, Sonuga-Barke E J. Default-mode brain dysfunction in mental disorders: a systematic review. Neurosci Biobehav Rev 33(3, 2009):279-96; BUCKNER R L, Andrews-Hanna J R, Schacter D L. The brain's default network: anatomy, function, and relevance to disease. Ann N Y Acad Sci 1124(2008):1-38; BUCKNER R L, Sepulcre J, Talukdar T, Krienen F M, Liu H, Hedden T, Andrews-Hanna J R, Sperling R A, Johnson K A. Cortical hubs revealed by intrinsic functional connectivity: mapping, assessment of stability, and relation to Alzheimer's disease. J Neurosci 29(2009):1860-1873; GREICIUS M D, Krasnow B, Reiss A L, Menon V. Functional connectivity in the resting brain: a network analysis of the default mode hypothesis. Proc Natl Acad Sci USA 100(2003): 253-258].

For autistic individuals, default mode network activity is abnormal, because it is uncommonly low at rest, with reduced connectivity between anterior and posterior regions of the network probably reflecting a disturbance of self-referential thought. Furthermore, the absence of an anti-correlation between the default mode network and task-positive networks suggests an imbalance in the toggling between networks, driven by a paucity of introspective thought in autistic individuals. The subcomponents within the default mode network of autistic individuals also appear to be very weakly connected to one another [BROYD S J, Demanuele C, Debener S, Helps S K, James C J, Sonuga-Barke E J. Default-mode brain dysfunction in mental disorders: a systematic review. Neurosci Biobehav Rev 33(3, 2009):279-296; CHERKASSKY V L, Kana R K, Keller T A, Just M A. Functional connectivity in a baseline resting-state network in autism. Neuroreport 17(16, 2006):1687-1690; ASSAF M, Jagannathan K, Calhoun V D, Miller L, Stevens M C, Sahl R, O'Boyle J G, Schultz R T, Pearlson G D. Abnormal functional connectivity of default mode sub-networks in autism spectrum disorder patients. Neuroimage 53(1, 2010):247-256; KENNEDY D P, Redcay E, Courchesne E. Failing to deactivate: resting functional abnormalities in autism. Proc Natl Acad Sci USA 103(21, 2006): 8275-8280].

The term low frequency resting state networks (LFRSN or simply RSN) is used to describe both the task-positive and task-negative networks. Using independent component analysis (ICA) and related methods to assess coherence of fMRI Blood Oxygenation Level Dependent Imaging (BOLD) signals in terms of temporal and spatial variation, as well as variations between individuals, low frequency resting state networks in addition to the DMN have been identified, corresponding to different tasks or states of mind. They are related to their underlying anatomical connectivity and replay at rest the patterns of functional activation evoked by the behavioral tasks. That is to say, brain regions that are commonly recruited during a task are anatomically connected and maintain in the resting state (in the absence of any stimulation) a significant degree of temporal coherence in their spontaneous activity, which is what allows them to be identified at rest [SMITH S M, Fox P T, Miller K L, Glahn D C, Fox P M, et al. Correspondence of the brain's functional architecture during activation and rest. Proc Natl Acad Sci USA 106(2009): 13040-13045].

Frequently reported resting state networks (RSNs), in addition to the default mode network, include the senso-rimotor RSN, the executive control RSN, up to three visual RSNs, two lateralized fronto-parietal RSNs, the auditory RSN and the temporo-parietal RSN. However, different investigators use different methods to identify the low frequency resting state networks, so different numbers and somewhat different identities of RSNs are reported by different investigators [COLE D M, Smith S M, Beckmann C F. Advances and pitfalls in the analysis and interpretation of resting-state FMRI data. Front Syst Neurosci 4(2010):8, pp. 1-15]. Examples of RSNs are described in publications cited by COLE and the following: ROSAZZA C, Minati L. Resting-state brain networks: literature review and clinical applications. Neurol Sci 32(5, 2011):773-85; ZHANG D, Raichle M E. Disease and the brain's dark energy. Nat Rev Neurol 6(1, 2010):15-28; DAMOISEAUX, J. S., Rombouts, S. A. R. B., Barkhof, F., Scheltens, P., Stam, C. J., Smith, S. M., Beckmann, C. F. Consistent resting-state networks across healthy subjects. Proc. Natl. Acad. Sci. U.S.A. 103 (2006): 13848-13853 FOX M D, Snyder A Z, Vincent J L, Corbetta M, Van Essen D C, Raichle M E. The human brain is intrinsically organized into dynamic, anticorrelated functional networks. Proc Natl Acad Sci USA 102(2005):9673-9678; LI R, Wu X, Chen K, Fleisher A S, Reiman E M, Yao L. Alterations of Directional Connectivity among Resting-State Networks in Alzheimer Disease. AJNR Am J Neuroradiol. 2012 Jul. 12. [Epub ahead of print, pp. 1-6].

For example, the dorsal attention network (DAN) and ventral attention network (VAN) are two networks responsible for attentional processing. The VAN is involved in involuntary actions and exhibits increased activity upon detection of salient targets, especially when they appear in unexpected locations (bottom-up activity, e.g. when an automobile driver unexpectedly senses a hazard or unexpected situation). The DAN is involved in voluntary (top-down) orienting and increases activity after presentation of cues indicating where, when, or to what individuals should direct their attention [FOX M D, Corbetta M, Snyder A Z, Vincent J L, Raichle M E. Spontaneous neuronal activity distinguishes human dorsal and ventral attention systems. Proc Natl Acad Sci USA 103(2006):10046-10051; WEN X, Yao L, Liu Y, Ding M. Causal interactions in attention networks predict behavioral performance. J Neurosci 32(4, 2012): 1284-1292]. The DAN is bilaterally centered in the intraparietal sulcus and the frontal eye field. The VAN is largely right lateralized in the temporal-parietal junction and the ventral frontal cortex.

The attention systems (e.g., VAN and DAN) have been investigated long before their identification as resting state networks, and functions attributed to the VAN have in the past been attributed to the locus ceruleus/noradrenaline system [ASTON-JONES G, Cohen J D. An integrative theory of locus coeruleus-norepinephrine function: adaptive gain and optimal performance. Annu Rev Neurosci 28(2005):403-50; BOURET S, Sara S J. Network reset: a simplified overarching theory of locus coeruleus noradrenaline function. Trends Neurosci 28(11, 2005):574-82; SARA S J, Bouret S. Orienting and Reorienting: The Locus Coeruleus Mediates Cognition through Arousal. Neuron 76(1, 2012):130-41; BERRIDGE C W, Waterhouse B D. The locus coeruleus-noradrenergic system: modulation of behavioral state and state-dependent cognitive processes. Brain Res Brain Res Rev 42(1, 2003):33-84].

The attention systems originally described by PETERSON and Posner are more expansive than just the VAN and DAN system, with interacting anatomical components corresponding to alerting, orienting, and executive control [PETERSEN S E, Posner M I. The attention system of the human brain: 20 years after. Annu Rev Neurosci 35(2012): 73-89]. In that description, DAN and VAN comprise significant portions of the orienting system, and components largely involving locus ceruleus-norepinephrine function comprise the alerting system. Other resting state networks are involved with executive control [BECKMANN C F, DeLuca M, Devlin J T, Smith S M. Investigations into resting-state connectivity using independent component analysis. Philos Trans R Soc Lond B Biol Sci 360(1457, 2005):1001-1013; JUST M A, Cherkassky V L, Keller T A, Kana R K, Minshew N J. Functional and anatomical cortical underconnectivity in autism: evidence from an FMRI study of an executive function task and corpus callosum morphometry. Cereb Cortex 17(4, 2007):951-961].

The alerting, orienting, and executive control systems, and presumably their constituent resting state networks, all appear to be abnormal in autistic individuals [KEEHN B, Müller R A, Townsend J. Atypical attentional networks and the emergence of autism. Neurosci Biobehav Rev 37(2, 2013):164-183].

MENON and colleagues describe the anterior insula as being at the heart of the ventral attention system [ECKERT M A, Menon V, Walczak A, Ahlstrom J, Denslow S, Horwitz A, Dubno J R. At the heart of the ventral attention system: the right anterior insula. Hum Brain Mapp 30(8, 2009): 2530-2541; MENON V, Uddin L Q. Saliency, switching, attention and control: a network model of insula function. Brain Struct Funct 214(5-6, 2010):655-667]. However, SEELEY and colleagues used region-of-interest and independent component analyses of resting-state fMRI data to demonstrate the existence of an independent brain network comprised of both the anterior insula and dorsal ACC, along with subcortical structures including the amygdala, substantia nigra/ventral tegmental area, and thalamus. This network is distinct from the other well-characterized large-scale brain networks, e.g. the default mode network [SEELEY W W, Menon V, Schatzberg A F, Keller J, Glover G H, Kenna H, et al. Dissociable intrinsic connectivity networks for salience processing and executive control. J Neurosci 2007; 27(9):2349-2356]. CAUDA and colleagues found that the human insula is functionally involved in two distinct neural networks: i) the anterior pattern is related to the ventralmost anterior insula, and is connected to the rostral anterior cingulate cortex, the middle and inferior frontal cortex, and the temporoparietal cortex; ii) the posterior pattern is associated with the dorsal posterior insula, and is connected to the dorsal-posterior cingulate, sensorimotor, premotor, supplementary motor, temporal cortex, and to some occipital areas [CAUDA F, D'Agata F, Sacco K, Duca S, Geminiani G, Vercelli A. Functional connectivity of the insula in the resting brain. Neuroimage 55(1, 2011):8-23; CAUDA F, Vercelli A. How many clusters in the insular cortex? Cereb Cortex. 2012 Sep. 30. (Epub ahead of print, pp. 1-2)]. TAYLOR and colleagues also report two such resting networks [TAYLOR K S, Seminowicz D A, Davis K D. Two systems of resting state connectivity between the insula and cingulate cortex. Hum Brain Mapp 30(9, 2009):2731-2745]. DEEN and colleagues found three such resting state networks [DEEN B, Pitskel N B, Pelphrey K A. Three systems of insular functional connectivity identified with cluster analysis. Cereb Cortex 21(7, 2011):1498-1506].

Resting state networks involving the insula, not necessarily part of the attention systems, also appear to be significantly abnormal in autistic individuals [UDDIN L Q, Menon V. The anterior insula in autism: under-connected and under-examined. Neurosci Biobehav Rev 33(8, 2009): 1198-1203; DI MARTINO A, Shehzad Z, Kelly C, Roy A K, Gee D G, Uddin L Q, Gotimer K, Klein D F, Castellanos F X, Milham M P. Relationship between cingulo-insular functional connectivity and autistic traits in neurotypical adults. Am J Psychiatry 166(8, 2009):891-899]. The amygdala is prominent in some such resting state networks, and its abnormality in autistic individuals is said to contribute to autistic behavior [von dem HAGEN E A, Stoyanova R S, Baron-Cohen S, Calder A J. Reduced functional connectivity within and between 'social' resting state networks in autism spectrum conditions. Soc Cogn Affect Neurosci. 2012 Jun. 8 (Epub ahead of print); KLEINHANS N M, Richards T, Sterling L, Stegbauer K C, Mahurin R, Johnson L C, Greenson J, Dawson G, Aylward E. Abnormal functional connectivity in autism spectrum disorders during face processing. Brain. 2008 April; 131(Pt 4):1000-1012; BARON-COHEN S, Ring H A, Bullmore E T, Wheelwright S, Ashwin C, Williams S C. The amygdala theory of autism. Neurosci Biobehav Rev 24(3, 2000):355-364].

Taken together, the publications cited above suggest that the default mode network as well as many other resting state networks may be abnormal in autistic individuals. In general, individual resting state autistic networks may have abnormally low activity, and the autistic individual may have difficulty deactivating one resting state network to activate another (toggling). The difficulty in deactivation may be a result of abnormally high local neuronal connectivity within a particular resting state network and a lack of connectivity between different networks. As a normal individual matures, there is a characteristic decrease in such local connectivity and an increase in long-range connectivity [DOSENBACH N U, Nardos B, Cohen A L, et al. Prediction of individual brain maturity using fMRI. Science 329(5997, 2010):1358-1361]. This maturation appears to be deficient in autistic individuals and has in fact given rise to a functional connectivity theory of autism [JUST M A, Keller T A, Malave V L, Kana R K, Varma S. Autism as a neural systems disorder: a theory of frontal-posterior underconnectivity. Neurosci Biobehav Rev 36(4, 2012):1292-1313; LEWIS J D, Elman J L. Growth-related neural reorganization and the autism phenotype: a test of the hypothesis that altered brain growth leads to altered connectivity. Dev Sci 11(1, 2008):135-155; MULLER R A. From loci to networks and back again: anomalies in the study of autism. Ann N Y Acad Sci 1145 (2008):300-315]. Some of the apparent local over-connectivity and long-range under-connectivity in autistic individuals may be an artifact of movement during measurement, especially in young children who are prone to movement. However, notwithstanding possible exaggeration of the connection abnormalities when the data are not properly scrubbed for head movement, the connectivity theory may serve as the basis of interventions involving vagus nerve stimulation as now described [MULLER R A, Shih P, Keehn B, Deyoe J R, Leyden K M, Shukla D K. Underconnected, but how? A survey of functional connectivity MRI studies in autism spectrum disorders. Cereb Cortex 21(10, 2011):2233-2243; Van DIJK K R, Sabuncu M R, Buckner R L. The influence of head motion on intrinsic functional connectivity MRI. Neuroimage 59(1, 2012):431-438; POWER J D, Barnes K A, Snyder A Z, Schlaggar B L, Petersen S E. Spurious but systematic correlations in functional connectivity MRI networks arise from subject motion. Neuroimage 59(3, 2012):2142-2154; SATTERTHWAITE T D, Wolf D H, Loughead J, Ruparel K, Elliott M A, Hakonarson H, Gur R C, Gur R E. Impact of in-scanner head motion on multiple measures of functional connectivity: relevance for studies of neurodevelopment in youth. Neuroimage 60(1, 2012):623-632].

Before disclosing methods for modulating resting state networks using vagal nerve stimulation, we first describe how stimulation of the vagus nerve can affect some of the most relevant components of the brain, such as the insula and amygdala (see FIG. 1). These structures are involved in the higher-level processing of sensory information, and that processing is often abnormal in autistic individuals. The sensory information consists not only of hearing, vision, taste & smell, and touch, but also other sensory modalities such as proprioception, nociception and interoception, and the problem that the autistic individuals experience is often not with the sensation per se, but with the integration of different sensory modalities and the association of sensory experience with affective and empathic processes. In other words, the autistic individual may not recognize that a sensation is salient, which a normal individual would act upon [MARCO E J, Hinkley L B, Hill S S, Nagarajan S S. Sensory processing in autism: a review of neurophysiologic findings. Pediatr Res 69(5 Pt 2, 2011):48R-54R; SEELEY W W, Menon V, Schatzberg A F, Keller J, Glover G H, Kenna H, Reiss A L, Greicius M D. Dissociable intrinsic connectivity networks for salience processing and executive control. J Neurosci 27(9, 2007):2349-2356; UDDIN L Q, Menon V. The anterior insula in autism: under-connected and under-examined. Neurosci Biobehav Rev 33(8, 2009): 1198-1203].

For purposes of illustration in FIG. 1, we use interoceptive neural pathways leading to the insula and amygdala (which are involved in the sensation of temperature, itch, and the like), because they have an inherent association with emotion [CRAIG A D. How do you feel—now? The anterior insula and human awareness. Nat Rev Neurosci 10(1, 2009): 59-70]. These pathways are said to be abnormal in autistic individuals [EBISCH S J, Gallese V, Willems R M, Mantini D, Groen W B, Romani G L, Buitelaar J K, Bekkering H. Altered intrinsic functional connectivity of anterior and posterior insula regions in high-functioning participants with autism spectrum disorder. Hum Brain Mapp 32(7, 2011):1013-1028]. Anatomically, interoceptive sensations are distinguished from surface touch (tactile) sensations by their association with the spinothalamic projection that ascend in the contralateral spinal cord, rather than with the dorsal column/medial lemniscal system which ascends the ipsilateral spinal cord. However, both contralateral and ipsilateral circuits are shown in the spinal cord in FIG. 1 to indicate that the discussion applies more generally to sensory processing, not just the interoception that is used for purposes of discussion.

Many neural circuits that are involved in interoception are located in higher regions of the central nervous system, but the invention can nevertheless electrically stimulate the vagus nerve in such a way as to modulate the activity of those neural circuits. They are shown in of FIG. 1 and described in paragraphs that follow [CRAIG A D. How do you feel? Interoception: the sense of the physiological condition of the body. Nat Rev Neurosci 3(8, 2002):655-666; BIELEFELDT K, Christianson J A, Davis B M. Basic and clinical aspects of visceral sensation: transmission in the CNS. Neurogastroenterol Motil 17(4, 2005):488-499; MAYER E A, Naliboff B D, Craig A D. Neuroimaging of the brain-gut axis: from basic understanding to treatment of functional GI disorders. Gastroenterology 131(6, 2006): 1925-1942].

Interoceptive sensations arise from signals sent by parasympathetic and sympathetic afferent nerves. The latter are considered to be the primary culprit for pain and other unpleasant emotional feelings, but parasympathetic afferents also contribute. Among afferents whose cell bodies are found in the dorsal root ganglia, the ones having type B cell bodies are most significant, which terminate in lamina I of the spinal and trigeminal dorsal horns. Other afferent nerves that terminate in the deep dorsal horn provide signals related to mechanoreceptive, proprioceptive and nociceptive activity.

Lamina I neurons project to many locations. First, they project to the sympathetic regions in the intermediomedial and intermediolateral cell columns of the thoracolumbar cord, where the sympathetic preganglionic cells of the autonomic nervous system originate (See FIG. 1). Second, in the medulla, lamina I neurons project to the A1 catecholaminergic cell groups of the ventrolateral medulla and then to sites in the rostral ventrolateral medulla (RVLM) which is interconnected with the sympathetic neurons that project to spinal levels. Only a limited number of discrete regions within the supraspinal central nervous system project to sympathetic preganglionic neurons in the intermediolateral column (see FIG. 1). The most important of these regions are the rostral ventral lateral medulla (RVLM), the rostral ventromedial medulla (RVMM), the midline raphe, the paraventricular nucleus (PVN) of the hypothalamus, the medullocervical caudal pressor area (mCPA), and the A5 cell group of the pons. The first four of these connections to the intermediolateral nucleus are shown in FIG. 1 [STRACK A M, Sawyer W B, Hughes J H, Platt K B, Loewy A D. A general pattern of CNS innervation of the sympathetic outflow demonstrated by transneuronal pseudorabies viral infections. Brain Res. 491(1, 1989): 156-162].

The rostral ventral lateral medulla (RVLM) is the primary regulator of the sympathetic nervous system, sending excitatory fibers (glutamatergic) to the sympathetic preganglionic neurons located in the intermediolateral nucleus of the spinal cord. Vagal afferents synapse in the NTS, and their projections reach the RVLM via the caudal ventrolateral medulla. However, resting sympathetic tone also comes from sources above the pons, from hypothalamic nuclei, various hindbrain and midbrain structures, as well as the forebrain and cerebellum, which synapse in the RVLM. Only the hypothalamic projection to the RVLM is shown in FIG. 1.

The RVLM shares its role as a primary regulator of the sympathetic nervous system with the rostral ventromedial medulla (RVMM) and medullary raphe. Differences in function between the RVLM versus RVMM/medullary raphe have been elucidated for cardiovascular control, but are not well characterized for gastrointestinal control. Differential control of the RVLM by the hypothalamus may also occur via circulating hormones such as vasopressin. The RVMM contains at least three populations of nitric oxide synthase neurons that send axons to innervate functionally similar sites in the NTS and nucleus ambiguous. Circuits connecting the RVMM and RVLM may be secondary, via the NTS and hypothalamus.

In the medulla, lamina I neurons also project another site, namely, to the A2 cell group of the nucleus of the solitary tract, which also receives direct parasympathetic (vagal and glossopharyngeal) afferent input. As indicated above, the nucleus of the solitary tract projects to many locations, including the parabrachial nucleus. In the pons and mesencephalon, lamina I neurons project to the periaqueductal grey (PAG), the main homeostatic brainstem motor site, and to the parabrachial nucleus. Sympathetic and parasympathetic afferent activity is integrated in the parabrachial nucleus. It in turn projects to the insular cortex by way of the ventromedial thalamic nucleus (VMb, also known as VPMpc). A direct projection from lamina I to the ventromedial nucleus (VMpo), and a direct projection from the nucleus tractus solitarius to the VMb, provide a rostrocaudally contiguous column that represents all contralateral homeostatic afferent input. They project topographically to the mid/posterior dorsal insula (See FIG. 1).

In humans, this cortical image is re-represented in the anterior insula on the same side of the brain. The parasympathetic activity is re-represented in the left (dominant) hemisphere, whereas the sympathetic activity is re-represented in the right (non-dominant) hemisphere. These re-representations provide the foundation for a subjective evaluation of interoceptive state, which is forwarded to the orbitofrontal cortex (See FIG. 1).

The right anterior insula is associated with subjective awareness of homeostatic emotions (e.g., visceral and somatic pain, temperature, sexual arousal, hunger, and thirst) as well as all emotions (e.g., anger, fear, disgust, sadness, happiness, trust, love, empathy, social exclusion). This region is intimately interconnected with the anterior cingulate cortex (ACC). Unpleasant sensations are directly correlated with ACC activation. The anterior cingulate cortex and insula are both strongly interconnected with the orbitofrontal cortex, amygdala, hypothalamus, and brainstem homeostatic regions, of which only a few connections are shown in FIG. 1.

Methods of the present invention comprise modulation of two target regions using vagus nerve stimulation. A first method directly targets the front end of the interoceptive pathways shown in FIG. 1 (nucleus tractus solitarius, area postrema, and dorsal motor nucleus). The second method targets the distal end of the interoceptive pathways (anterior insula and anterior cingulate cortex) and is the one associated with modulating the resting state networks that were summarized above.

According to the first method, electrical stimulation of A and B fibers alone of a vagus nerve causes increased inhibitory neurotransmitters in the brainstem, which in turn inhibits signals sent to the parabrachial nucleus, VMb and VMpo. The stimulation uses special devices and a special waveform (described below), which minimize effects involving C fibers that might produce unwanted side-effects. The electrical stimulation first affects the dorsal vagal complex, which is the major termination site of vagal afferent nerve fibers. The dorsal vagal complex consists of the area postrema (AP), the nucleus of the solitary tract (NTS) and the dorsal motor nucleus of the vagus. The AP projects to the NTS and dorsal motor nucleus of the vagus bilaterally. It also projects bilaterally to the parabrachial nucleus and receives direct afferent input from the vagus nerve. Thus, the area postrema is in a unique position to receive and modulate ascending interoceptive information and to influence autonomic outflow [PRICE C J, Hoyda T D, Ferguson A V. The area postrema: a brain monitor and integrator of systemic autonomic state. Neuroscientist 14(2, 2008):182-194].

Projections to and from the locus ceruleus are particularly significant in the present invention because they are also used in the second method that is described below. The vagus nerve transmits information to the locus ceruleus via the nucleus tractus solitarius (NTS), which has a direct projection to the dendritic region of the locus ceruleus. Other afferents to, and efferents from, the locus ceruleus are described by SARA et al, SAMUELS et al, and ASTON-JONES [SARA S J, Bouret S. Orienting and Reorienting: The Locus Coeruleus Mediates Cognition through Arousal. Neuron 76(1, 2012):130-41; SAMUELS E R, Szabadi E. Functional neuroanatomy of the noradrenergic locus coeruleus: its roles in the regulation of arousal and autonomic function part I: principles of functional organisation. Curr Neuropharmacol 6(3):235-53; SAMUELS, E. R., and Szabadi, E. Functional neuroanatomy of the noradrenergic locus coeruleus: its roles in the regulation of arousal and autonomic function part II: physiological and pharmacological manipulations and pathological alterations of locus coeruleus activity in humans. Curr. Neuropharmacol. 6(2008), 254-285; Gary ASTON-JONES. Norepinephrine. Chapter 4 (pp. 47-57) in: Neuropsychopharmacology: The Fifth Generation of Progress (Kenneth L. Davis, Dennis Charney, Joseph T. Coyle, Charles Nemeroff, eds.) Philadelphia: Lippincott Williams & Wilkins, 2002].

In addition to the NTS, the locus ceruleus receives input from the nucleus gigantocellularis and its neighboring nucleus paragigantocellularis, the prepositus hypoglossal nucleus, the paraventricular nucleus of the hypothalamus, Barrington's nucleus, the central nucleus of the amygdala, and prefrontal areas of the cortex. These same nuclei receive input from the NTS, such that stimulation of the vagus nerve may modulate the locus ceruleus via the NTS and a subsequent relay through these structures.

The locus ceruleus has widespread projections throughout the cortex [SAMUELS E R, Szabadi E. Functional neuroanatomy of the noradrenergic locus coeruleus: its roles in the regulation of arousal and autonomic function part I: principles of functional organisation. Curr Neuropharmacol 6 (3):235-53]. It also projects to subcortical regions, notably the raphe nuclei, which release serotonin to the rest of the brain. An increased dorsal raphe nucleus firing rate is thought to be secondary to an initial increased locus ceruleus firing rate from vagus nerve stimulation [Adrienne E. DORR and Guy Debonnelv. Effect of vagus nerve stimulation on serotonergic and noradrenergic transmission. J Pharmacol Exp Ther 318(2, 2006):890-898; MANTA S, Dong J, Debonnel G, Blier P. Enhancement of the function of rat serotonin and norepinephrine neurons by sustained vagus nerve stimulation. J Psychiatry Neurosci 34(4, 2009):272-80]. The locus ceruleus also has projections to autonomic nuclei, including the dorsal motor nucleus of the vagus, as shown in FIG. 1 [FUKUDA, A., Minami, T., Nabekura, J., Oomura, Y. The effects of noradrenaline on neurones in the rat dorsal motor nucleus of the vagus, in vitro. J. Physiol., 393 (1987): 213-231; MARTINEZ-PENA y Valenzuela, I., Rogers, R. C., Hermann, G. E., Travagli, R. A. (2004) Norepinephrine effects on identified neurons of the rat dorsal motor nucleus of the vagus. Am. J. Physiol. Gas-trointest. Liver Physiol., 286, G333-G339; TERHORST, G. J., Toes, G. J., Van Willigen, J. D. Locus coeruleus projections to the dorsal motor vagus nucleus in the rat. Neuroscience, 45(1991): 153-160].

The present invention modulates the activity of resting state networks via the locus ceruleus (or alternatively via another structure that has widespread projections), by electrically stimulating a vagus nerve. Stimulation of a network via the locus ceruleus may activate or deactivate a network, depending on the detailed configuration of adrenergic receptor subtypes within the network and their roles in enhancing or depressing neural activity within the network, as well as subsequent network-to-network interactions. It is presumed that the individual has already been evaluated so as to assess abnormality in his resting state networks. According to the invention, one key to preferential stimulation of a particular resting state network, such as the DMN or those involving the insula and ACC, is to use a vagus nerve stimulation signal that entrains to the signature EEG pattern of that network (see below and MANTINI D, Perrucci M G, Del Gratta C, Romani G L, Corbetta M. Electrophysiological signatures of resting state networks in the human brain. Proc Natl Acad Sci USA 104(32, 2007):13170-13175). By this EEG entrainment method, it may be possible to preferentially attenuate or deactivate, for example, the insula/ACC networks in an autistic patient. Activation of another network such as the VAN or DMN may also produce the same effect, via network-to-network interactions. Although the locus ceruleus is presumed to project to all of the resting networks, it is thought to project most strongly to the ventral attention network (VAN) [CORBETTA M, Patel G, Shulman G L. The reorienting system of the human brain: from environment to theory of mind. Neuron 58(3, 2008):306-24; MANTINI D, Corbetta M, Perrucci M G, Romani G L, Del Gratta C. Large-scale brain networks account for sustained and transient activity during target detection. Neuroimage 44(1, 2009):265-274]. Thus, deactivation of a particular network may also be attempted by activating another resting state network, because the brain switches between them. According to the invention, the activation or deactivation of a resting state network may be undertaken in a particular behavioral situation by stimulation of the vagus nerve whenever the activation or deactivation would be considered normal in the then-present behavioral context.

Figure 2A:
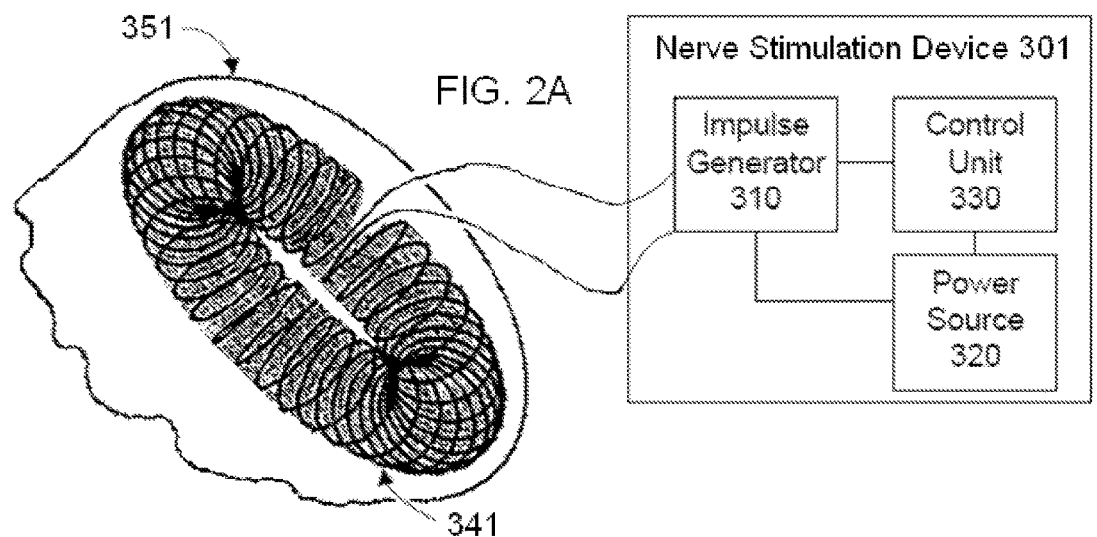
FIG. 2A is a schematic view of an exemplary nerve modulating device according to the present invention which supplies controlled pulses of electrical current to (A) a magnetic stimulator coil.

Description of the Magnetic and Electrode-Based Nerve Stimulating/Modulating Devices Devices of the invention that are used to stimulate a vagus nerve will now be described. Either a magnetic stimulation device or an electrode-based device may be used for that purpose. FIG. 2A is a schematic diagram of Applicant's magnetic nerve stimulating/modulating device 301 for delivering impulses of energy to nerves for the treatment of medical conditions such as autism spectrum disorders. As shown, device 301 may include an impulse generator 310; a power source 320 coupled to the impulse generator 310; a control unit 330 in communication with the impulse generator 310 and coupled to the power source 320; and a magnetic stimulator coil 341 coupled via wires to impulse generator coil 310. The stimulator coil 341 is toroidal in shape, due to its winding around a toroid of core material.

Although the magnetic stimulator coil 341 is shown in FIG. 2A to be a single coil, in practice the coil may also comprise two or more distinct coils, each of which is connected in series or in parallel to the impulse generator 310. Thus, the coil 341 that is shown in FIG. 2A represents all the magnetic stimulator coils of the device collectively. In a preferred embodiment that is discussed below, coil 341 actually contains two coils that may be connected either in series or in parallel to the impulse generator 310.

The item labeled in FIG. 2A as 351 is a volume, surrounding the coil 341, that is filled with electrically conducting medium. As shown, the medium not only encloses the magnetic stimulator coil, but is also deformable such that it is form-fitting when applied to the surface of the body. Thus, the sinuousness or curvature shown at the outer surface of the electrically conducting medium 351 corresponds also to sinuousness or curvature on the surface of the body, against which the conducting medium 351 is applied, so as to make the medium and body surface contiguous. As time-varying electrical current is passed through the coil 341, a magnetic field is produced, but because the coil winding is toroidal, the magnetic field is spatially restricted to the interior of the toroid. An electric field and eddy currents are also produced. The electric field extends beyond the toroidal space and into the patient's body, causing electrical currents and stimulation within the patient. The volume 351 is electrically connected to the patient at a target skin surface in order to significantly reduce the current passed through the coil 341 that is needed to accomplish stimulation of the patient's nerve or tissue. In a preferred embodiment of the magnetic stimulator that is discussed below, the conducting medium with which the coil 341 is in contact need not completely surround the toroid.

The design of the magnetic stimulator 301, which is also adapted herein for use with surface electrodes, makes it possible to shape the electric field that is used to selectively stimulate a relatively deep nerve such as a vagus nerve in the patient's neck. Furthermore, the design produces significantly less pain or discomfort (if any) to a patient, at the site of stimulation on the skin, than stimulator devices that are currently known in the art. Conversely, for a given amount of pain or discomfort on the part of the patient (e.g., the threshold at which such discomfort or pain begins), the design achieves a greater depth of penetration of the stimulus under the skin.

Figure 2B:
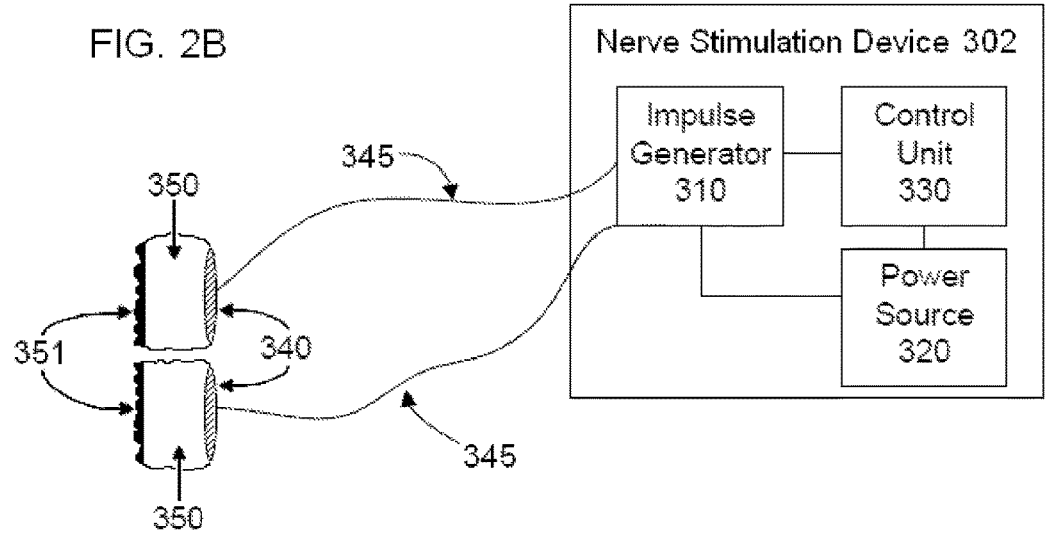
FIG. 2B is a schematic view of another embodiment of a nerve modulating device according to the present invention which supplies electrical current to surface electrodes.

An alternate embodiment of the present invention is shown in FIG. 2B, which is a schematic diagram of an electrode-based nerve stimulating/modulating device 302 for delivering impulses of energy to nerves for the treatment of medical conditions. As shown, device 302 may include an impulse generator 310; a power source 320 coupled to the impulse generator 310; a control unit 330 in communication with the impulse generator 310 and coupled to the power source 320; and electrodes 340 coupled via wires 345 to impulse generator 310. In a preferred embodiment, the same impulse generator 310, power source 320, and control unit 330 may be used for either the magnetic stimulator 301 or the electrode-based stimulator 302, allowing the user to change parameter settings depending on whether coils 341 or the electrodes 340 are attached.

Although a pair of electrodes 340 is shown in FIG. 2B, in practice the electrodes may also comprise three or more distinct electrode elements, each of which is connected in series or in parallel to the impulse generator 310. Thus, the electrodes 340 that are shown in FIG. 2B represent all electrodes of the device collectively.

The item labeled in FIG. 2B as 350 is a volume, contiguous with an electrode 340, that is filled with electrically conducting medium. As described below in connection with particular embodiments of the invention, conducting medium in which the electrode 340 is embedded need not completely surround an electrode. As also described below in connection with a preferred embodiment, the volume 350 is electrically connected to the patient at a target skin surface in order to shape the current density passed through an electrode 340 that is needed to accomplish stimulation of the patient's nerve or tissue. The electrical connection to the patient's skin surface is through an interface 351. In one embodiment, the interface is made of an electrically insulating (dielectric) material, such as a thin sheet of Mylar. In that case, electrical coupling of the stimulator to the patient is capacitive. In other embodiments, the interface comprises electrically conducting material, such as the electrically conducting medium 350 itself, or an electrically conducting or permeable membrane. In that case, electrical coupling of the stimulator to the patient is ohmic. As shown, the interface may be deformable such that it is form-fitting when applied to the surface of the body. Thus, the sinuousness or curvature shown at the outer surface of the interface 351 corresponds also to sinuousness or curvature on the surface of the body, against which the interface 351 is applied, so as to make the interface and body surface contiguous.

The control unit 330 controls the impulse generator 310 to generate a signal for each of the device's coils or electrodes. The signals are selected to be suitable for amelioration of a particular medical condition, when the signals are applied non-invasively to a target nerve or tissue via the coil 341 or electrodes 340. It is noted that nerve stimulating/modulating device 301 or 302 may be referred to by its function as a pulse generator. Patent application publications US2005/0075701 and US2005/0075702, both to SHAFER, contain descriptions of pulse generators that may be applicable to the present invention. By way of example, a pulse generator is also commercially available, such as Agilent 33522A Function/Arbitrary Waveform Generator, Agilent Technologies, Inc., 5301 Stevens Creek Blvd Santa Clara Calif. 95051.

The control unit 330 may also comprise a general purpose computer, comprising one or more CPU, computer memories for the storage of executable computer programs (including the system's operating system) and the storage and retrieval of data, disk storage devices, communication devices (such as serial and USB ports) for accepting external signals from the system's keyboard, computer mouse, and touchscreen, as well as any externally supplied physiological signals (see FIG. 8), analog-to-digital converters for digitizing externally supplied analog signals (see FIG. 8), communication devices for the transmission and receipt of data to and from external devices such as printers and modems that comprise part of the system, hardware for generating the display of information on monitors that comprise part of the system, and busses to interconnect the above-mentioned components. Thus, the user may operate the system by typing instructions for the control unit 330 at a device such as a keyboard and view the results on a device such as the system's computer monitor, or direct the results to a printer, modem, and/or storage disk. Control of the system may be based upon feedback measured from externally supplied physiological or environmental signals. Alternatively, the control unit 330 may have a compact and simple structure, for example, wherein the user may operate the system using only an on/off switch and power control wheel or knob.

Parameters for the nerve or tissue stimulation include power level, frequency and train duration (or pulse number). The stimulation characteristics of each pulse, such as depth of penetration, strength and selectivity, depend on the rise time and peak electrical energy transferred to the electrodes or coils, as well as the spatial distribution of the electric field that is produced by the electrodes or coils. The rise time and peak energy are governed by the electrical characteristics of the stimulator and electrodes or coils, as well as by the anatomy of the region of current flow within the patient. In one embodiment of the invention, pulse parameters are set in such as way as to account for the detailed anatomy surrounding the nerve that is being stimulated [Bartosz SAWICKI, Robert Szmurlo, Przemyslaw Plonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Pulses may be monophasic, biphasic or polyphasic. Embodiments of the invention include those that are fixed frequency, where each pulse in a train has the same interstimulus interval, and those that have modulated frequency, where the intervals between each pulse in a train can be varied.

Figure 2C:
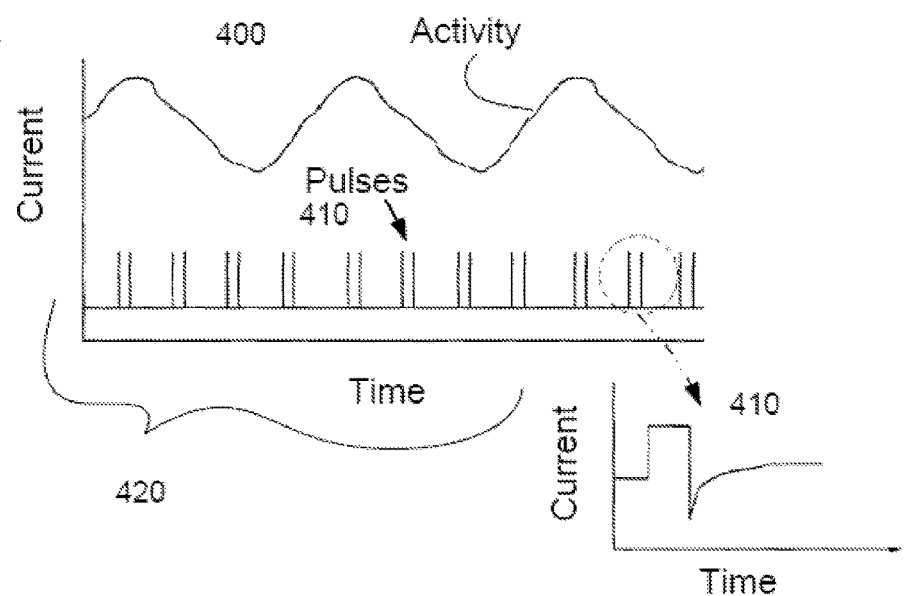
FIG. 2C illustrates an exemplary electrical voltage/current profile according to the present invention.

FIG. 2C illustrates an exemplary electrical voltage/current profile for a stimulating, blocking and/or modulating impulse applied to a portion or portions of selected nerves in accordance with an embodiment of the present invention. For the preferred embodiment, the voltage and current refer to those that are non-invasively produced within the patient by the stimulator coils or electrodes. As shown, a suitable electrical voltage/current profile 400 for the blocking and/or modulating impulse 410 to the portion or portions of a nerve may be achieved using pulse generator 310. In a preferred embodiment, the pulse generator 310 may be implemented using a power source 320 and a control unit 330 having, for instance, a processor, a clock, a memory, etc., to produce a pulse train 420 to the coil 341 or electrodes 340 that deliver the stimulating, blocking and/or modulating impulse 410 to the nerve. Nerve stimulating/modulating device 301 or 302 may be externally powered and/or recharged or may have its own power source 320. The parameters of the modulation signal 400, such as the frequency, amplitude, duty cycle, pulse width, pulse shape, etc., are preferably programmable. An external communication device may modify the pulse generator programming to improve treatment.

In addition, or as an alternative to the devices to implement the modulation unit for producing the electrical voltage/current profile of the stimulating, blocking and/or modulating impulse to the electrodes or coils, the device disclosed in patent publication No. US2005/0216062 may be employed. That patent publication discloses a multifunctional electrical stimulation (ES) system adapted to yield output signals for effecting electromagnetic or other forms of electrical stimulation for a broad spectrum of different biological and biomedical applications, which produce an electric field pulse in order to non-invasively stimulate nerves. The system includes an ES signal stage having a selector coupled to a plurality of different signal generators, each producing a signal having a distinct shape, such as a sine wave, a square or a saw-tooth wave, or simple or complex pulse, the parameters of which are adjustable in regard to amplitude, duration, repetition rate and other variables. Examples of the signals that may be generated by such a system are described in a publication by LIBOFF [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. The signal from the selected generator in the ES stage is fed to at least one output stage where it is processed to produce a high or low voltage or current output of a desired polarity whereby the output stage is capable of yielding an electrical stimulation signal appropriate for its intended application. Also included in the system is a measuring stage which measures and displays the electrical stimulation signal operating on the substance being treated, as well as the outputs of various sensors which sense prevailing conditions prevailing in this substance, whereby the user of the system can manually adjust the signal, or have it automatically adjusted by feedback, to provide an electrical stimulation signal of whatever type the user wishes, who can then observe the effect of this signal on a substance being treated.

The stimulating and/or modulating impulse signal 410 preferably has a frequency, an amplitude, a duty cycle, a pulse width, a pulse shape, etc. selected to influence the therapeutic result, namely, stimulating and/or modulating some or all of the transmission of the selected nerve. For example, the frequency may be about 1 Hz or greater, such as between about 15 Hz to 100 Hz, preferably between about 15-50 Hz and more preferably between about 15-35 Hz. In an exemplary embodiment, the frequency is 25 Hz. The modulation signal may have a pulse width selected to influence the therapeutic result, such as about 1 microseconds to about 1000 microseconds, preferably about 100-400 microseconds and more preferably about 200-400 microseconds. For example, the electric field induced or produced by the device within tissue in the vicinity of a nerve may be about 5 to 600 V/m, preferably less than 100 V/m, and even more preferably less than 30 V/m. The gradient of the electric field may be greater than 2 V/m/mm. More generally, the stimulation device produces an electric field in the vicinity of the nerve that is sufficient to cause the nerve to depolarize and reach a threshold for action potential propagation, which is approximately 8 V/m at 1000 Hz. The modulation signal may have a peak voltage amplitude selected to influence the therapeutic result, such as about 0.2 volts or greater, such as about 0.2 volts to about 40 volts, preferably between about 1-20 volts and more preferably between about 2-12 volts.

An objective of the disclosed stimulators is to provide both nerve fiber selectivity and spatial selectivity. Spatial selectivity may be achieved in part through the design of the electrode or coil configuration, and nerve fiber selectivity may be achieved in part through the design of the stimulus waveform, but designs for the two types of selectivity are intertwined. This is because, for example, a waveform may selectively stimulate only one of two nerves whether they lie close to one another or not, obviating the need to focus the stimulating signal onto only one of the nerves [GRILL W and Mortimer J T. Stimulus waveforms for selective neural stimulation. IEEE Eng. Med. Biol. 14 (1995): 375-385]. These methods complement others that are used to achieve selective nerve stimulation, such as the use of local anesthetic, application of pressure, inducement of ischemia, cooling, use of ultrasound, graded increases in stimulus intensity, exploiting the absolute refractory period of axons, and the application of stimulus blocks [John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

To date, the selection of stimulation waveform parameters for nerve stimulation has been highly empirical, in which the parameters are varied about some initially successful set of parameters, in an effort to find an improved set of parameters for each patient. A more efficient approach to selecting stimulation parameters might be to select a stimulation waveform that mimics electrical activity in the anatomical regions that one is attempting stimulate indirectly, in an effort to entrain the naturally occurring electrical waveform, as suggested in U.S. Pat. No. 6,234,953, entitled Electrotherapy device using low frequency magnetic pulses, to THOMAS et al. and application number US20090299435, entitled Systems and methods for enhancing or affecting neural stimulation efficiency and/or efficacy, to GLINER et al. One may also vary stimulation parameters iteratively, in search of an optimal setting [U.S. Pat. No. 7,869,885, entitled Threshold optimization for tissue stimulation therapy, to BEGNAUD et al]. However, some stimulation waveforms, such as those described herein, are discovered by trial and error, and then deliberately improved upon.

Invasive nerve stimulation typically uses square wave pulse signals. However, Applicant found that square waveforms are not ideal for non-invasive stimulation as they produce excessive pain. Prepulses and similar waveform modifications have been suggested as methods to improve selectivity of nerve stimulation waveforms, but Applicant did not find them ideal [Aleksandra VUCKOVIC, Marco Tosato and Johannes J Struijk. A comparative study of three techniques for diameter selective fiber activation in the vagal nerve: anodal block, depolarizing prepulses and slowly rising pulses. J. Neural Eng. 5 (2008): 275-286; Aleksandra VUCKOVIC, Nico J. M. Rijkhoff, and Johannes J. Struijk. Different Pulse Shapes to Obtain Small Fiber Selective Activation by Anodal Blocking—A Simulation Study. IEEE Transactions on Biomedical Engineering 51(5, 2004):698-706; Kristian HENNINGS. Selective Electrical Stimulation of Peripheral Nerve Fibers: Accommodation Based Methods. Ph.D. Thesis, Center for Sensory-Motor Interaction, Aalborg University, Aalborg, Denmark, 2004].

Figure 2D:
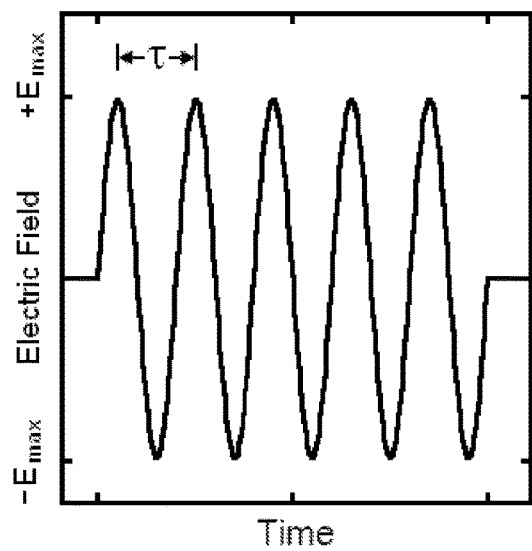
FIG. 2D illustrates an exemplary waveform for stimulating and/or modulating impulses that are applied to a nerve.
Figure 2E:
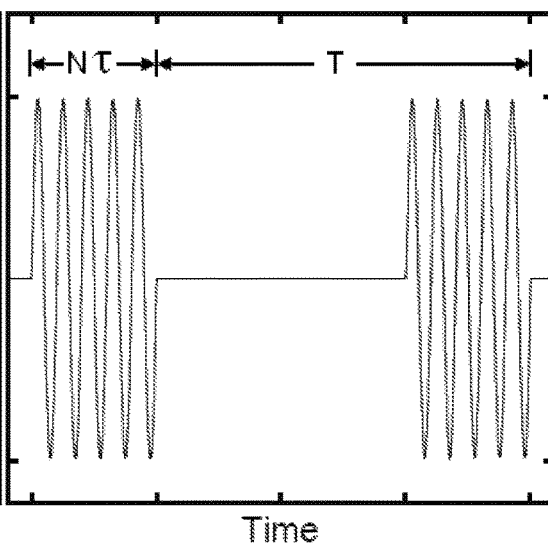
FIG. 2E illustrates another exemplary waveform for stimulating and/or modulating impulses applied to a nerve.

Applicant also found that stimulation waveforms consisting of bursts of square pulses are not ideal for non-invasive stimulation [M. I. JOHNSON, C. H. Ashton, D. R. Bousfield and J. W. Thompson. Analgesic effects of different pulse patterns of transcutaneous electrical nerve stimulation on cold-induced pain in normal subjects. Journal of Psychosomatic Research 35 (2/3, 1991):313-321; U.S. Pat. No. 7,734,340, entitled Stimulation design for neuromodulation, to De Ridder]. However, bursts of sinusoidal pulses are a preferred stimulation waveform, as shown in FIGS. 2D and 2E. As seen there, individual sinusoidal pulses have a period of, and a burst consists of N such pulses. This is followed by a period with no signal (the inter-burst period). The pattern of a burst followed by silent inter-burst period repeats itself with a period of T. For example, the sinusoidal period may be between about 50-1000 microseconds (equivalent to about 1-20 KHz), preferably between about 100-400 microseconds (equivalent to about 2.5-10 KHz), more preferably about 133-400 microseconds (equivalent to about 2.5-7.5 KHZ) and even more preferably about 200 microseconds (equivalent to about 5 KHz); the number of pulses per burst may be N=1-20, preferably about 2-10 and more preferably about 5; and the whole pattern of burst followed by silent inter-burst period may have a period T comparable to about 10-100 Hz, preferably about 15-50 Hz, more preferably about 25-35 Hz and even more preferably about 25 Hz (a much smaller value of T is shown in FIG. 2E to make the bursts discernable). When these exemplary values are used for T and, the waveform contains significant Fourier components at higher frequencies (1/200 microseconds=5000/sec), as compared with those contained in transcutaneous nerve stimulation waveforms, as currently practiced.

Applicant is unaware of such a waveform having been used with vagus nerve stimulation, but a similar waveform has been used to stimulate muscle as a means of increasing muscle strength in elite athletes. However, for the muscle strengthening application, the currents used (200 mA) may be very painful and two orders of magnitude larger than what are disclosed herein. Furthermore, the signal used for muscle strengthening may be other than sinusoidal (e.g., triangular), and the parameters, N, and T may also be dissimilar from the values exemplified above [A. DELITTO, M. Brown, M. J. Strube, S. J. Rose, and R. C. Lehman. Electrical stimulation of the quadriceps femoris in an elite weight lifter: a single subject experiment. Int J Sports Med 10(1989):187-191; Alex R WARD, Nataliya Shkuratova. Russian Electrical Stimulation The Early Experiments. Physical Therapy 82 (10, 2002): 1019-1030; Yocheved LAUFER and Michal Elboim. Effect of Burst Frequency and Duration of Kilohertz-Frequency Alternating Currents and of Low-Frequency Pulsed Currents on Strength of Contraction, Muscle Fatigue, and Perceived Discomfort. Physical Therapy 88 (10, 2008):1167-1176; Alex R WARD. Electrical Stimulation Using Kilohertz-Frequency Alternating Current. Physical Therapy 89 (2, 2009):181-190; J. PETROFSKY, M. Laymon, M. Prowse, S. Gunda, and J. Batt. The transfer of current through skin and muscle during electrical stimulation with sine, square, Russian and interferential waveforms. Journal of Medical Engineering and Technology 33 (2, 2009): 170-181; U.S. Pat. No. 4,177,819, entitled Muscle stimulating apparatus, to KOFSKY et al]. Burst stimulation has also been disclosed in connection with implantable pulse generators, but wherein the bursting is characteristic of the neuronal firing pattern itself [U.S. Pat. No. 7,734,340 to DE RIDDER, entitled Stimulation design for neuromodulation; application US20110184486 to DE RIDDER, entitled Combination of tonic and burst stimulations to treat neurological disorders]. By way of example, the electric field shown in FIGS. 2D and 2E may have an $E_{max}$ value of 17 V/m, which is sufficient to stimulate the nerve but is significantly lower than the threshold needed to stimulate surrounding muscle.

High frequency electrical stimulation is also known in the treatment of back pain at the spine [Patent application US20120197369, entitled Selective high frequency spinal cord modulation for inhibiting pain with reduced side effects and associated systems and methods, to ALATARIS et al.; Adrian AL KAISY, Iris Smet, and Jean-Pierre Van Buyten. Analgeia of axial low back pain with novel spinal neuromodulation. Poster presentation #202 at the 2011 meeting of The American Academy of Pain Medicine, held in National Harbor, Md., Mar. 24-27, 2011]. Those methods involve high-frequency modulation in the range of from about 1.5 KHz to about 50 KHz, which is applied to the patient's spinal cord region. However, such methods are different from the present invention because, for example, they is invasive; they do not involve a bursting waveform, as in the present invention; they necessarily involve A-delta and C nerve fibers and the pain that those fibers produce, whereas the present invention does not; they may involve a conduction block applied at the dorsal root level, whereas the present invention may stimulate action potentials without blocking of such action potentials; and/or they involve an increased ability of high frequency modulation to penetrate through the cerebral spinal fluid, which is not relevant to the present invention. In fact, a likely explanation for the reduced back pain that is produced by their use of frequencies from 10 to 50 KHz is that the applied electrical stimulus at those frequencies causes permanent damage to the pain-causing nerves, whereas the present invention involves only reversible effects [LEE R C, Zhang D, Hannig J. Biophysical injury mechanisms in electrical shock trauma. Annu Rev Biomed Eng 2 (2000):477-509].

Consider now which nerve fibers may be stimulated by the non-invasive vagus nerve stimulation. The waveform disclosed in FIG. 2 contains significant Fourier components at high frequencies (e.g., 1/200 microseconds=5000/sec), even if the waveform also has components at lower frequencies (e.g., 25/sec). Transcutaneously, A-beta, A-delta, and C fibers are typically excited at 2000 Hz, 250 Hz, and 5 Hz, respectively, i.e., the 2000 Hz stimulus is described as being specific for measuring the response of A-beta fibers, the 250 Hz for A-delta fibers, and the 5 Hz for type C fibers [George D. BAQUIS et al. TECHNOLOGY REVIEW: THE NEUROMETER CURRENT PERCEPTION THRESHOLD (CPT). Muscle Nerve 22(Supplement 8, 1999): S247-S259]. Therefore, the high frequency component of the noninvasive stimulation waveform will preferentially stimulate the A-alpha and A-beta fibers, and the C fibers will be largely unstimulated.

However, the threshold for activation of fiber types also depends on the amplitude of the stimulation, and for a given stimulation frequency, the threshold increases as the fiber size decreases. The threshold for generating an action potential in nerve fibers that are impaled with electrodes is traditionally described by Lapicque or Weiss equations, which describe how together the width and amplitude of stimulus pulses determine the threshold, along with parameters that characterize the fiber (the chronaxy and rheobase). For nerve fibers that are stimulated by electric fields that are applied externally to the fiber, as is the case here, characterizing the threshold as a function of pulse amplitude and frequency is more complicated, which ordinarily involves the numerical solution of model differential equations or a case-by-case experimental evaluation [David BOINAGROV, Jim Loudin and Daniel Palanker. Strength-Duration Relationship for Extracellular Neural Stimulation: Numerical and Analytical Models. J Neurophysiol 104(2010):2236-2248].

For example, REILLY describes a model (the spatially extended nonlinear nodal model or SENN model) that may be used to calculate minimum stimulus thresholds for nerve fibers having different diameters [J. Patrick REILLY. Electrical models for neural excitation studies. Johns Hopkins APL Technical Digest 9(1, 1988): 44-59]. According to REILLY's analysis, the minimum threshold for excitation of myelinated A fibers is 6.2 V/m for a 20 m diameter fiber, 12.3 V/m for a 10 m fiber, and 24.6 V/m for a 5 m diameter fiber, assuming a pulse width that is within the contemplated range of the present invention (1 ms). It is understood that these thresholds may differ slightly from those produced by the waveform of the present invention as illustrated by REILLY's figures, for example, because the present invention prefers to use sinusoidal rather than square pulses. Thresholds for B and C fibers are respectively 2 to 3 and 10 to 100 times greater than those for A fibers [Mark A. CASTORO, Paul B. Yoo, Juan G. Hincapie, Jason J. Hamann, Stephen B. Ruble, Patrick D. Wolf, Warren M. Grill. Excitation properties of the right cervical vagus nerve in adult dogs. Experimental Neurology 227 (2011): 62-68]. If we assume an average A fiber threshold of 15 V/m, then B fibers would have thresholds of 30 to 45 V/m and C fibers would have thresholds of 150 to 1500 V/m. The present invention produces electric fields at the vagus nerve in the range of about 6 to 100 V/m, which is therefore generally sufficient to excite all myelinated A and B fibers, but not the unmyelinated C fibers. In contrast, invasive vagus nerve stimulators that have been used for the treatment of epilepsy have been reported to excite C fibers in some patients [EVANS M S, Verma-Ahuja S, Naritoku D K, Espinosa J A. Intraoperative human vagus nerve compound action potentials. Acta Neurol Scand 110(2004): 232-238].

It is understood that although devices of the present invention may stimulate A and B nerve fibers, in practice they may also be used so as not to stimulate the largest A fibers (A-delta) and B fibers. In particular, if the stimulator amplitude has been increased to the point at which unwanted side effects begin to occur, the operator of the device may simply reduce the amplitude to avoid those effects. For example, vagal efferent fibers responsible for bronchoconstriction have been observed to have conduction velocities in the range of those of B fibers. In those experiments, bronchoconstriction was only produced when B fibers were activated, and became maximal before C fibers had been recruited [R. M. McALLEN and K. M. Spyer. Two types of vagal preganglionic motoneurones projecting to the heart and lungs. J. Physiol. 282(1978): 353-364]. Because proper stimulation with the disclosed devices does not result in the side-effect of bronchoconstriction, evidently the bronchoconstrictive B-fibers are possibly not being activated when the amplitude is properly set. Also, the absence of bradycardia or prolongation of PR interval suggests that cardiac efferent B-fibers are not stimulated. Similarly, A-delta afferents may behave physiologically like C fibers. Because stimulation with the disclosed devices does not produce nociceptive effects that would be produced by jugular A-delta fibers or C fibers, evidently the A-delta fibers may not be stimulated when the amplitude is properly set.

To summarize the foregoing discussion, the delivery, in a patient suffering from autism spectrum disorders, of an impulse of energy sufficient to stimulate and/or modulate transmission of signals of vagus nerve fibers will result in improved excitation-inhibition balance and more normal activity within higher centers of the brain (e.g., interoception), many of which are components of resting state networks. The most likely mechanisms do not involve the stimulation of C fibers; and the stimulation of afferent nerve fibers activates neural pathways causes the release of norepinephrine, and/or serotonin and/or GABA.

Figure 8:
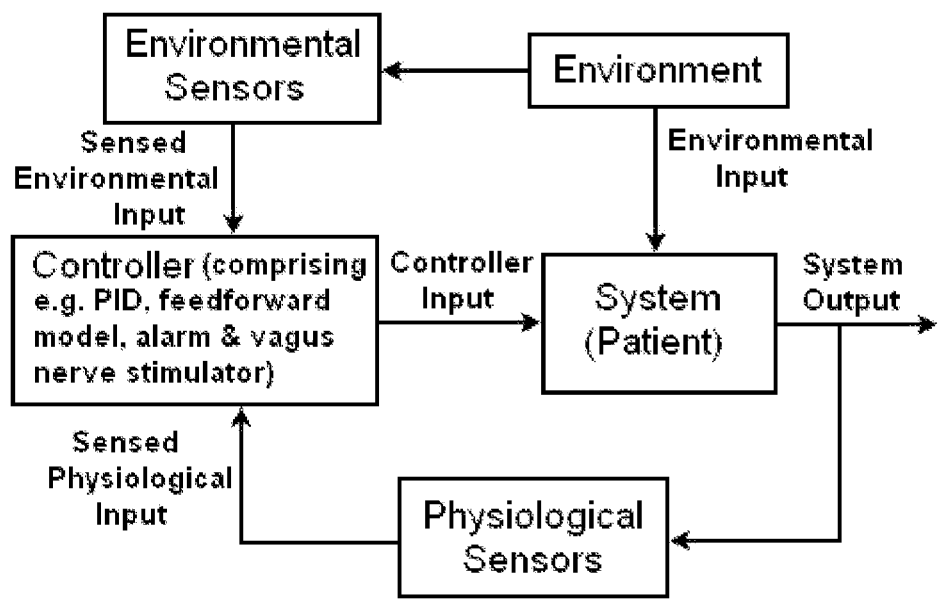
FIG. 8 illustrates connections between the controller and controlled system according to the present invention, their input and output signals, and external signals from the environment.

The use of feedback to generate the modulation signal 400 may result in a signal that is not periodic, particularly if the feedback is produced from sensors that measure naturally occurring, time-varying aperiodic physiological signals from the patient (see FIG. 8). In fact, the absence of significant fluctuation in naturally occurring physiological signals from a patient is ordinarily considered to be an indication that the patient is in ill health. This is because a pathological control system that regulates the patient's physiological variables may have become trapped around only one of two or more possible steady states and is therefore unable to respond normally to external and internal stresses. Accordingly, even if feedback is not used to generate the modulation signal 400, it may be useful to artificially modulate the signal in an aperiodic fashion, in such a way as to simulate fluctuations that would occur naturally in a healthy individual. Thus, the noisy modulation of the stimulation signal may cause a pathological physiological control system to be reset or undergo a non-linear phase transition, through a mechanism known as stochastic resonance [B. SUKI, A. Alencar, M. K. Sujeer, K. R. Lutchen, J. J. Collins, J. S. Andrade, E. P. Ingenito, S. Zapperi, H. E. Stanley, Life-support system benefits from noise, Nature 393 (1998) 127-128; W Alan C MUTCH, M Ruth Graham, Linda G Girling and John F Brewster. Fractal ventilation enhances respiratory sinus arrhythmia. Respiratory Research 2005, 6:41, pp. 1-9].

So, in one embodiment of the present invention, the modulation signal 400, with or without feedback, will stimulate the selected nerve fibers in such a way that one or more of the stimulation parameters (power, frequency, and others mentioned herein) are varied by sampling a statistical distribution having a mean corresponding to a selected, or to a most recent running-averaged value of the parameter, and then setting the value of the parameter to the randomly sampled value. The sampled statistical distributions will comprise Gaussian and 1/f, obtained from recorded naturally occurring random time series or by calculated formula. Parameter values will be so changed periodically, or at time intervals that are themselves selected randomly by sampling another statistical distribution, having a selected mean and coefficient of variation, where the sampled distributions comprise Gaussian and exponential, obtained from recorded naturally occurring random time series or by calculated formula.

In another embodiment, devices in accordance with the present invention are provided in a "pacemaker" type form, in which electrical impulses 410 are generated to a selected region of the nerve by a stimulator device on an intermittent basis, to create in the patient a lower reactivity of the nerve.

Preferred Embodiments of the Magnetic Stimulator

A preferred embodiment of magnetic stimulator coil 341 comprises a toroidal winding around a core consisting of high-permeability material (e.g., Supermendur), embedded in an electrically conducting medium. Toroidal coils with high permeability cores have been theoretically shown to greatly reduce the currents required for transcranial (TMS) and other forms of magnetic stimulation, but only if the toroids are embedded in a conducting medium and placed against tissue with no air interface [Rafael CARBUNARU and Dominique M. Durand. Toroidal coil models for transcutaneous magnetic stimulation of nerves. IEEE Transactions on Biomedical Engineering 48 (4, 2001): 434-441; Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, (UMI Microform Number: 9940153, UMI Company, Ann Arbor Mich.)].

Although Carbunaru and Durand demonstrated that it is possible to electrically stimulate a patient transcutaneously with such a device, they made no attempt to develop the device in such a way as to generally shape the electric field that is to stimulate the nerve. In particular, the electric fields that may be produced by their device are limited to those that are radially symmetric at any given depth of stimulation into the patient (i.e, z and are used to specify location of the field, not x, y, and z). This is a significant limitation, and it results in a deficiency that was noted in FIG. 6 of their publication: "at large depths of stimulation, the threshold current [in the device's coil] for long axons is larger than the saturation current of the coil. Stimulation of those axons is only possible at low threshold points such as bending sites or tissue conductivity inhomogeneities". Thus, for their device, varying the parameters that they considered, in order to increase the electric field or its gradient in the vicinity of a nerve, may come at the expense of limiting the field's physiological effectiveness, such that the spatial extent of the field of stimulation may be insufficient to modulate the target nerve's function. Yet, such long axons are precisely what we may wish to stimulate in therapeutic interventions, such as the ones disclosed herein.

Accordingly, it is an objective of the present invention to shape an elongated electric field of effect that can be oriented parallel to such a long nerve. The term "shape an electric field" as used herein means to create an electric field or its gradient that is generally not radially symmetric at a given depth of stimulation in the patient, especially a field that is characterized as being elongated or finger-like, and especially also a field in which the magnitude of the field in some direction may exhibit more than one spatial maximum (i.e. may be bimodal or multimodal) such that the tissue between the maxima may contain an area across which induced current flow is restricted. Shaping of the electric field refers both to the circumscribing of regions within which there is a significant electric field and to configuring the directions of the electric field within those regions. The shaping of the electric field is described in terms of the corresponding field equations in commonly assigned application US20110125203 (application Ser. No. 12/964,050), entitled Magnetic stimulation devices and methods of therapy, to SIMON et al., which is hereby incorporated by reference.

Thus, the present invention differs from the device disclosed by CARBUNARU and Durand by deliberately shaping an electric field that is used to transcutaneously stimulate the patient. Whereas the toroid in the CARBUNARU and Durand publication was immersed in a homogeneous conducting half-space, this is not necessarily the case for our invention. Although our invention will generally have some continuously conducting path between the device's coil and the patient's skin, the conducting medium need not totally immerse the coil, and there may be insulating voids within the conducting medium. For example, if the device contains two toroids, conducting material may connect each of the toroids individually to the patient's skin, but there may be an insulating gap (from air or some other insulator) between the surfaces at which conducting material connected to the individual toroids contact the patient. Furthermore, the area of the conducting material that contacts the skin may be made variable, by using an aperture adjusting mechanism such as an iris diaphragm. As another example, if the coil is wound around core material that is laminated, with the core in contact with the device's electrically conducting material, then the lamination may be extended into the conducting material in such a way as to direct the induced electrical current between the laminations and towards the surface of the patient's skin. As another example, the conducting material may pass through apertures in an insulated mesh before contacting the patient's skin, creating thereby an array of electric field maxima.

In the dissertation cited above, Carbunaru-FAIERSTEIN made no attempt to use conducting material other than agar in a KCl solution, and he made no attempt to devise a device that could be conveniently and safely applied to a patient's skin, at an arbitrary angle without the conducting material spilling out of its container. It is therefore an objective of the present invention to disclose conducting material that can be used not only to adapt the conductivity of the conducting material and select boundary conditions, thereby shaping the electric fields and currents as described above, but also to create devices that can be applied practically to any surface of the body. The volume of the container containing electrically conducting medium is labeled in FIG. 2A as 351. Use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. This allows for minimal heating of the coil(s) and deeper tissue stimulation. However, application of the conducting medium to the surface of the patient is difficult to perform in practice because the tissue contours (head, arms, legs, neck, etc.) are not planar. To solve this problem, in the preferred embodiment of the present invention, the toroidal coil is embedded in a structure which is filled with a conducting medium having approximately the same conductivity as muscle tissue, as now described.

In one embodiment of the invention, the container contains holes so that the conducting material (e.g., a conducting gel) can make physical contact with the patient's skin through the holes. For example, the conducting medium 351 may comprise a chamber surrounding the coil, filled with a conductive gel that has the approximate viscosity and mechanical consistency of gel deodorant (e.g., Right Guard Clear Gel from Dial Corporation, 15501 N. Dial Boulevard, Scottsdale Ariz. 85260, one composition of which comprises aluminum chlorohydrate, sorbitol, propylene glycol, polydimethylsiloxanes Silicon oil, cyclomethicone, ethanol/SD Alcohol 40, dimethicone copolyol, aluminum zirconium tetrachlorohydrex gly, and water). The gel, which is less viscous than conventional electrode gel, is maintained in the chamber with a mesh of openings at the end where the device is to contact the patient's skin. The gel does not leak out, and it can be dispensed with a simple screw driven piston.

In another embodiment, the container itself is made of a conducting elastomer (e.g., dry carbon-filled silicone elastomer), and electrical contact with the patient is through the elastomer itself, possibly through an additional outside coating of conducting material. In some embodiments of the invention, the conducting medium may be a balloon filled with a conducting gel or conducting powders, or the balloon may be constructed extensively from deformable conducting elastomers. The balloon conforms to the skin surface, removing any air, thus allowing for high impedance matching and conduction of large electric fields in to the tissue. A device such as that disclosed in U.S. Pat. No. 7,591,776, entitled Magnetic stimulators and stimulating coils, to PHILLIPS et al. may conform the coil itself to the contours of the body, but in the preferred embodiment, such a curved coil is also enclosed by a container that is filled with a conducting medium that deforms to be contiguous with the skin.

Agar can also be used as part of the conducting medium, but it is not preferred, because agar degrades in time, is not ideal to use against skin, and presents difficulties with cleaning the patient and stimulator coil. Use of agar in a 4M KCl solution as a conducting medium was mentioned in the above-cited dissertation: Rafael Carbunaru FAIERSTEIN, Coil Designs for Localized and Efficient Magnetic Stimulation of the Nervous System. Ph.D. Dissertation, Department of Biomedical Engineering, Case Western Reserve, May, 1999, page 117 (UMI Microform Number: 9940153, UMI Company, Ann Arbor Mich.). However, that publication makes no mention or suggestion of placing the agar in a conducting elastomeric balloon, or other deformable container so as to allow the conducting medium to conform to the generally non-planar contours of a patient's skin having an arbitrary orientation. In fact, that publication describes the coil as being submerged in a container filled with an electrically conducting solution. If the coil and container were placed on a body surface that was oriented in the vertical direction, then the conducting solution would spill out, making it impossible to stimulate the body surface in that orientation. In contrast, the present invention is able to stimulate body surfaces having arbitrary orientation.

That dissertation also makes no mention of a dispensing method whereby the agar would be made contiguous with the patient's skin. A layer of electrolytic gel is said to have been applied between the skin and coil, but the configuration was not described clearly in the publication. In particular, no mention is made of the electrolytic gel being in contact with the agar.

Rather than using agar as the conducting medium, the coil can instead be embedded in a conducting solution such as 1-10% NaCl, contacting an electrically conducting interface to the human tissue. Such an interface is used as it allows current to flow from the coil into the tissue and supports the medium-surrounded toroid so that it can be completely sealed. Thus, the interface is material, interposed between the conducting medium and patient's skin, that allows the conducting medium (e.g., saline solution) to slowly leak through it, allowing current to flow to the skin. Several interfaces are disclosed as follows.

One interface comprises conducting material that is hydrophilic, such as Tecophlic from The Lubrizol Corporation, 29400 Lakeland Boulevard, Wickliffe, Ohio 44092. It absorbs from 10-100% of its weight in water, making it highly electrically conductive, while allowing only minimal bulk fluid flow.

Another material that may be used as an interface is a hydrogel, such as that used on standard EEG, EKG and TENS electrodes [Rylie A GREEN, Sungchul Baek, Laura A Poole-Warren and Penny J. Martens. Conducting polymer-hydrogels for medical electrode applications. Sci. Technol. Adv. Mater. 11 (2010) 014107 (13 pp)]. For example it may be the following hypoallergenic, bacteriostatic electrode gel: SIGNAGEL Electrode Gel from Parker Laboratories, Inc., 286 Eldridge Rd., Fairfield N.J. 07004.

A third type of interface may be made from a very thin material with a high dielectric constant, such as those used to make capacitors. For example, Mylar can be made in submicron thicknesses and has a dielectric constant of about 3. Thus, at stimulation frequencies of several kilohertz or greater, the Mylar will capacitively couple the signal through it because it will have an impedance comparable to that of the skin itself. Thus, it will isolate the toroid and the solution it is embedded in from the tissue, yet allow current to pass.

The preferred embodiment of the magnetic stimulator coil 341 in FIG. 2A reduces the volume of conducting material that must surround a toroidal coil, by using two toroids, side-by-side, and passing electrical current through the two toroidal coils in opposite directions. In this configuration, the induced current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain other peripheral nerves.

This preferred embodiment of the magnetic stimulation device is shown in FIG. 3. FIGS. 3A and 3B respectively provide top and bottom views of the outer surface of the toroidal magnetic stimulator 30. FIGS. 3C and 3D respectively provide top and bottom views of the toroidal magnetic stimulator 30, after sectioning along its long axis to reveal the inside of the stimulator.

FIGS. 3A-3D all show a mesh 31 with openings that permit a conducting gel to pass from the inside of the stimulator to the surface of the patient's skin at the location of nerve or tissue stimulation. Thus, the mesh with openings 31 is the part of the stimulator that is applied to the skin of the patient.

Figure 3A:
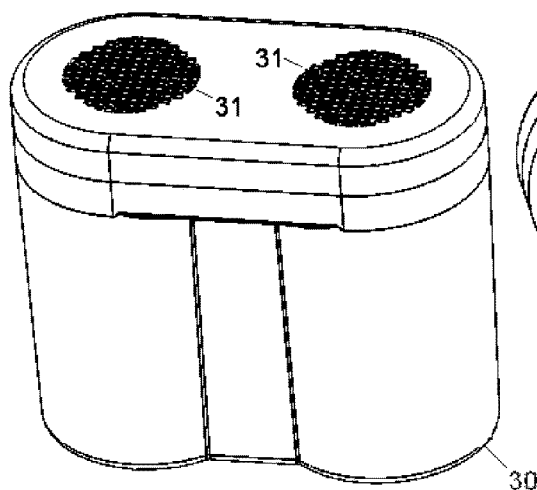
FIG. 3A is a perspective view of the top of a dual-toroid magnetic stimulator coil according to an embodiment of the present invention.
Figure 3B:
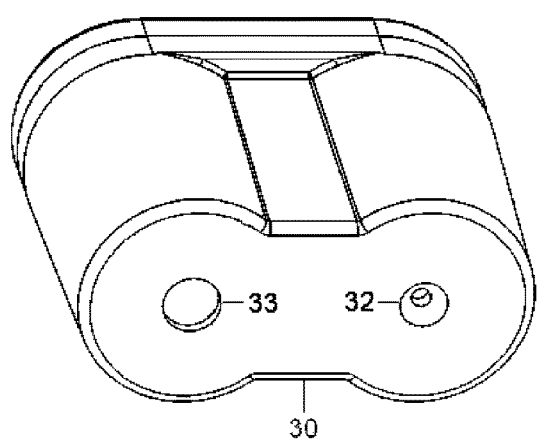
FIG. 3B is a perspective view of the bottom of the magnetic stimulator coil of FIG. 3A.
Figure 3C:
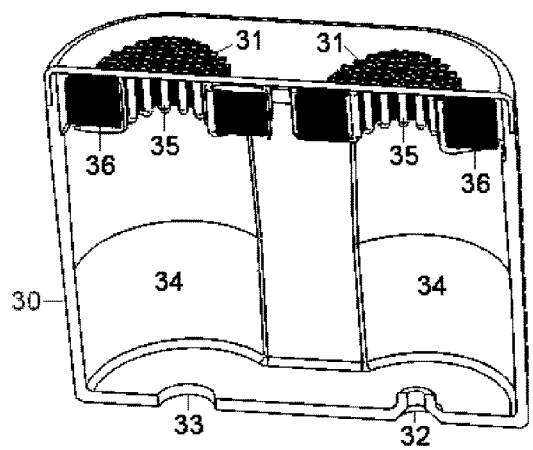
FIG. 3C is a cut-a-way view of the magnetic stimulator coil of FIG. 3A.
Figure 3D:
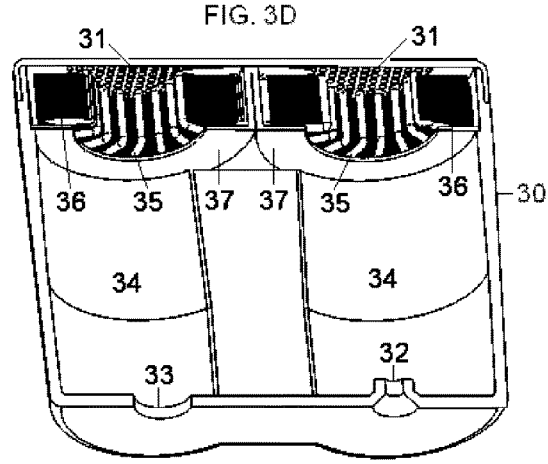
FIG. 3D is another cut-a-way view of the magnetic stimulator coil of FIG. 3A.

FIGS. 3B-3D show openings at the opposite end of the stimulator 30. One of the openings is an electronics port 32 through which wires pass from the stimulator coil(s) to the impulse generator (310 in FIG. 2A). The second opening is a conducting gel port 33 through which conducting gel may be introduced into the stimulator 30 and through which a screw-driven piston arm may be introduced to dispense conducting gel through the mesh 31. The gel itself will be contained within cylindrical-shaped but interconnected conducting medium chambers 34 that are shown in FIGS. 3C and 3D. The depth of the conducting medium chambers 34, which is approximately the height of the long axis of the stimulator, affects the magnitude of the electric fields and currents that are induced by the device [Rafael CARBUNARU and Dominique M. Durand. Toroidal coil models for transcutaneous magnetic stimulation of nerves. IEEE Transactions on Biomedical Engineering. 48 (4, 2001): 434-441].

FIGS. 3C and 3D also show the coils of wire 35 that are wound around toroidal cores 36, consisting of high-permeability material (e.g., Supermendur). Lead wires (not shown) for the coils 35 pass from the stimulator coil(s) to the impulse generator (310 in FIG. 1) via the electronics port 32. Different circuit configurations are contemplated. If separate lead wires for each of the coils 35 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As seen in FIGS. 3C and 3D, the coils 35 and cores 36 around which they are wound are mounted as close as practical to the corresponding mesh 31 with openings through which conducting gel passes to the surface of the patient's skin. As seen in FIG. 3D, each coil and the core around which it is wound is mounted in its own housing 37, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium.

Different diameter toroidal coils and windings may be preferred for different applications. For a generic application, the outer diameter of the core may be typically 1 to 5 cm, with an inner diameter typically 0.5 to 0.75 of the outer diameter. The coil's winding around the core may be typically 3 to 250 in number, depending on the core diameter and depending on the desired coil inductance.

Signal generators for magnetic stimulators have been described for commercial systems [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006], as well as for custom designs for a control unit 330, impulse generator 310 and power source 320 [Eric BASHAM, Zhi Yang, Natalia Tchemodanov, and Wentai Liu. Magnetic Stimulation of Neural Tissue Techniques and System Design. pp 293-352, In: Implantable Neural Prostheses 1, Devices and Applications, D. Zhou and E. Greenbaum, eds., New York: Springer (2009); U.S. Pat. No. 7,744,523, entitled Drive circuit for magnetic stimulation, to Charles M. Epstein; U.S. Pat. No. 5,718,662, entitled Apparatus for the magnetic stimulation of cells or tissue, to Reza Jalinous; U.S. Pat. No. 5,766,124, entitled Magnetic stimulator for neuro-muscular tissue, to Poison]. Conventional magnetic nerve stimulators use a high current impulse generator that may produce discharge currents of 5,000 amps or more, which is passed through the stimulator coil, and which thereby produces a magnetic pulse. Typically, a transformer charges a capacitor in the impulse generator 310, which also contains circuit elements that limit the effect of undesirable electrical transients. Charging of the capacitor is under the control of a control unit 330, which accepts information such as the capacitor voltage, power and other parameters set by the user, as well as from various safety interlocks within the equipment that ensure proper operation, and the capacitor is then discharged through the coil via an electronic switch (e.g., a controlled rectifier) when the user wishes to apply the stimulus.

Greater flexibility is obtained by adding to the impulse generator a bank of capacitors that can be discharged at different times. Thus, higher impulse rates may be achieved by discharging capacitors in the bank sequentially, such that recharging of capacitors is performed while other capacitors in the bank are being discharged. Furthermore, by discharging some capacitors while the discharge of other capacitors is in progress, by discharging the capacitors through resistors having variable resistance, and by controlling the polarity of the discharge, the control unit may synthesize pulse shapes that approximate an arbitrary function.

The design and methods of use of impulse generators, control units, and stimulator coils for magnetic stimulators are informed by the designs and methods of use of impulse generators, control units, and electrodes (with leads) for comparable completely electrical nerve stimulators, but design and methods of use of the magnetic stimulators must take into account many special considerations, making it generally not straightforward to transfer knowledge of completely electrical stimulation methods to magnetic stimulation methods. Such considerations include determining the anatomical location of the stimulation and determining the appropriate pulse configuration [OLNEY R K, So Y T, Goodin D S, Aminoff M J. A comparison of magnetic and electric stimulation of peripheral nerves. Muscle Nerve 1990:13:957-963; J. NILSSON, M. Panizza, B. J. Roth et al. Determining the site of stimulation during magnetic stimulation of the peripheral nerve, Electroencephalographs and clinical neurophysiology 85(1992): 253-264; Nafia AL-MU-TAWALY, Hubert de Bruin, and Gary Hasey. The effects of pulse configuration on magnetic stimulation. Journal of Clinical Neurophysiology 20(5):361-370, 2003].

Furthermore, a potential practical disadvantage of using magnetic stimulator coils is that they may overheat when used over an extended period of time. Use of the above-mentioned toroidal coil and container of electrically conducting medium addresses this potential disadvantage. However, because of the poor coupling between the stimulating coils and the nerve tissue, large currents are nevertheless required to reach threshold electric fields. At high repetition rates, these currents can heat the coils to unacceptable levels in seconds to minutes depending on the power levels and pulse durations and rates. Two approaches to overcome heating are to cool the coils with flowing water or air or to increase the magnetic fields using ferrite cores (thus allowing smaller currents). For some applications where relatively long treatment times at high stimulation frequencies may be required, neither of these two approaches are adequate. Water-cooled coils overheat in a few minutes. Ferrite core coils heat more slowly due to the lower currents and heat capacity of the ferrite core, but also cool off more slowly and do not allow for water-cooling since the ferrite core takes up the volume where the cooling water would flow.

A solution to this problem is to use a fluid which contains ferromagnetic particles in suspension like a ferrofluid, or magnetorheological fluid as the cooling material. Ferrofluids are colloidal mixtures composed of nanoscale ferromagnetic, or ferrimagnetic, particles suspended in a carrier fluid, usually an organic solvent or water. The ferromagnetic nanoparticles are coated with a surfactant to prevent their agglomeration (due to van der Waals forces and magnetic forces). Ferrofluids have a higher heat capacity than water and will thus act as better coolants. In addition, the fluid will act as a ferrite core to increase the magnetic field strength. Also, since ferrofluids are paramagnetic, they obey Curie's law, and thus become less magnetic at higher temperatures. The strong magnetic field created by the magnetic stimulator coil will attract cold ferrofluid more than hot ferrofluid thus forcing the heated ferrofluid away from the coil. Thus, cooling may not require pumping of the ferrofluid through the coil, but only a simple convective system for cooling. This is an efficient cooling method which may require no additional energy input [U.S. Pat. No. 7,396,326 and published applications US2008/0114199, US2008/0177128, and US2008/0224808, all entitled Ferrofluid cooling and acoustical noise reduction in magnetic stimulators, respectively to Ghiron et al., Riehl et al., Riehl et al. and Ghiron et al.].

Magnetorheological fluids are similar to ferrofluids but contain larger magnetic particles which have multiple magnetic domains rather than the single domains of ferrofluids. [U.S. Pat. No. 6,743,371, Magneto sensitive fluid composition and a process for preparation thereof, to John et al.]. They can have a significantly higher magnetic permeability than ferrofluids and a higher volume fraction of iron to carrier. Combinations of magnetorheological and ferrofluids may also be used [M T LOPEZ-LOPEZ, P Kuzhir, S Lacis, G Bossis, F Gonzalez-Caballero and J D G Duran. Magnetorheology for suspensions of solid particles dispersed in ferrofluids. J. Phys.: Condens. Matter 18 (2006) S2803-S2813; Ladislau VEKAS. Ferrofluids and Magnetorheological Fluids. Advances in Science and Technology Vol. 54 (2008) pp 127-136.].

Commercially available magnetic stimulators include circular, parabolic, figure-of-eight (butterfly), and custom designs that are available commercially [Chris HOVEY and Reza Jalinous, THE GUIDE TO MAGNETIC STIMULATION, The Magstim Company Ltd, Spring Gardens, Whitland, Carmarthenshire, SA34 0HR, United Kingdom, 2006]. Additional embodiments of the magnetic stimulator coil 341 have been described [U.S. Pat. No. 6,179,770, entitled Coil assemblies for magnetic stimulators, to Stephen Mould; Kent DAVEY. Magnetic Stimulation Coil and Circuit Design. IEEE Transactions on Biomedical Engineering, Vol. 47 (No. 11, November 2000): 1493-1499]. Many of the problems that are associated with such conventional magnetic stimulators, e.g., the complexity of the impulse-generator circuitry and the problem with overheating, are largely avoided by the toroidal design shown in FIG. 3.

Thus, use of the container of conducting medium 351 allows one to generate (induce) electric fields in tissue (and electric field gradients and electric currents) that are equivalent to those generated using current magnetic stimulation devices, but with about 0.001 to 0.1 of the current conventionally applied to a magnetic stimulation coil. Therefore, with the present invention, it is possible to generate waveforms shown in FIG. 2 with relatively simple, low-power circuits that are powered by batteries. The circuits may be enclosed within a box 38 as shown in FIG. 3E, or the circuits may be attached to the stimulator itself (FIG. 3A-3D) to be used as a hand-held device. In either case, control over the unit may be made using only an on/off switch and power knob. The only other component that may be needed might be a cover 39 to keep the conducting fluid from leaking or drying out between uses. The currents passing through the coils of the magnetic stimulator will saturate its core (e.g., 0.1 to 2 Tesla magnetic field strength for Supermendur core material). This will require approximately 0.5 to 20 amperes of current being passed through each coil, typically 2 amperes, with voltages across each coil of 10 to 100 volts. The current is passed through the coils in bursts of pulses, as described in connection with FIGS. 2D and 2E, shaping an elongated electrical field of effect.

Preferred Embodiments of the Electrode-Based Stimulator

In another embodiment of the invention, electrodes applied to the surface of the neck, or to some other surface of the body, are used to non-invasively deliver electrical energy to a nerve, instead of delivering the energy to the nerve via a magnetic coil. The vagus nerve has been stimulated previously non-invasively using electrodes applied via leads to the surface of the skin. It has also been stimulated non-electrically through the use of mechanical vibration [HUSTON J M, Gallowitsch-Puerta M, Ochani M, Ochani K, Yuan R, Rosas-Ballina M et al (2007). Transcutaneous vagus nerve stimulation reduces serum high mobility group box 1 levels and improves survival in murine sepsis. Crit Care Med 35: 2762-2768; GEORGE M S, Aston-Jones G. Noninvasive techniques for probing neurocircuitry and treating illness: vagus nerve stimulation (VNS), transcranial magnetic stimulation (TMS) and transcranial direct current stimulation (tDCS). Neuropsychopharmacology 35(1, 2010):301-316]. However, no such reported uses of noninvasive vagus nerve stimulation were directed to the treatment of autistic individuals. U.S. Pat. No. 7,340,299, entitled Methods of indirectly stimulating the vagus nerve to achieve controlled asystole, to John D. PUSKAS, discloses the stimulation of the vagus nerve using electrodes placed on the neck of the patient, but that patent is unrelated to the treatment of autism spectrum disorders. Non-invasive electrical stimulation of the vagus nerve has also been described in Japanese patent application JP2009233024A with a filing date of Mar. 26, 2008, entitled Vagus Nerve Stimulation System, to Fukui YOSHIHOTO, in which a body surface electrode is applied to the neck to stimulate the vagus nerve electrically. However, that application pertains to the control of heart rate and is unrelated to the treatment of autism spectrum disorders. In patent publication US20080208266, entitled System and method for treating nausea and vomiting by vagus nerve stimulation, to LESSER et al., electrodes are used to stimulate the vagus nerve in the neck to reduce nausea and vomiting, but this too is unrelated to the treatment of autism.

Patent application US2010/0057154, entitled Device and method for the transdermal stimulation of a nerve of the human body, to DIETRICH et al., discloses a non-invasive transcutaneous/transdermal method for stimulating the vagus nerve, at an anatomical location where the vagus nerve has paths in the skin of the external auditory canal. Their non-invasive method involves performing electrical stimulation at that location, using surface stimulators that are similar to those used for peripheral nerve and muscle stimulation for treatment of pain (transdermal electrical nerve stimulation), muscle training (electrical muscle stimulation) and electroacupuncture of defined meridian points. The method used in that application is similar to the ones used in U.S. Pat. No. 4,319,584, entitled Electrical pulse acupressure system, to McCALL, for electroacupuncture; U.S. Pat. No. 5,514,175 entitled Auricular electrical stimulator, to KIM et al., for the treatment of pain; and U.S. Pat. No. 4,966,164, entitled Combined sound generating device and electrical acupuncture device and method for using the same, to COLSEN et al., for combined sound/electroacupuncture. A related application is US2006/0122675, entitled Stimulator for auricular branch of vagus nerve, to LIBBUS et al. Similarly, U.S. Pat. No. 7,386,347, entitled Electric stimulator for alpha-wave derivation, to CHUNG et al., described electrical stimulation of the vagus nerve at the ear. Patent application US2008/0288016, entitled Systems and Methods for Stimulating Neural Targets, to AMURTHUR et al., also discloses electrical stimulation of the vagus nerve at the ear. U.S. Pat. No. 4,865,048, entitled Method and apparatus for drug free neurostimulation, to ECKERSON, teaches electrical stimulation of a branch of the vagus nerve behind the ear on the mastoid processes, in order to treat symptoms of drug withdrawal. KRAUS et al described similar methods of stimulation at the ear [KRAUS T, Hosl K, Kiess O, Schanze A, Kornhuber J, Forster C (2007). BOLD fMRI deactivation of limbic and temporal brain structures and mood enhancing effect by transcutaneous vagus nerve stimulation. J Neural Transm 114: 1485-1493]. However, none of the disclosures in these patents or patent applications for electrical stimulation of the vagus nerve at the ear are used to treat autism spectrum disorders.

Embodiments of the present invention may differ with regard to the number of electrodes that are used, the distance between electrodes, and whether disk or ring electrodes are used. In preferred embodiments of the method, one selects the electrode configuration for individual patients, in such a way as to optimally focus electric fields and currents onto the selected nerve, without generating excessive currents on the surface of the skin. This tradeoff between focality and surface currents is described by DATTA et al. [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174]. Although DATTA et al. are addressing the selection of electrode configuration specifically for transcranial current stimulation, the principles that they describe are applicable to peripheral nerves as well [RATTAY F. Analysis of models for extracellular fiber stimulation. IEEE Trans. Biomed. Eng. 36 (1989): 676-682].

Considering that the nerve stimulating device 301 in FIG. 2A and the nerve stimulating device 302 in FIG. 2B both control the shape of electrical impulses, their functions are analogous, except that one stimulates nerves via a pulse of a magnetic field, and the other stimulates nerves via an electrical pulse applied through surface electrodes. Accordingly, general features recited for the nerve stimulating device 301 apply as well to the latter stimulating device 302 and will not be repeated here. The preferred parameters for each nerve stimulating device are those that produce the desired therapeutic effects.

A preferred embodiment of an electrode-based stimulator is shown in FIG. 4A. A cross-sectional view of the stimulator along its long axis is shown in FIG. 4B. As shown, the stimulator (730) comprises two heads (731) and a body (732) that joins them. Each head (731) contains a stimulating electrode. The body of the stimulator (732) contains the electronic components and battery (not shown) that are used to generate the signals that drive the electrodes, which are located behind the insulating board (733) that is shown in FIG. 4B. However, in other embodiments of the invention, the electronic components that generate the signals that are applied to the electrodes may be separate, but connected to the electrode head (731) using wires. Furthermore, other embodiments of the invention may contain a single such head or ore than two heads.

Heads of the stimulator (731) are applied to a surface of the patient's body, during which time the stimulator may be held in place by straps or frames or collars, or the stimulator may be held against the patient's body by hand. In either case, the level of stimulation power may be adjusted with a wheel (734) that also serves as an on/off switch. A light (735) is illuminated when power is being supplied to the stimulator. An optional cap may be provided to cover each of the stimulator heads (731), to protect the device when not in use, to avoid accidental stimulation, and to prevent material within the head from leaking or drying. Thus, in this embodiment of the invention, mechanical and electronic components of the stimulator (impulse generator, control unit, and power source) are compact, portable, and simple to operate.

Figure 4C:
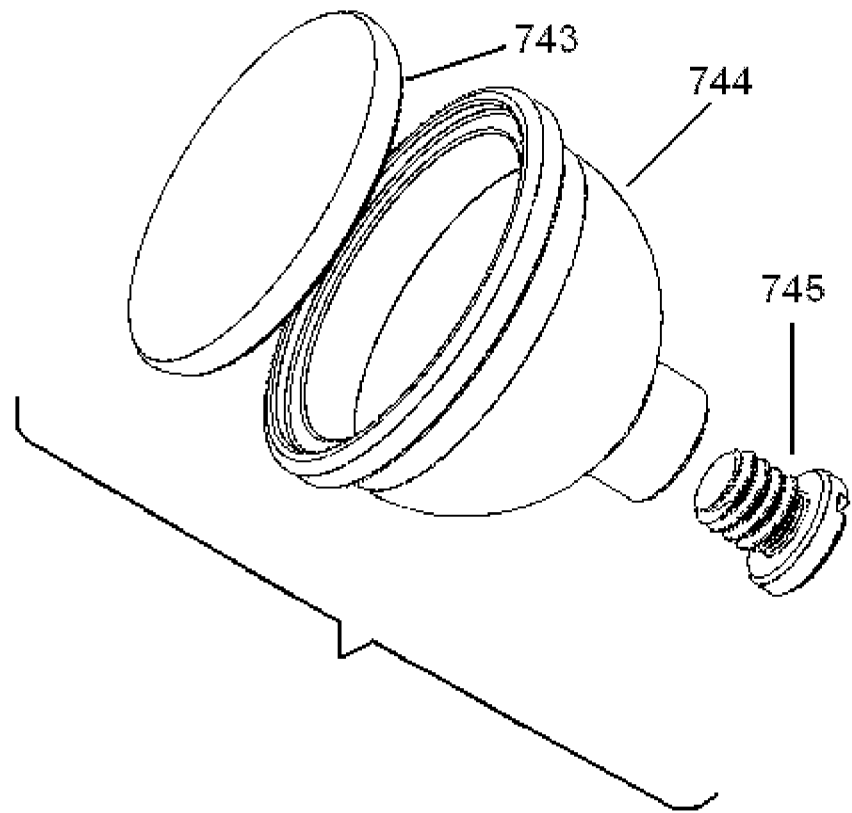
FIG. 4C is an exploded view of one of the electrode assemblies of the dual-electrode stimulator of FIG. 4A.
Figure 4D:
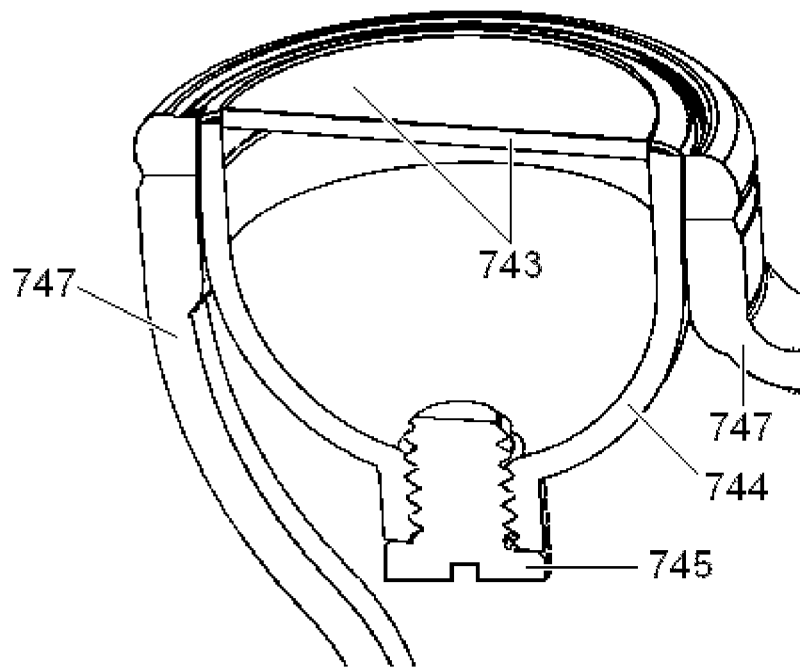
FIG. 4D is a cut-a-way view of the electrode assembly of FIG. 4C.

Details of one embodiment of the stimulator head are shown in FIGS. 4C and 4D. The electrode head may be assembled from a disc without fenestration (743), or alternatively from a snap-on cap that serves as a tambour for a dielectric or conducting membrane, or alternatively the head may have a solid fenestrated head-cup. The electrode may also be a screw (745). The preferred embodiment of the disc (743) is a solid, ordinarily uniformly conducting disc (e.g., metal such as stainless steel), which is possibly flexible in some embodiments. An alternate embodiment of the disc is a non-conducting (e.g., plastic) aperture screen that permits electrical current to pass through its apertures, e.g., through an array of apertures (fenestration). The electrode (745, also 340 in FIG. 2B) seen in each stimulator head may have the shape of a screw that is flattened on its tip. Pointing of the tip would make the electrode more of a point source, such that the equations for the electrical potential may have a solution corresponding more closely to a far-field approximation. Rounding of the electrode surface or making the surface with another shape will likewise affect the boundary conditions that determine the electric field. Completed assembly of the stimulator head is shown in FIG. 4D, which also shows how the head is attached to the body of the stimulator (747).

If a membrane is used, it ordinarily serves as the interface shown as 351 in FIG. 2B. For example, the membrane may be made of a dielectric (non-conducting) material, such as a thin sheet of Mylar (biaxially-oriented polyethylene terephthalate, also known as BoPET). In other embodiments, it may be made of conducting material, such as a sheet of Tecophlic material from Lubrizol Corporation, 29400 Lakeland Boulevard, Wickliffe, Ohio 44092. In one embodiment, apertures of the disc may be open, or they may be plugged with conducting material, for example, KM10T hydrogel from Katecho Inc., 4020 Gannett Ave., Des Moines Iowa 50321. If the apertures are so-plugged, and the membrane is made of conducting material, the membrane becomes optional, and the plug serves as the interface 351 shown in FIG. 2B.

The head-cup (744) is filled with conducting material (350 in FIG. 2B), for example, SIGNAGEL Electrode Gel from Parker Laboratories, Inc., 286 Eldridge Rd., Fairfield N.J. 07004. The head-cup (744) and body of the stimulator are made of a non-conducting material, such as acrylonitrile butadiene styrene. The depth of the head-cup from its top surface to the electrode may be between one and six centimeters. The head-cup may have a different curvature than what is shown in FIG. 4, or it may be tubular or conical or have some other inner surface geometry that will affect the Neumann boundary conditions that determine the electric field strength.

If an outer membrane is used and is made of conducting materials, and the disc (743) in FIG. 4C is made of solid conducting materials such as stainless steel, then the membrane becomes optional, in which case the disc may serve as the interface 351 shown in FIG. 2B. Thus, an embodiment without the membrane is shown in FIGS. 4C and 4D. This version of the device comprises a solid (but possibly flexible in some embodiments) conducting disc that cannot absorb fluid, the non-conducting stimulator head (744) into or onto which the disc is placed, and the electrode (745), which is also a screw. It is understood that the disc (743) may have an anisotropic material or electrical structure, for example, wherein a disc of stainless steel has a grain, such that the grain of the disc should be rotated about its location on the stimulator head, in order to achieve optimal electrical stimulation of the patient. As seen in FIG. 4D, these items are assembled to become a sealed stimulator head that is attached to the body of the stimulator (747). The disc (743) may screw into the stimulator head (744), it may be attached to the head with adhesive, or it may be attached by other methods that are known in the art. The chamber of the stimulator head-cup is filled with a conducting gel, fluid, or paste, and because the disc (743) and electrode (745) are tightly sealed against the stimulator head-cup (744), the conducting material within the stimulator head cannot leak out. In addition, this feature allows the user to easily clean the outer surface of the device (e.g., with isopropyl alcohol or similar disinfectant), avoiding potential contamination during subsequent uses of the device.

In some embodiments, the interface comprises a fluid permeable material that allows for passage of current through the permeable portions of the material. In these embodiments, a conductive medium (such as a gel) is preferably situated between the electrode(s) and the permeable interface. The conductive medium provides a conductive pathway for electrons to pass through the permeable interface to the outer surface of the interface and to the patient's skin.

In other embodiments of the present invention, the interface (351 in FIG. 2B) is made from a very thin material with a high dielectric constant, such as material used to make capacitors. For example, it may be Mylar having a submicron thickness (preferably in the range 0.5 to 1.5 microns) having a dielectric constant of about 3. Because one side of Mylar is slick, and the other side is microscopically rough, the present invention contemplates two different configurations: one in which the slick side is oriented towards the patient's skin, and the other in which the rough side is so-oriented. Thus, at stimulation Fourier frequencies of several kilohertz or greater, the dielectric interface will capacitively couple the signal through itself, because it will have an impedance comparable to that of the skin. Thus, the dielectric interface will isolate the stimulator's electrode from the tissue, yet allow current to pass. In one embodiment of the present invention, non-invasive electrical stimulation of a nerve is accomplished essentially substantially capacitively, which reduces the amount of ohmic stimulation, thereby reducing the sensation the patient feels on the tissue surface. This would correspond to a situation, for example, in which at least 30%, preferably at least 50%, of the energy stimulating the nerve comes from capacitive coupling through the stimulator interface, rather than from ohmic coupling. In other words, a substantial portion (e.g., 50%) of the voltage drop is across the dielectric interface, while the remaining portion is through the tissue.

In certain exemplary embodiments, the interface and/or its underlying mechanical support comprise materials that will also provide a substantial or complete seal of the interior of the device. This inhibits any leakage of conducting material, such as gel, from the interior of the device and also inhibits any fluids from entering the device. In addition, this feature allows the user to easily clean the surface of the dielectric material (e.g., with isopropyl alcohol or similar disinfectant), avoiding potential contamination during subsequent uses of the device. One such material is a thin sheet of Mylar, supported by a stainless steel disc, as described above.

The selection of the material for the dielectric constant involves at least two important variables: (1) the thickness of the interface; and (2) the dielectric constant of the material. The thinner the interface and/or the higher the dielectric constant of the material, the lower the voltage drop across the dielectric interface (and thus the lower the driving voltage required). For example, with Mylar, the thickness could be about 0.5 to 5 microns (preferably about 1 micron) with a dielectric constant of about 3. For a piezoelectric material like barium titanate or PZT (lead zirconate titanate), the thickness could be about 100-400 microns (preferably about 200 microns or 0.2 mm) because the dielectric constant is >1000.

One of the novelties of the embodiment that is a non-invasive capacitive stimulator (hereinafter referred to more generally as a capacitive electrode) arises in that it uses a low voltage (generally less than 100 volt) power source, which is made possible by the use of a suitable stimulation waveform, such as the waveform that is disclosed herein (FIG. 2). In addition, the capacitive electrode allows for the use of an interface that provides a more adequate seal of the interior of the device. The capacitive electrode may be used by applying a small amount of conductive material (e.g., conductive gel as described above) to its outer surface. In some embodiments, it may also be used by contacting dry skin, thereby avoiding the inconvenience of applying an electrode gel, paste, or other electrolytic material to the patient's skin and avoiding the problems associated with the drying of electrode pastes and gels. Such a dry electrode would be particularly suitable for use with a patient who exhibits dermatitis after the electrode gel is placed in contact with the skin [Ralph J. COSKEY. Contact dermatitis caused by ECG electrode jelly. Arch Dermatol 113(1977): 839-840]. The capacitive electrode may also be used to contact skin that has been wetted (e.g., with tap water or a more conventional electrolyte material) to make the electrode-skin contact (here the dielectric constant) more uniform [A L ALEXELONESCU, G Barbero, F C M Freire, and R Merletti. Effect of composition on the dielectric properties of hydrogels for biomedical applications. Physiol. Meas. 31 (2010) S169-S182].

As described below, capacitive biomedical electrodes are known in the art, but when used to stimulate a nerve noninvasively, a high voltage power supply is currently used to perform the stimulation. Otherwise, prior use of capacitive biomedical electrodes has been limited to invasive, implanted applications; to non-invasive applications that involve monitoring or recording of a signal, but not stimulation of tissue; to non-invasive applications that involve the stimulation of something other than a nerve (e.g., tumor); or as the dispersive electrode in electrosurgery.

Evidence of a long-felt but unsolved need, and evidence of failure of others to solve the problem that is solved by the this embodiment of the present invention (low-voltage, non-invasive capacitive stimulation of a nerve), is provided by KELLER and Kuhn, who review the previous high-voltage capacitive stimulating electrode of GEDDES et al and write that "Capacitive stimulation would be a preferred way of activating muscle nerves and fibers, when the inherent danger of high voltage breakdowns of the dielectric material can be eliminated. Goal of future research could be the development of improved and ultra-thin dielectric foils, such that the high stimulation voltage can be lowered." [L. A. GEDDES, M. Hinds, and K. S. Foster. Stimulation with capacitor electrodes. Medical and Biological Engineering and Computing 25(1987): 359-360; Thierry KELLER and Andreas Kuhn. Electrodes for transcutaneous (surface) electrical stimulation. Journal of Automatic Control, University of Belgrade 18(2, 2008):35-45, on page 39]. It is understood that in the United States, according to the 2005 National Electrical Code, high voltage is any voltage over 600 volts. U.S. Pat. No. 3,077,884, entitled Electro-physiotherapy apparatus, to BARTROW et al, U.S. Pat. No. 4,144,893, entitled Neuromuscular therapy device, to HICKEY and U.S. Pat. No. 7,933,648, entitled High voltage transcutaneous electrical stimulation device and method, to TANRISEVER, also describe high voltage capacitive stimulation electrodes. U.S. Pat. No. 7,904,180, entitled Capacitive medical electrode, to JUOLA et al, describes a capacitive electrode that includes transcutaneous nerve stimulation as one intended application, but that patent does not describe stimulation voltages or stimulation waveforms and frequencies that are to be used for the transcutaneous stimulation. U.S. Pat. No. 7,715,921, entitled Electrodes for applying an electric field in-vivo over an extended period of time, to PALTI, and U.S. Pat. No. 7,805,201, entitled Treating a tumor or the like with an electric field, to PALTI, also describe capacitive stimulation electrodes, but they are intended for the treatment of tumors, do not disclose uses involving nerves, and teach stimulation frequencies in the range of 50 kHz to about 500 kHz.

This embodiment of the present invention uses a different method to lower the high stimulation voltage than developing ultra-thin dielectric foils, namely, to use a suitable stimulation waveform, such as the waveform that is disclosed herein (FIG. 2). That waveform has significant Fourier components at higher frequencies than waveforms used for transcutaneous nerve stimulation as currently practiced. Thus, one of ordinary skill in the art would not have combined the claimed elements, because transcutaneous nerve stimulation is performed with waveforms having significant Fourier components only at lower frequencies, and noninvasive capacitive nerve stimulation is performed at higher voltages. In fact, the elements in combination do not merely perform the function that each element performs separately. The dielectric material alone may be placed in contact with the skin in order to perform pasteless or dry stimulation, with a more uniform current density than is associated with ohmic stimulation, albeit with high stimulation voltages [L. A. GEDDES, M. Hinds, and K. S. Foster. Stimulation with capacitor electrodes. Medical and Biological Engineering and Computing 25(1987): 359-360; Yongmin KIM, H. Gunter Zieber, and Frank A. Yang. Uniformity of current density under stimulating electrodes. Critical Reviews in Biomedical Engineering 17(1990, 6): 585-619]. With regard to the waveform element, a waveform that has significant Fourier components at higher frequencies than waveforms currently used for transcutaneous nerve stimulation may be used to selectively stimulate a deep nerve and avoid stimulating other nerves, as disclosed herein for both noncapacitive and capacitive electrodes. But it is the combination of the two elements (dielectric interface and waveform) that makes it possible to stimulate a nerve capacitively without using the high stimulation voltage as is currently practiced.

Another embodiment of the electrode-based stimulator is shown in FIG. 5, showing a device in which electrically conducting material is dispensed from the device to the patient's skin. In this embodiment, the interface (351 in FIG. 2B) is the conducting material itself. FIGS. 5A and 5B respectively provide top and bottom views of the outer surface of the electrical stimulator 50. FIG. 5C provides a bottom view of the stimulator 50, after sectioning along its long axis to reveal the inside of the stimulator.

Figure 5A:
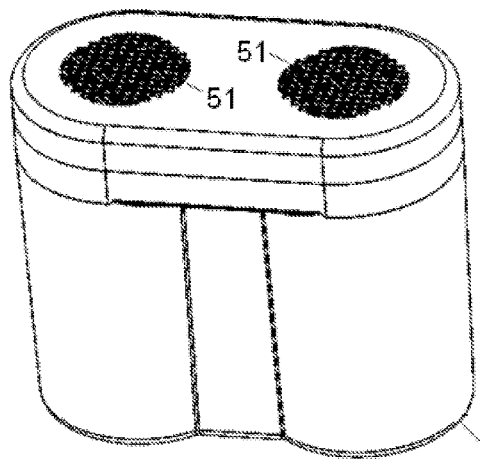
FIG. 5A is perspective view of the top of an alternative embodiment of the dual-electrode stimulator of FIG. 4A.
Figure 5B:
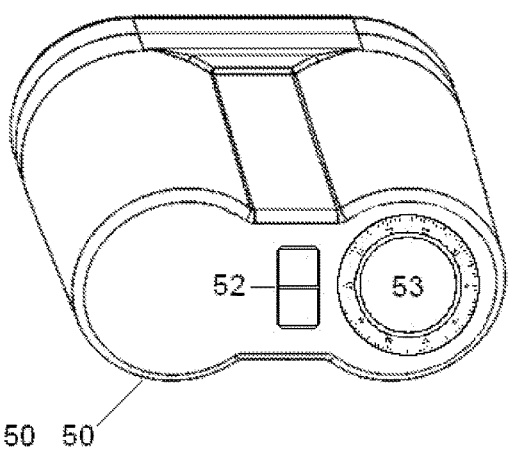
FIG. 5B is a perspective view of the bottom of the dual-electrode stimulator of FIG. 5A.
Figure 5C:
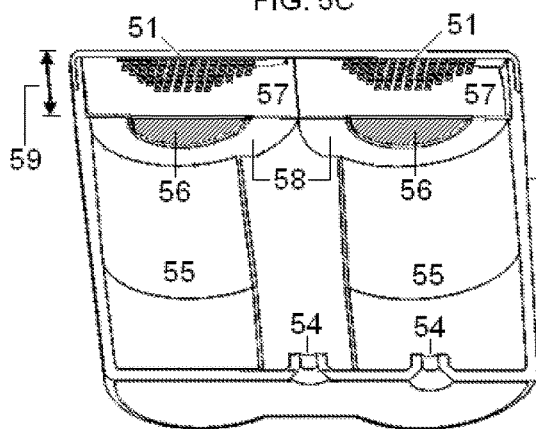
FIG. 5C is a cut-a-way view of the dual-electrode stimulator of FIG. 5A.

FIGS. 5A and 5C show a mesh 51 with openings that permit a conducting gel to pass from inside of the stimulator to the surface of the patient's skin at the position of nerve or tissue stimulation. Thus, the mesh with openings 51 is the part of the stimulator that is applied to the skin of the patient, through which conducting material may be dispensed. In any given stimulator, the distance between the two mesh openings 51 in FIG. 5A is constant, but it is understood that different stimulators may be built with different inter-mesh distances, in order to accommodate the anatomy and physiology of individual patients. Alternatively, the inter-mesh distance may be made variable as in the eyepieces of a pair of binoculars. A covering cap (not shown) is also provided to fit snugly over the top of the stimulator housing and the mesh openings 51, in order to keep the housing's conducting medium from leaking or drying when the device is not in use.

FIGS. 5B and 5C show the bottom of the self-contained stimulator 50. An on/off switch 52 is attached through a port 54, and a power-level controller 53 is attached through another port 54. The switch is connected to a battery power source (320 in FIG. 2B), and the power-level controller is attached to the control unit (330 in FIG. 2B) of the device. The power source battery and power-level controller, as well as the impulse generator (310 in FIG. 2B) are located (but not shown) in the rear compartment 55 of the housing of the stimulator 50.

Individual wires (not shown) connect the impulse generator (310 in FIG. 2B) to the stimulator's electrodes 56. The two electrodes 56 are shown here to be elliptical metal discs situated between the head compartment 57 and rear compartment 55 of the stimulator 50. A partition 58 separates each of the two head compartments 57 from one another and from the single rear compartment 55. Each partition 58 also holds its corresponding electrode in place. However, each electrode 56 may be removed to add electrically conducting gel (350 in FIG. 2B) to each head compartment 57. An optional non-conducting variable-aperture iris diaphragm may be placed in front of each of the electrodes within the head compartment 57, in order to vary the effective surface area of each of the electrodes. Each partition 58 may also slide towards the head of the device in order to dispense conducting gel through the mesh apertures 51. The position of each partition 58 therefore determines the distance 59 between its electrode 56 and mesh openings 51, which is variable in order to obtain the optimally uniform current density through the mesh openings 51. The outside housing of the stimulator 50, as well as each head compartment 57 housing and its partition 58, are made of electrically insulating material, such as acrylonitrile butadiene styrene, so that the two head compartments are electrically insulated from one another. Although the embodiment in FIG. 5 is shown to be a non-capacitive stimulator, it is understood that it may be converted into a capacitive stimulator by replacing the mesh openings 51 with a dielectric material, such as a sheet of Mylar, or by covering the mesh openings 51 with a sheet of such dielectric material.

In preferred embodiments of the electrode-based stimulator shown in FIG. 2B, electrodes are made of a metal, such as stainless steel, platinum, or a platinum-iridium alloy. However, in other embodiments, the electrodes may have many other sizes and shapes, and they may be made of other materials [Thierry KELLER and Andreas Kuhn. Electrodes for transcutaneous (surface) electrical stimulation. Journal of Automatic Control, University of Belgrade, 18(2, 2008): 35-45; G. M. LYONS, G. E. Leane, M. Clarke-Moloney, J. V. O'Brien, P. A. Grace. An investigation of the effect of electrode size and electrode location on comfort during stimulation of the gastrocnemius muscle. Medical Engineering & Physics 26 (2004) 873-878; Bonnie J. FORRESTER and Jerrold S. Petrofsky. Effect of Electrode Size, Shape, and Placement During Electrical Stimulation. The Journal of Applied Research 4, (2, 2004): 346-354; Gad ALON, Gideon Kantor and Henry S. Ho. Effects of Electrode Size on Basic Excitatory Responses and on Selected Stimulus Parameters. Journal of Orthopaedic and Sports Physical Therapy. 20(1, 1994):29-35].

For example, the stimulator's conducting materials may be nonmagnetic, and the stimulator may be connected to the impulse generator by long nonmagnetic wires (345 in FIG. 2B), so that the stimulator may be used in the vicinity of a strong magnetic field, possibly with added magnetic shielding. As another example, there may be more than two electrodes; the electrodes may comprise multiple concentric rings; and the electrodes may be disc-shaped or have a non-planar geometry. They may be made of other metals or resistive materials such as silicon-rubber impregnated with carbon that have different conductive properties [Stuart F. COGAN. Neural Stimulation and Recording Electrodes. Annu. Rev. Biomed. Eng. 2008. 10:275-309; Michael F. NOLAN. Conductive differences in electrodes used with transcutaneous electrical nerve stimulation devices. Physical Therapy 71(1991):746-751].

Although the electrode may consist of arrays of conducting material, the embodiments shown in FIGS. 4 and 5 avoid the complexity and expense of array or grid electrodes [Ana POPOVIC-BIJELIC, Goran Bijelic, Nikola Jorgovanovic, Dubravka Bojanic, Mirjana B. Popovic, and Dejan B. Popovic. Multi-Field Surface Electrode for Selective Electrical Stimulation. Artificial Organs 29 (6, 2005):448-452; Dejan B. POPOVIC and Mirjana B. Popovic. Automatic determination of the optimal shape of a surface electrode: Selective stimulation. Journal of Neuroscience Methods 178 (2009) 174-181; Thierry KELLER, Marc Lawrence, Andreas Kuhn, and Manfred Morari. New Multi-Channel Transcutaneous Electrical Stimulation Technology for Rehabilitation. Proceedings of the 28th IEEE EMBS Annual International Conference New York City, USA, Aug. 30-Sep. 3, 2006 (WeC14.5): 194-197]. This is because the designs shown in FIGS. 4 and 5 provide a uniform surface current density, which would otherwise be a potential advantage of electrode arrays, and which is a trait that is not shared by most electrode designs [Kenneth R. BRENNEN. The Characterization of Transcutaneous Stimulating Electrodes. IEEE Transactions on Biomedical Engineering BME-23 (4, 1976): 337-340; Andrei PATRICIU, Ken Yoshida, Johannes J. Struijk, Tim P. DeMonte, Michael L. G. Joy, and Hans Stødkilde-Jørgensen. Current Density Imaging and Electrically Induced Skin Burns Under Surface Electrodes. IEEE Transactions on Biomedical Engineering 52 (12, 2005): 2024-2031; R. H. GEUZE. Two methods for homogeneous field defibrillation and stimulation. Med. and Biol. Eng. and Comput. 21 (1983), 518-520; J. PETROFSKY, E. Schwab, M. Cuneo, J. George, J. Kim, A. Almalty, D. Lawson, E. Johnson and W. Remigo. Current distribution under electrodes in relation to stimulation current and skin blood flow: are modern electrodes really providing the current distribution during stimulation we believe they are? Journal of Medical Engineering and Technology 30 (6, 2006): 368-381; Russell G. MAUS, Erin M. McDonald, and R. Mark Wightman. Imaging of Nonuniform Current Density at Microelectrodes by Electrogenerated Chemiluminescence. Anal. Chem. 71(1999): 4944-4950]. In fact, patients found the design shown in FIGS. 4 and 5 to be less painful in a direct comparison with a commercially available grid-pattern electrode [UltraStim grid-pattern electrode, Axelggard Manufacturing Company, 520 Industrial Way, Fallbrook Calif., 2011]. The embodiment of the electrode that uses capacitive coupling is particularly suited to the generation of uniform stimulation currents [Yongmin KIM, H. Gunter Zieber, and Frank A. Yang. Uniformity of current density under stimulating electrodes. Critical Reviews in Biomedical Engineering 17(1990, 6): 585-619].

The electrode-based stimulator designs shown in FIGS. 4 and 5 situate the electrode remotely from the surface of the skin within a chamber, with conducting material placed in the chamber between the skin and electrode. Such a chamber design had been used prior to the availability of flexible, flat, disposable electrodes [U.S. Pat. No. 3,659,614, entitled Adjustable headband carrying electrodes for electrically stimulating the facial and mandibular nerves, to Jankelson; U.S. Pat. No. 3,590,810, entitled Biomedical body electrode, to Kopecky; U.S. Pat. No. 3,279,468, entitled Electrotherapeutic facial mask apparatus, to Le Vine; U.S. Pat. No. 6,757,556, entitled Electrode sensor, to Gopinathan et al; U.S. Pat. No. 4,383,529, entitled Iontophoretic electrode device, method and gel insert, to Webster; U.S. Pat. No. 4,220,159, entitled Electrode, to Francis et al. U.S. Pat. No. 3,862,633, U.S. Pat. No. 4,182,346, and U.S. Pat. No. 3,973,557, entitled Electrode, to Allison et al; U.S. Pat. No. 4,215,696, entitled Biomedical electrode with pressurized skin contact, to Bremer et al; and U.S. Pat. No. 4,166,457, entitled Fluid self-sealing bioelectrode, to Jacobsen et al.] The stimulator designs shown in FIGS. 4 and 5 are also self-contained units, housing the electrodes, signal electronics, and power supply. Portable stimulators are also known in the art, for example, U.S. Pat. No. 7,171,266, entitled Electroacupuncture device with stimulation electrode assembly, to Gruzdowich. One of the novelties of the designs shown in FIGS. 4 and 5 is that the stimulator, along with a correspondingly suitable stimulation waveform, shapes the electric field, producing a selective physiological response by stimulating that nerve, but avoiding substantial stimulation of nerves and tissue other than the target nerve, particularly avoiding the stimulation of nerves that produce pain. The shaping of the electric field is described in terms of the corresponding field equations in commonly assigned application US20110230938 (application Ser. No. 13/075, 746) entitled Devices and methods for non-invasive electrical stimulation and their use for vagal nerve stimulation on the neck of a patient, to SIMON et al., which is hereby incorporated by reference.

In one embodiment, the magnetic stimulator coil 341 in FIG. 2A has a body that is similar to the electrode-based stimulator shown in FIG. 5C. To compare the electrode-based stimulator with the magnetic stimulator, refer to FIG. 5D, which shows the magnetic stimulator 530 sectioned along its long axis to reveal its inner structure. As described below, it reduces the volume of conducting material that must surround a toroidal coil, by using two toroids, side-by-side, and passing electrical current through the two toroidal coils in opposite directions. In this configuration, the induced electrical current will flow from the lumen of one toroid, through the tissue and back through the lumen of the other, completing the circuit within the toroids' conducting medium. Thus, minimal space for the conducting medium is required around the outside of the toroids at positions near from the gap between the pair of coils. An additional advantage of using two toroids in this configuration is that this design will greatly increase the magnitude of the electric field gradient between them, which is crucial for exciting long, straight axons such as the vagus nerve and certain peripheral nerves.

Figure 5D:
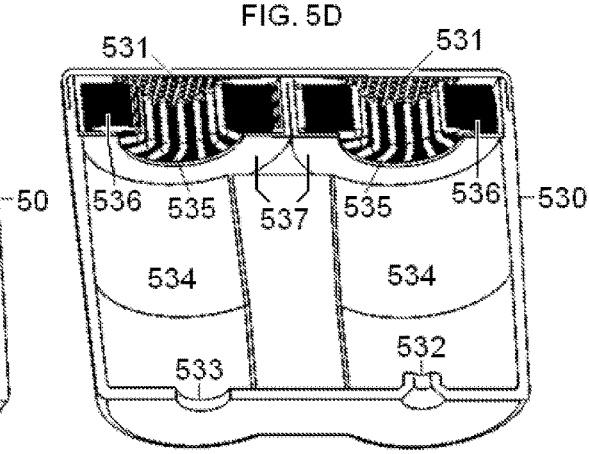
FIG. 5D is another cut-a-way view of the dual-electrode stimulator of FIG. 5.

As seen in FIG. 5D, a mesh 531 has openings that permit a conducting gel (within 351 in FIG. 2A) to pass from the inside of the stimulator to the surface of the patient's skin at the location of nerve or tissue stimulation. Thus, the mesh with openings 531 is the part of the magnetic stimulator that is applied to the skin of the patient.

FIG. 5D also shows openings at the opposite end of the magnetic stimulator 530. One of the openings is an electronics port 532 through which wires pass from the stimulator coil(s) to the impulse generator (310 in FIG. 2A). The second opening is a conducting gel port 533 through which conducting gel (351 in FIG. 2A) may be introduced into the magnetic stimulator 530 and through which a screw-driven piston arm may be introduced to dispense conducting gel through the mesh 531. The gel itself is contained within cylindrical-shaped but interconnected conducting medium chambers 534 that are shown in FIG. 5D. The depth of the conducting medium chambers 534, which is approximately the height of the long axis of the stimulator, affects the magnitude of the electric fields and currents that are induced by the magnetic stimulator device [Rafael CARBUNARU and Dominique M. Durand. Toroidal coil models for transcutaneous magnetic stimulation of nerves. IEEE Transactions on Biomedical Engineering. 48 (4, 2001): 434-441].

FIG. 5D also show the coils of wire 535 that are wound around toroidal cores 536, consisting of high-permeability material (e.g., Supermendur). Lead wires (not shown) for the coils 535 pass from the stimulator coil(s) to the impulse generator (310 in FIG. 2A) via the electronics port 532. Different circuit configurations are contemplated. If separate lead wires for each of the coils 535 connect to the impulse generator (i.e., parallel connection), and if the pair of coils are wound with the same handedness around the cores, then the design is for current to pass in opposite directions through the two coils. On the other hand, if the coils are wound with opposite handedness around the cores, then the lead wires for the coils may be connected in series to the impulse generator, or if they are connected to the impulse generator in parallel, then the design is for current to pass in the same direction through both coils.

As also seen in FIG. 5D, the coils 535 and cores 536 around which they are wound are mounted as close as practical to the corresponding mesh 531 with openings through which conducting gel passes to the surface of the patient's skin. As shown, each coil and the core around which it is wound is mounted in its own housing 537, the function of which is to provide mechanical support to the coil and core, as well as to electrically insulate a coil from its neighboring coil. With this design, induced current will flow from the lumen of one toroid, through the tissue and back through the lumen of the other, completing the circuit within the toroids' conducting medium. A difference between the structure of the electrode-based stimulator shown in FIG. 5C and the magnetic stimulator shown in FIG. 5D is that the conducting gel is maintained within the chambers 57 of the electrode-based stimulator, which is generally closed on the back side of the chamber because of the presence of the electrode 56; but in the magnetic stimulator, the hole of each toroidal core and winding is open, permitting the conducting gel to enter the interconnected chambers 534.

Application of the Stimulators to the Neck of the Patient

Selected nerve fibers are stimulated in different embodiments of methods that make use of the disclosed electrical stimulation devices, including stimulation of the vagus nerve at a location in the patient's neck. At that location, the vagus nerve is situated within the carotid sheath, near the carotid artery and the interior jugular vein. The carotid sheath is located at the lateral boundary of the retopharyngeal space on each side of the neck and deep to the sternocleidomastoid muscle. The left vagus nerve is sometimes selected for stimulation because stimulation of the right vagus nerve may produce undesired effects on the heart, but depending on the application, the right vagus nerve or both right and left vagus nerves may be stimulated instead.

The three major structures within the carotid sheath are the common carotid artery, the internal jugular vein and the vagus nerve. The carotid artery lies medial to the internal jugular vein, and the vagus nerve is situated posteriorly between the two vessels. Typically, the location of the carotid sheath or interior jugular vein in a patient (and therefore the location of the vagus nerve) will be ascertained in any manner known in the art, e.g., by feel or ultrasound imaging. Proceeding from the skin of the neck above the sternocleidomastoid muscle to the vagus nerve, a line may pass successively through the sternocleidomastoid muscle, the carotid sheath and the internal jugular vein, unless the position on the skin is immediately to either side of the external jugular vein. In the latter case, the line may pass successively through only the sternocleidomastoid muscle and the carotid sheath before encountering the vagus nerve, missing the interior jugular vein. Accordingly, a point on the neck adjacent to the external jugular vein might be preferred for non-invasive stimulation of the vagus nerve. The magnetic stimulator coil may be centered on such a point, at the level of about the fifth to sixth cervical vertebra.

Figure 6B:
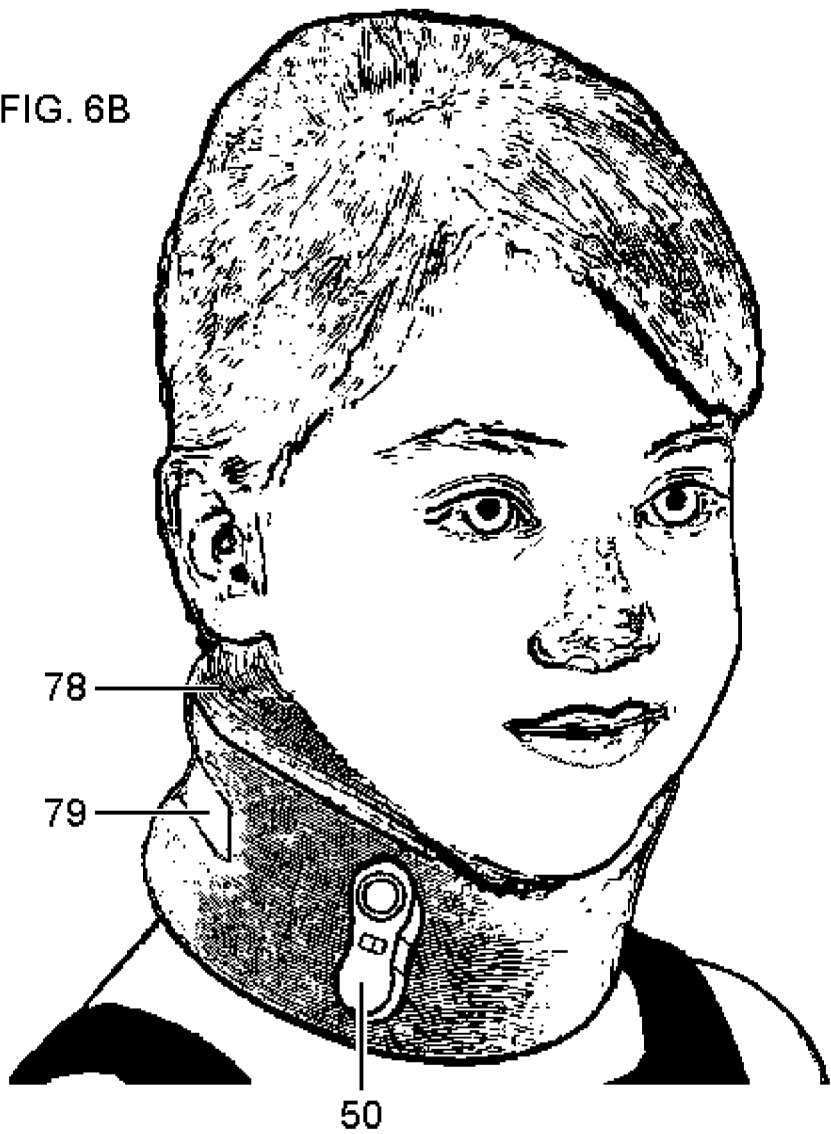
FIG. 6B illustrates the approximate position for stimulation of a child.

FIG. 6 illustrates use of the devices shown in FIGS. 3, 4 and 5 to stimulate the vagus nerve at that location in the neck, in which the stimulator device 50 or 530 in FIG. 5 is shown to be applied to the target location on the patient's neck as described above. For reference, FIG. 6A shows the locations of the following vertebrae: first cervical vertebra 71, the fifth cervical vertebra 75, the sixth cervical vertebra 76, and the seventh cervical vertebra 77. FIG. 6B shows the stimulator 50 applied to the neck of a child, which is partially immobilized with a foam cervical collar 78 that is similar to ones used for neck injuries and neck pain. The collar is tightened with a strap 79, and the stimulator is inserted through a hole in the collar to reach the child's neck surface. As shown, the stimulator is turned on and off with a switch that is located on the stimulator, and the amplitude of stimulation may be adjusted with a control knob that is also located on the stimulator. In other models, the stimulator may be turned on and off remotely, using a wireless controller that may be used to adjust all of the stimulation parameters of the controller (on/off, stimulation amplitude, frequency, etc.).

Figure 7:
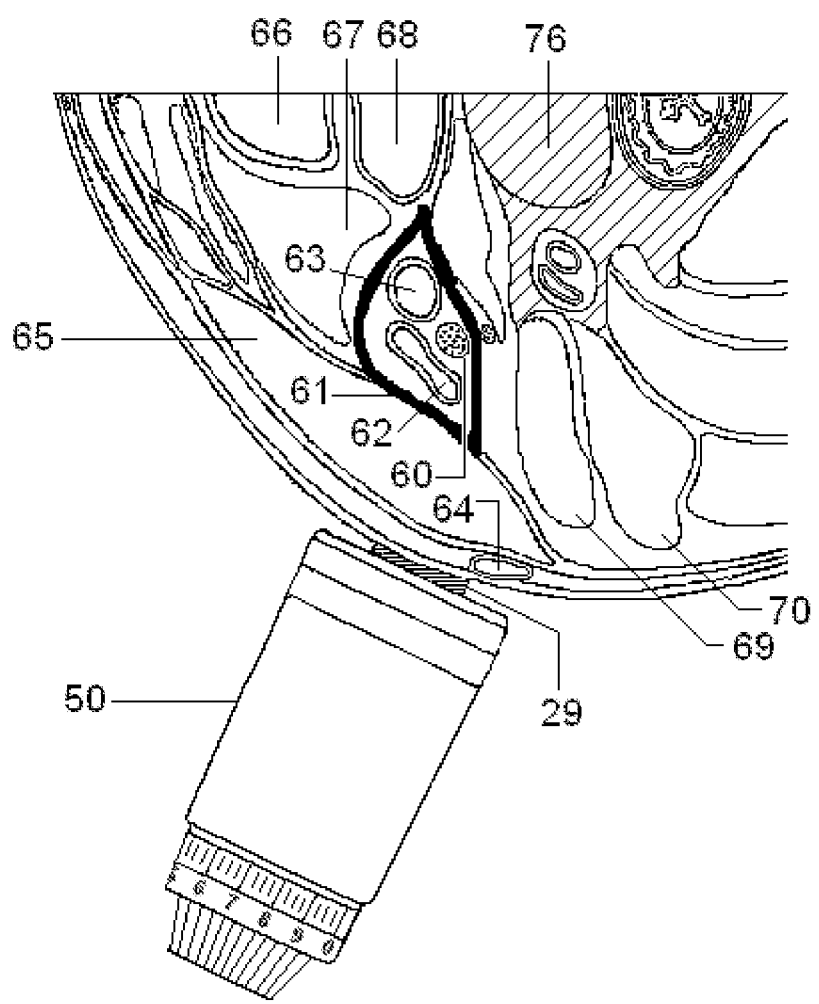
FIG. 7 illustrates the housing of the stimulator according one embodiment of the present invention, when positioned to stimulate a vagus nerve in the patient's neck, wherein the stimulator is applied to the surface of the neck in the vicinity of the identified anatomical structures.

FIG. 7 provides a more detailed view of use of the electrical stimulator, when positioned to stimulate the vagus nerve at the neck location that is indicated in FIG. 6. As shown, the stimulator 50 in FIG. 5 touches the neck indirectly, by making electrical contact through conducting gel 29 (or other conducting material) which may be is dispensed through mesh openings (identified as 51 in FIG. 5) of the stimulator or applied as an electrode gel or paste. The layer of conducting gel 29 in FIG. 7 is shown to connect the device to the patient's skin, but it is understood that the actual location of the gel layer(s) may be generally determined by the location of mesh 51 shown in FIG. 5. Furthermore, it is understood that for other embodiments of the invention, the conductive head of the device may not necessitate the use of additional conductive material being applied to the skin.

The vagus nerve 60 is identified in FIG. 7, along with the carotid sheath 61 that is identified there in bold peripheral outline. The carotid sheath encloses not only the vagus nerve, but also the internal jugular vein 62 and the common carotid artery 63. Features that may be identified near the surface of the neck include the external jugular vein 64 and the sternocleidomastoid muscle 65. Additional organs in the vicinity of the vagus nerve include the trachea 66, thyroid gland 67, esophagus 68, scalenus anterior muscle 69, and scalenus medius muscle 70. The sixth cervical vertebra 76 is also shown in FIG. 7, with bony structure indicated by hatching marks.

Methods of treating a patient comprise stimulating the vagus nerve as indicated in FIGS. 6 and 7, using the electrical stimulation devices that are disclosed herein. Stimulation may be performed on the left or right vagus nerve or on both of them simulataneously or alternately. The position and angular orientation of the device are adjusted about that location until the patient perceives stimulation when current is passed through the stimulator electrodes. The applied current is increased gradually, first to a level wherein the patient feels sensation from the stimulation. The power is then increased, but is set to a level that is less than one at which the patient first indicates any discomfort. Straps, harnesses, or frames are used to maintain the stimulator in position. The stimulator signal may have a frequency and other parameters that are selected to produce a therapeutic result in the patient. Stimulation parameters for each patient are adjusted on an individualized basis. Ordinarily, the amplitude of the stimulation signal is set to the maximum that is comfortable for the patient, and then the other stimulation parameters are adjusted.

The stimulation is then performed with a sinusoidal burst waveform like that shown in FIG. 2. The pattern of a burst followed by silent inter-burst period repeats itself with a period of T. For example, the sinusoidal period may be 200 microseconds; the number of pulses per burst may be N=5; and the whole pattern of burst followed by silent inter-burst period may have a period of T=40000 microseconds, which is comparable to 25 Hz stimulation. More generally, there may be 1 to 20 pulses per burst, preferably five pulses. Each pulse within a burst has a duration of 1 to 1000 microseconds (i.e., about 1 to 10 KHz), preferably 200 microseconds (about 5 KHz). A burst followed by a silent inter-burst interval repeats at 1 to 5000 bursts per second (bps), preferably at 5-50 bps, and even more preferably 10-25 bps stimulation (10-25 Hz). The preferred shape of each pulse is a full sinusoidal wave, although triangular or other shapes may be used as well. For some patients, the stimulation may be performed for 30 minutes, and the treatment is performed several times a week for 12 weeks or longer. For patients experiencing intermittent symptoms, the treatment may be performed only when the patient is symptomatic. However, it is understood that parameters of the stimulation protocol may be varied in response to heterogeneity in the pathophysiology of patients. Different stimulation parameters may also be selected as the course of the patient's disease changes.

In other embodiments of the invention, pairing of vagus nerve stimulation may be with a additional sensory stimulation. The paired sensory stimulation may be bright light, sound, tactile stimulation, or electrical stimulation of the tongue to simulate odor/taste, e.g., pulsating with the same frequency as the vagus nerve electrical stimulation. The rationale for paired sensory stimulation is the same as simultaneous, paired stimulation of both left and right vagus nerves, namely, that the pair of signals interacting with one another in the brain may result in the formation of larger and more coherent neural ensembles than the neural ensembles associated with the individual signals, thereby enhancing the therapeutic effect.

For example, the hypothalamus is well known to be responsive to the presence of bright light, so exposing the patient to bright light that is fluctuating with the same stimulation frequency as the vagus nerve (or a multiple of that frequency) may be performed in an attempt to enhance the role of the hypothalamus in producing the desired therapeutic effect. Such paired stimulation does not necessarily rely upon neuronal plasticity and is in that sense different from other reports of paired stimulation [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011):101-104; PORTER B A, Khodaparast N, Fayyaz T, Cheung R J, Ahmed S S, Vrana W A, Rennaker R L 2nd, Kilgard M P. Repeatedly pairing vagus nerve stimulation with a movement reorganizes primary motor cortex. Cereb Cortex 22(10, 2012):2365-2374].

Selection of stimulation parameters to preferentially stimulate particular regions of the brain may be done empirically, wherein a set of stimulation parameters are chosen, and the responsive region of the brain is measured using fMRI or a related imaging method [CHAE J H, Nahas Z, Lomarev M, Denslow S, Lorberbaum J P, Bohning D E, George M S. A review of functional neuroimaging studies of vagus nerve stimulation (VNS). J Psychiatr Res. 37(6, 2003):443-455; CONWAY C R, Sheline Y I, Chibnall J T, George M S, Fletcher J W, Mintun M A. Cerebral blood flow changes during vagus nerve stimulation for depression. Psychiatry Res. 146(2, 2006):179-84]. Thus, by performing the imaging with different sets of stimulation parameters, a database may be constructed, such that the inverse problem of selecting parameters to match a particular brain region may be solved by consulting the database.

Stimulation waveforms may also be constructed by superimposing or mixing the burst waveform shown in FIG. 2, in which each component of the mixture may have a different period T, effectively mixing different burst-per-second waveforms. The relative amplitude of each component of the mixture may be chosen to have a weight according to correlations in different bands in an EEG for a particular resting state network. Thus, MANTINI et al performed simultaneous fMRI and EEG measurements and found that each resting state network has a particular EEG signature [see FIG. 3 in: MANTINI D, Perrucci M G, Del Gratta C, Romani G L, Corbetta M. Electrophysiological signatures of resting state networks in the human brain. Proc Natl Acad Sci USA 104(32, 2007):13170-13175]. They reported relative correlations in each of the following bands, for each resting state network that was measured: delta (1-4 Hz), theta (4-8 Hz), alpha (8-13 Hz), beta (13-30 Hz), and gamma (30-50 Hz) rhythms. For recently-identified resting state networks, measurement of the corresponding signature EEG networks will have to be performed.

According to the present embodiment of the invention, multiple signals shown in FIG. 2 are constructed, with periods T that correspond to a location near the midpoint of each of the EEG bands (e.g., using the MINATI data, T equals approximately 0.4 sec, 0.1667 sec, 0.095 sec, 0.0465 sec, and 0.025 sec, respectively). A more comprehensive mixture could also be made by mixing more than one signal for each band. These signals are then mixed, with relative amplitudes corresponding to the weights measured for any particular resting state network, and the mixture is used to stimulate the vagus nerve of the patient. Phases between the mixed signals are adjusted to optimize the fMRI signal for the resting state network that is being stimulated, thereby producing entrainment with the resting state network. Stimulation of a network may activate or deactivate a network, depending on the detailed configuration of adrenergic receptors within the network and their roles in enhancing or depressing neural activity within the network, as well as subsequent network-to-network interactions. It is understood that variations of this method may be used when different combined fMRI-EEG procedures are employed and where the same resting state may have different EEG signatures, depending on the circumstances [WU C W, Gu H, Lu H, Stein E A, Chen J H, Yang Y. Frequency specificity of functional connectivity in brain networks. Neuroimage 42(3, 2008):1047-1055; LAUFS H. Endogenous brain oscillations and related networks detected by surface EEG-combined fMRI. Hum Brain Mapp 29(7, 2008):762-769; MUSSO F, Brinkmeyer J, Mobascher A, Warbrick T, Winterer G. Spontaneous brain activity and EEG microstates. A novel EEG/fMRI analysis approach to explore resting-state networks. Neuroimage 52(4, 2010):1149-1161; ESPOSITO F, Aragri A, Piccoli T, Tedeschi G, Goebel R, Di Salle F. Distributed analysis of simultaneous EEG-fMRI time-series: modeling and interpretation issues. Magn Reson Imaging 27(8, 2009):1120-1130; FREYER F, Becker R, Anami K, Curio G, Villringer A, Ritter P. Ultrahigh-frequency EEG during fMRI: pushing the limits of imaging-artifact correction. Neuroimage 48(1, 2009):94-108]. Once the network is entrained, one may also attempt to change the signature EEG pattern of a network, by slowly changing the frequency content of the stimulation & EEG pattern of the network to which the stimulator is initially entrained. An objective in this case would be to reduce the frequency content of the resting state signature EEG.

The individualized selection of parameters for the nerve stimulation protocol may based on trial and error in order to obtain a beneficial response without the sensation of skin pain or muscle twitches. Ordinarily, the amplitude of the stimulation signal is set to the maximum that is comfortable for the patient, and then the other stimulation parameters are adjusted. Alternatively, the selection of parameter values may involve tuning as understood in control theory, and as described below. It is understood that parameters may also be varied randomly in order to simulate normal physiological variability, thereby possibly inducing a beneficial response in the patient [Buchman T G. Nonlinear dynamics, complex systems, and the pathobiology of critical illness. Curr Opin Crit Care 10(5, 2004):378-82].

Use of Control Theory Methods to Improve Treatment of Individual Patients

The vagus nerve stimulation may employ methods of control theory (e.g., feedback) in an attempt to compensate for motion of the stimulator relative to the vagus nerve; to avoid potentially dangerous situations such as excessive heart rate; to train autonomic control circuits within the brain in such a way as to enhance respiratory sinus arrhythmia; and to maintain measured EEG bands (e.g., delta, theta, alpha, beta) within predetermined ranges, in attempt to preferentially activate particular resting state networks. Thus, with these methods, the parameters of the vagus nerve stimulation may be changed automatically, depending on physiological measurements that are made, in attempt to maintain the values of the physiological signals within predetermined ranges.

The effects of vagus nerve stimulation on surface EEG waveforms may be difficult to detect [Michael BEWERNITZ, Georges Ghacibeh, Onur Seref, Panos M. Pardalos, Chang-Chia Liu, and Basim Uthman. Quantification of the impact of vagus nerve stimulation parameters on electroencephalographic measures. AIP Conf. Proc. DATA MINING, SYSTEMS ANALYSIS AND OPTIMIZATION IN BIOMEDICINE; Nov. 5, 2007, Volume 953, pp. 206-219], but they may exist nevertheless [KOO B. EEG changes with vagus nerve stimulation. J Clin Neurophysiol. 18(5, 2001): 434-41; KUBA R, Guzaninova M, Brazdil M, Novak Z, Chrastina J, Rektor I. Effect of vagal nerve stimulation on interictal epileptiform discharges: a scalp EEG study. Epilepsia. 43(10, 2002):1181-8; RIZZO P, Beelke M, De Carli F, Canovaro P, Nobili L, Robert A, Formaro P, Tanganelli P, Regesta G, Ferrillo F. Modifications of sleep EEG induced by chronic vagus nerve stimulation in patients affected by refractory epilepsy. Clin Neurophysiol. 115(3, 2004):658-64].

When stimulating the vagus nerve, motion variability may often be attributable to the patient's breathing, which involves contraction and associated change in geometry of the sternocleidomastoid muscle that is situated close to the vagus nerve (identified as 65 in FIG. 7). Modulation of the stimulator amplitude to compensate for this variability may be accomplished by measuring the patient's respiratory phase, or more directly by measuring movement of the stimulator, then using controllers (e.g., PID controllers) that are known in the art of control theory, as now described.

FIG. 8 is a control theory representation of the disclosed vagus nerve stimulation methods. As shown there, the autistic child, or the relevant physiological component of the child, is considered to be the "System" that is to be controlled. The "System" (patient) receives input from the "Environment." For example, the environment would include ambient temperature, light, and sound. If the "System" is defined to be only a particular physiological component of the patient, the "Environment" may also be considered to include physiological systems of the patient that are not included in the "System". Thus, if some physiological component can influence the behavior of another physiological component of the patient, but not vice versa, the former component could be part of the environment and the latter could be part of the system. On the other hand, if it is intended to control the former component to influence the latter component, then both components should be considered part of the "System."

The System also receives input from the "Controller", which in this case may comprise the vagus nerve stimulation device, as well as electronic components that may be used to select or set parameters for the stimulation protocol (amplitude, frequency, pulse width, burst number, etc.) or alert the patient as to the need to use or adjust the stimulator (i.e., an alarm). For example, the controller may include the control unit 330 in FIG. 2. Feedback in the schema shown in FIG. 8 is possible because physiological measurements of the System are made using sensors. Thus, the values of variables of the system that could be measured define the system's state ("the System Output"). As a practical matter, only some of those measurements are actually made, and they represent the "Sensed Physiological Input" to the Controller.

The preferred sensors will include ones ordinarily used for ambulatory monitoring. For example, the sensors may comprise those used in conventional Holter and bedside monitoring applications, for monitoring heart rate and variability, ECG, respiration depth and rate, core temperature, hydration, blood pressure, brain function, oxygenation, skin impedance, and skin temperature. The sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. The ECG sensors should be adapted to the automatic extraction and analysis of particular features of the ECG, for example, indices of P-wave morphology, as well as heart rate variability indices of parasympathetic and sympathetic tone. Measurement of respiration using noninvasive inductive plethysmography, mercury in silastic strain gauges or impedance pneumography is particularly advised, in order to account for the effects of respiration on the heart. A noninvasive accelerometer may also be included among the ambulatory sensors, in order to identify motion artifacts. An event marker may also be included in order for the patient to mark relevant circumstances and sensations.

For brain monitoring, the sensors may comprise ambulatory EEG sensors [CASSON A, Yates D, Smith S, Duncan J, Rodriguez-Villegas E. Wearable electroencephalography. What is it, why is it needed, and what does it entail? IEEE Eng Med Biol Mag. 29(3, 2010):44-56] or optical topography systems for mapping prefrontal cortex activation [Atsumori H, Kiguchi M, Obata A, Sato H, Katura T, Funane T, Maki A. Development of wearable optical topography system for mapping the prefrontal cortex activation. Rev Sci Instrum. 2009 April; 80(4):043704]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010):195-212]. In the present application, the features would include EEG bands (e.g., delta, theta, alpha, beta).

Detection of the phase of respiration may be performed non-invasively by adhering a thermistor or thermocouple probe to the patient's cheek so as to position the probe at the nasal orifice. Strain gauge signals from belts strapped around the chest, as well as inductive plethysmography and impedance pneumography, are also used traditionally to non-invasively generate a signal that rises and falls as a function of the phase of respiration. Respiratory phase may also be inferred from movement of the sternocleidomastoid muscle that also causes movement of the vagus nerve stimulator during breathing, measured using accelerometers attached to the vagus nerve stimulator, as described below. After digitizing such signals, the phase of respiration may be determined using software such as "puka", which is part of PhysioToolkit, a large published library of open source software and user manuals that are used to process and display a wide range of physiological signals [GOLDBERGER A L, Amaral LAN, Glass L, Hausdorff J M, Ivanov PCh, Mark R G, Mietus J E, Moody G B, Peng C K, Stanley H E. PhysioBank, PhysioToolkit, and PhysioNet: Components of a New Research Resource for Complex Physiologic Signals. Circulation 101(23, 2000):e215-e220] available from PhysioNet, M.I.T. Room E25-505A, 77 Massachusetts Avenue, Cambridge, Mass. 02139]. In one embodiment of the present invention, the control unit 330 contains an analog-to-digital converter to receive such analog respiratory signals, and software for the analysis of the digitized respiratory waveform resides within the control unit 330. That software extracts turning points within the respiratory waveform, such as end-expiration and end-inspiration, and forecasts future turning-points, based upon the frequency with which waveforms from previous breaths match a partial waveform for the current breath. The control unit 330 then controls the impulse generator 310, for example, to stimulate the selected nerve only during a selected phase of respiration, such as all of inspiration or only the first second of inspiration, or only the expected middle half of inspiration.

It may be therapeutically advantageous to program the control unit 330 to control the impulse generator 310 in such a way as to temporally modulate stimulation by the magnetic stimulator coils or electrodes, depending on the phase of the patient's respiration. In patent application JP2008/081479A, entitled Vagus nerve stimulation system, to YOSHIHOTO, a system is also described for keeping the heart rate within safe limits. When the heart rate is too high, that system stimulates a patient's vagus nerve, and when the heart rate is too low, that system tries to achieve stabilization of the heart rate by stimulating the heart itself, rather than use different parameters to stimulate the vagus nerve. In that disclosure, vagal stimulation uses an electrode, which is described as either a surface electrode applied to the body surface or an electrode introduced to the vicinity of the vagus nerve via a hypodermic needle. That disclosure is unrelated to the neurodevelopmental problems that are addressed here, but it does consider stimulation during particular phases of the respiratory cycle, for the following reason. Because the vagus nerve is near the phrenic nerve, Yoshihoto indicates that the phrenic nerve will sometimes be electrically stimulated along with the vagus nerve. The present applicants have not experienced this problem, so the problem may be one of a misplaced electrode. In any case, the phrenic nerve controls muscular movement of the diaphragm, so consequently, stimulation of the phrenic nerve causes the patient to hiccup or experience irregular movement of the diaphragm, or otherwise experience discomfort. To minimize the effects of irregular diaphragm movement, Yoshihoto's system is designed to stimulate the phrenic nerve (and possibly co-stimulate the vagus nerve) only during the inspiration phase of the respiratory cycle and not during expiration. Furthermore, the system is designed to gradually increase and then decrease the magnitude of the electrical stimulation during inspiration (notably amplitude and stimulus rate) so as to make stimulation of the phrenic nerve and diaphragm gradual.

The present invention also discloses stimulation of the vagus nerve as a function of respiratory phase, but the timing, amplitude and rationale for the stimulation are all different from Yoshihoto's method. The present objective of varying the electrical nerve stimulation as a function of respiratory phase is to train the autonomic nervous system of the autistic child, in such a way as to enhance respiratory sinus arrhythmia (RSA). During the process of RSA, inhalation temporarily suppresses vagal activity, causing an immediate increase in heart rate. Exhalation then decreases heart rate and causes vagal activity to resume. The magnitude of RSA is readily measured by extracting heart rate from the ECG of the patient, decomposing the heart rate into its Fourier components, and measuring the peak or frequency range that is exaggerated by respiration [U. Rajendra ACHARYA, K. Paul Joseph, N. Kannathal, Choo Min Lim and Jasjit S. Suri. Heart rate variability: a review. Medical and Biological Engineering and Computing 44(12, 2006), 1031-1051; YASUMA F, Hayano J. Respiratory sinus arrhythmia: why does the heartbeat synchronize with respiratory rhythm? Chest 125(2, 2004):683-690; BERNTSON G G, Cacioppo J T, Quigley K S. Respiratory sinus arrhythmia: autonomic origins, physiological mechanisms, and psychophysiological implications. Psychophysiology 30(2, 1993):

183-196]. The RSA is an indication of vagal or parasympathetic tone. In contrast, sympathetic tone may be estimated from lower frequency components of the Fourier spectrum, or by measuring electrodermal activity [Wolfram BOUCSEIN. Electrodermal activity, 2nd Ed., New York: Springer, 2012, pp. 1-618].

Early in gestation, the fetal heart rate is predominately under the control of the sympathetic nervous system and arterial chemoreceptors. As the fetus develops, its heart rate decreases in response to parasympathetic (vagal) nervous system maturation. RSA then develops, which may be measured even in utero during fetal breathing episodes [DIVON M Y, Yeh S Y, Zimmer E Z, Platt L D, Paldi E, Paul R H. Respiratory sinus arrhythmia in the human fetus. Am J Obstet Gynecol 151(4, 1985):425-428]. Thereafter, RSA follows a maturational trajectory that parallels changes in both number and ratio of myelinated vagal fibers.

Children with autism do not follow the normal changing pattern of sympathetic/parasympathetic balance, and they have significantly reduced parasympathetic tone with autonomic dysfunction, as evidenced by their reduced RSA [BAL E, Harden E, Lamb D, Van Hecke A V, Denver J W, Porges S W. Emotion recognition in children with autism spectrum disorders: relations to eye gaze and autonomic state. J Autism Dev Disord 40(3, 2010):358-370; SCHAAF R C, Miller L J, Seawell D, O'Keefe S. Children with disturbances in sensory processing: a pilot study examining the role of the parasympathetic nervous system. Am J Occup Ther 57(4, 2003):442-449; X. MING, P. O. O. Julu, M. Brimacombe, S. Connor, and M. L. Daniels, Reduced cardiac parasympathetic activity in children with autism. Brain and Development 27(7, 2005):509-516]. The balance of excitatory and inhibitory activity within the sympathetic and parasympathetic divisions of the autonomic nervous system in autistic children may also be measured using pupil diameter as a surrogate [ANDERSON C J, Colombo J. Larger tonic pupil size in young children with autism spectrum disorder. Dev Psychobiol 51(2, 2009):207-211]. Compared with normal children, autistic children have an imbalance that favors sympathetic tone, and they apparently use self-stimulation activities in order to calm hyper-responsive activity of their sympatheic nervous system [W HIRSTEIN, P Iversen, and V S Ramachandran. Autonomic responses of autistic children to people and objects. Proc Royal Soc. Biol Sci. 268(1479, 2001): 1883-1888].

The present invention attempts to increase parasympathetic tone in autistic children, by increasing their RSA. It does so by training the child's autonomic nervous system to inhibit or suppress vagal activity during inhalation and increase vagal activity during exhalation. Thus, a blocking or inhibiting electrical signal is applied preferably to the right vagus nerve during inhalation (or not stimulated at all in one embodiment), but it is stimulated with an excitatory signal during exhalation. The signals may increase in amplitude gradually to a maximum at the midpoint of exhalation or inhalation, and then decrease, so as to simulate what the vagus nerve would be doing in normal RSA. Assuming that abnormal RSA has already been documented for the child in utero and shortly after birth, the intervention is preferably performed during the child's first and second years when the vagus nerve and autonomic nervous system are still rapidly developing and most susceptible to excitation/inhibition balancing by external influences [DORRNAL, Yuan K, Barker A J, Schreiner C E, Froemke R C. Developmental sensory experience balances cortical excitation and inhibition. Nature 465(7300, 2010):932-936]. Even if the intervention is not performed during the child's first two years, it may still be effective in increasing RSA owing to the plasticity of neural circuits, as illustrated by vagal nerve stimulation treatments for tinnitus and movement disorders [Navzer D. ENGINEER, Jonathan R. Riley, Jonathan D. Seale, Will A. Vrana, Jai A. Shetake, Sindhu P. Sudanagunta, Michael S. Borland and Michael P. Kilgard. Reversing pathological neural activity using targeted plasticity. Nature 470(7332, 2011):101-104; PORTER B A, Khodaparast N, Fayyaz T, Cheung R J, Ahmed S S, Vrana W A, Rennaker R L 2nd, Kilgard M P. Repeatedly pairing vagus nerve stimulation with a movement reorganizes primary motor cortex. Cereb Cortex 22(10, 2012):2365-2374]. The treatment may be performed for an extended period every day, and over the course of many weeks, the amplitudes of the stimulation may be reduced as the child's autonomic nervous system develops a more normal RSA.

In some embodiments of the invention, overheating of the magnetic stimulator coil may also be minimized by optionally restricting the magnetic stimulation to particular phases of the respiratory cycle, allowing the coil to cool during the other phases of the respiratory cycle. Alternatively, greater peak power may be achieved per respiratory cycle by concentrating all the energy of the magnetic pulses into selected phases of the respiratory cycle.

Furthermore, as an option in the present invention, parameters of the stimulation may be modulated by the control unit 330 to control the impulse generator 310 in such a way as to temporally modulate stimulation by the magnetic stimulator coil or electrodes, so as to achieve and maintain the heart rate within safe or desired limits. In that case, the parameters of the stimulation are individually raised or lowered in increments (power, frequency, etc.), and the effect as an increased, unchanged, or decreased heart rate is stored in the memory of the control unit 330. When the heart rate changes to a value outside the specified range, the control unit 330 automatically resets the parameters to values that had been recorded to produce a heart rate within that range, or if no heart rate within that range has yet been achieved, it increases or decreases parameter values in the direction that previously acquired data indicate would change the heart rate in the direction towards a heart rate in the desired range. Similarly, the arterial blood pressure is also recorded non-invasively in an embodiment of the invention, and as described above, the control unit 330 extracts the systolic, diastolic, and mean arterial blood pressure from the blood pressure waveform. The control unit 330 will then control the impulse generator 310 in such a way as to temporally modulate nerve stimulation by the magnetic stimulator coil or electrodes, in such a way as to achieve and maintain the blood pressure within predetermined safe or desired limits, by the same method that was indicated above for the heart rate. Thus, even if one does not intend to treat neurodevelpmental problems, embodiments of the invention described above may be used to achieve and maintain the heart rate and blood pressure within desired ranges.

Let the measured output variables of the system in FIG. 8 be denoted by $y_i$ (i=1 to Q); let the desired (reference or setpoint) values of $y_i$ be denoted by $r_i$ and let the controller's input to the system consist of variables $u_j$ (j=1 to P). The objective is for a controller to select the input $u_j$ in such a way that the output variables (or a subset of them) closely follows the reference signals $r_i$, i.e., the control error $e_i=r_i-y_i$ is small, even if there is environmental input or noise to the system. Consider the error function $e_i=r_i-y_i$ to be the sensed physiological input to the controller in FIG. 8 (i.e., the reference signals are integral to the controller, which subtracts the measured system values from them to construct the control error signal). The controller will also receive a set of measured environmental signals $v_k$ (k=1 to R), which also act upon the system as shown in FIG. 8.

The functional form of the system's input u(t) is constrained to be as shown in FIGS. 2D and 2E. Ordinarily, a parameter that needs adjusting is the one associated with the amplitude of the signal shown in FIG. 2. As a first example of the use of feedback to control the system, consider the problem of adjusting the input u(t) from the vagus nerve stimulator (i.e., output from the controller) in order to compensate for motion artifacts.

Nerve activation is generally a function of the second spatial derivative of the extracellular potential along the nerve's axon, which would be changing as the position of the stimulator varies relative to the axon [F. RATTAY. The basic mechanism for the electrical stimulation of the nervous system. Neuroscience 89 (2, 1999):335-346]. Such motion artifact can be due to movement by the patient (e.g., neck movement) or movement within the patient (e.g. sternocleidomastoid muscle contraction associated with respiration), or it can be due to movement of the stimulator relative to the body (slippage or drift). Thus, one expects that because of such undesired or unavoidable motion, there will usually be some error (e=r−y) in the intended (r) versus actual (y) nerve stimulation amplitude that needs continuous adjustment.

Accelerometers can be used to detect all these types of movement, using for example, Model LSM330DL from STMicroelectronics, 750 Canyon Dr #300 Coppell, Tex. 75019. One or more accelerometer is attached to the patient's neck, and one or more accelerometer is attached to the head of the stimulator in the vicinity of where the stimulator contacts the patient. Because the temporally integrated outputs of the accelerometers provide a measurement of the current position of each accelerometer, the combined accelerometer outputs make it possible to measure any movement of the stimulator relative to the underlying tissue.

The location of the vagus nerve underlying the stimulator may be determined preliminarily by placing an ultrasound probe at the location where the center of the stimulator will be placed [KNAPPERTZ V A, Tegeler C H, Hardin S J, McKinney W M. Vagus nerve imaging with ultrasound: anatomic and in vivo validation. Otolaryngol Head Neck Surg 118(1, 1998):82-5]. The ultrasound probe is configured to have the same shape as the stimulator, including the attachment of one or more accelerometer. As part of the preliminary protocol, the patient with accelerometers attached is then instructed or helped to perform neck movements, breathe deeply so as to contract the sternocleidomastoid muscle, and generally simulate possible motion that may accompany prolonged stimulation with the stimulator. This would include possible slippage or movement of the stimulator relative to an initial position on the patient's neck. While these movements are being performed, the accelerometers are acquiring position information, and the corresponding location of the vagus nerve is determined from the ultrasound image. With these preliminary data, it is then possible to infer the location of the vagus nerve relative to the stimulator, given only the accelerometer data during a stimulation session, by interpolating between the previously acquired vagus nerve position data as a function of accelerometer position data.

For any given position of the stimulator relative to the vagus nerve, it is also possible to infer the amplitude of the electric field that it produces in the vicinity of the vagus nerve. This is done by calculation or by measuring the electric field that is produced by the stimulator as a function of depth and position within a phantom that simulates the relevant bodily tissue [Francis Marion MOORE. Electrical Stimulation for pain suppression: mathematical and physical models. Thesis, School of Engineering, Cornell University, 2007; Bartosz SAWICKI, Robert Szmurlo, Przemyslaw Plonecki, Jacek Starzynski, Stanislaw Wincenciak, Andrzej Rysz. Mathematical Modelling of Vagus Nerve Stimulation. pp. 92-97 in: Krawczyk, A. Electromagnetic Field, Health and Environment: Proceedings of EHE'07. Amsterdam, IOS Press, 2008]. Thus, in order to compensate for movement, the controller may increase or decrease the amplitude of the output from the stimulator (u) in proportion to the inferred deviation of the amplitude of the electric field in the vicinity of the vagus nerve, relative to its desired value.

For present purposes, no distinction is made between a system output variable and a variable representing the state of the system. Then, a state-space representation, or model, of the system consists of a set of first order differential equations of the form $dy_i/dt = F_i(t, \{y_i\}, \{u_j\}, \{v_k\}; \{r_i\})$, where t is time and where in general, the rate of change of each variable $y_i$ is a function ($F_i$) of many other output variables as well as the input and environmental signals.

Classical control theory is concerned with situations in which the functional form of $F_i$ is as a linear combination of the state and input variables, but in which coefficients of the linear terms are not necessarily known in advance. In this linear case, the differential equations may be solved with linear transform (e.g., Laplace transform) methods, which convert the differential equations into algebraic equations for straightforward solution. Thus, for example, a single-input single-output system (dropping the subscripts on variables) may have input from a controller of the form:

$$u(t) = K_p e(t) + K_i \int_0^t e(\tau) d\tau + K_d \frac{de}{dt}$$

where the parameters for the controller are the proportional gain ($K_p$), the integral gain ($K_i$) and the derivative gain ($K_d$). This type of controller, which forms a controlling input signal with feedback using the error e=r−y, is known as a PID controller (proportional-integral-derivative).

Optimal selection of the parameters of the controller could be through calculation, if the coefficients of the corresponding state differential equation were known in advance. However, they are ordinarily not known, so selection of the controller parameters (tuning) is accomplished by experiments in which the error e either is or is not used to form the system input (respectively, closed loop or open loop experiments). In an open loop experiment, the input is increased in a step (or random binary sequence of steps), and the system response is measured. In a closed loop experiment, the integral and derivative gains are set to zero, the proportional gain is increased until the system starts to oscillate, and the period of oscillation is measured. Depending on whether the experiment is open or closed loop, the selection of PID parameter values may then be selected according to rules that were described initially by Ziegler and Nichols. There are also many improved versions of tuning rules, including some that can be implemented automatically by the controller [LI, Y., Ang, K. H. and Chong, G. C. Y. Patents, software and hardware for PID control: an overview and analysis of the current art. IEEE Control Systems Magazine, 26 (1, 2006): 42-54; Karl Johan Åström & Richard M. Murray. Feedback Systems: An Introduction for Scientists and Engineers. Princeton N.J.: Princeton University Press, 2008; Finn HAUGEN. Tuning of PID controllers (Chapter 10) In: Basic Dynamics and Control. 2009. ISBN 978-82-91748-13-9. TechTeach, Enggravhøgda 45, N-3711 Skien, Norway. http://techteach.no., pp. 129-155; Dingyu XUE, YangQuan Chen, Derek P. Atherton. PID controller design (Chapter 6), In: Linear Feedback Control: Analysis and Design with MATLAB. Society for Industrial and Applied Mathematics (SIAM). 3600 Market Street, 6th Floor, Philadelphia, Pa. (2007), pp. 183-235; Jan JANTZEN, Tuning Of Fuzzy PID Controllers, Technical University of Denmark, report 98-H 871, Sep. 30, 1998].

Commercial versions of PID controllers are available, and they are used in 90% of all control applications. To use such a controller, for example, in an attempt to maintain the EEG gamma band at a particular level relative to the alpha band, one could set the integral and derivative gains to zero, increase the proportional gain (amplitude of the stimulation) until the relative gamma band level starts to oscillate, and then measure the period of oscillation. The PID would then be set to its tuned parameter values.

Although classical control theory works well for linear systems having one or only a few system variables, special methods have been developed for systems in which the system is nonlinear (i.e., the state-space representation contains nonlinear differential equations), or multiple input/output variables. Such methods are important for the present invention because the physiological system to be controlled will be generally nonlinear, and there will generally be multiple output physiological signals. It is understood that those methods may also be implemented in the controller shown in FIG. 8 [Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005].

The controller shown in FIG. 8 may also make use of feed-forward methods [Coleman BROSILOW, Babu Joseph. Feedforward Control (Chapter 9) In: Techniques of Model-Based Control. Upper Saddle River, N.J.: Prentice Hall PTR, 2002. pp, 221-240]. Thus, the controller in FIG. 8 may be a type of predictive controller, methods for which have been developed in other contexts as well, such as when a model of the system is used to calculate future outputs of the system, with the objective of choosing among possible inputs so as to optimize a criterion that is based on future values of the system's output variables.

Performance of system control can be improved by combining the feedback closed-loop control of a PID controller with feed-forward control, wherein knowledge about the system's future behavior can be fed forward and combined with the PID output to improve the overall system performance. For example, if the sensed environmental input in FIG. 8 is such the environmental input to the system will have a deleterious effect on the system after a delay, the controller may use this information to provide anticipatory control input to the system, so as to avert or mitigate the deleterious effects that would have been sensed only after-the-fact with a feedback-only controller.

A mathematical model of the system is needed in order to perform the predictions of system behavior, e.g., make predictions concerning the child's future respiratory state. For example, if the vagus nerve stimulation is intended to increase only until the middle of inspiration or expiration, one would ordinarily know only after-the-fact whether the midpoint has actually been reached. Models that are completely based upon physical first principles (white-box) are rare, especially in the case of physiological systems. Instead, most models that make use of prior structural and mechanistic understanding of the system are so-called grey-box models. If the mechanisms of the systems are not sufficiently understood in order to construct a white or grey box model, a black-box model may be used instead. One example for the problem of predicting respiratory phase is described by CAMINAL and colleagues [CAMINAL P, Domingo L, Giraldo B F, Vallverdú M, Benito S, Vázquez G, Kaplan D. Variability analysis of the respiratory volume based on non-linear prediction methods. Med Biol Eng Comput 42(1, 2004):86-91]. Such black box models comprise autoregressive models [Tim BOLLERSLEV. Generalized autoregressive condiditional heteroskedasticity. Journal of Econometrics 31 (1986):307-327], or those that make use of principal components [James H. STOCK, Mark W. Watson. Forecasting with Many Predictors, In: Handbook of Economic Forecasting. Volume 1, G. Elliott, C. W. J. Granger and A. Timmermann, eds (2006) Amsterdam: Elsevier B.V, pp 515-554], Kalman filters [Eric A. WAN and Rudolph van der Merwe. The unscented Kalman filter for nonlinear estimation, In: Proceedings of Symposium 2000 on Adaptive Systems for Signal Processing, Communication and Control (AS-SPCC), IEEE, Lake Louise, Alberta, Canada, October, 2000, pp 153-158], wavelet transforms [O. RENAUD, J.-L. Stark, F. Murtagh. Wavelet-based forecasting of short and long memory time series. Signal Processing 48(1996):51-65], hidden Markov models [Sam ROWEIS and Zoubin Ghahramani. A Unifying Review of Linear Gaussian Models. Neural Computation 11(2, 1999): 305-345], or artificial neural networks [Guoquiang ZHANG, B. Eddy Patuwo, Michael Y. Hu. Forecasting with artificial neural networks: the state of the art. International Journal of Forecasting 14(1998): 35-62].

For the present invention, if a black-box model must be used, the preferred model will be one that makes use of support vector machines. A support vector machine (SVM) is an algorithmic approach to the problem of classification within the larger context of supervised learning. A number of classification problems whose solutions in the past have been solved by multi-layer back-propagation neural networks, or more complicated methods, have been found to be more easily solvable by SVMs [Christopher J. C. BURGES. A tutorial on support vector machines for pattern recognition. Data Mining and Knowledge Discovery 2(1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4(2, 2009): 24-38; PRESS, W H; Teukolsky, S A; Vetterling, W T; Flannery, B P (2007). Section 16.5. Support Vector Machines. In: Numerical Recipes: The Art of Scientific Computing (3rd ed.). New York: Cambridge University Press].

As a final example, consider the problem of predicting and preventing repetitive behavior on the part of an autistic child, particularly motor stereotypies (e.g., hand flapping, or rocking and swinging). As noted above, PORGES suggests that such behaviors in autistic individuals may reflect a naturally occurring biobehavioral strategy to stimulate and regulate a vagal system that is not functioning efficiently. If that is true, it may be possible to predict the imminence of such behavior from measurement of physiological variables of the child and avert the behavior by altering physiological variables of the child. The example assumes that vagus nerve stimulation can be applied as described above in connection with enhancing RSA, but the stimulation is applied only when the invention's feedforward system predicts that such repetitive behavior is imminent.

A training set of physiological data will have been acquired that includes whether or not the child is exhibiting the repetitive behavior. Thus, the classification of the child's state is whether or not the behavior is present, and the data used to make the classification consist of acquired physiological data. In general the more physiological data that are acquired, the better the forecast will be. At a minimum, the physiological variables should include heart rate (electrocardiogram leads), respiration (e.g., abdominal and thoracic plethysmography), and motion (accelerometer). Preferably it would also include skin impedance (electrodermal leads), carbon dioxide (capnometry with nasual cannula), vocalization (microphones), light (light sensor), external and finger temperature (thermometers), EEG and its derived features; etc., as well as parameters of the stimulator device, all evaluated at Δ time units prior to the time at which binary "repetitive behavior present" (yes/no) data are acquired, as indicated by a caregiver. Thus, for a child who is experiencing repetitive behavior, the SVM is trained to forecast the termination of the behavior, Δ time units into the future, and the training set includes the time-course of features extracted from the above-mentioned physiological signals. For a child who is not experiencing repetitive behavior, the SVM is trained to forecast the imminence of repetitive behavior, Δ time units into the future, and the training set includes the above-mentioned physiological signals. After training the SVM, it is implemented as part of the controller. For children who are not experiencing symptoms, the controller may apply the RSA vagal nerve stimulation as a prophylactic whenever there is a forecast of imminent repetitive behavior. The controller will also turn off the RSA vagal nerve stimulation when it forecasts or detects the termination of the repetitive behavior.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating a behavioral disorder in a patient diagnosed therewith, the method comprising:
positioning a contact surface of a housing in contact with an outer skin surface of a neck of the patient, wherein the housing houses a power source, an electrode, and a conductor, wherein the conductor is coupled to the power source and the electrode, and wherein the electrode is coupled to the contact surface;
generating an electric current with the power source; and
transmitting the electric current transcutaneously, as the contact surface is in contact with the outer skin surface of the neck of the patient, through the outer skin surface of the neck of the patient, from the power source through the conductor, the electrode, and the contact surface to a vagus nerve in the patient non-invasively, to generate an electrical impulse at the vagus nerve, wherein the electrical impulse comprises a frequency that modifies the behavioral disorder within the patient.

2. The method of claim 1, wherein the conductor is a first conductor, wherein the transmitting comprises transmitting the electric current from the electrode, and wherein the transmitting is from the electrode through a second conductor housed within the housing.

3. The method of claim 1, further comprising:
generating an electric field at or near the housing; and
shaping the electric field such that the electric field is sufficient to modulate the vagus nerve; and
wherein the electric field is not sufficient to substantially modulate a nerve or muscle between the outer skin surface and a target region.

4. The method of claim 1, wherein the housing comprises a signal generator coupled to the electrode.

5. The method of claim 3, wherein the electric field at the vagus nerve is from about 10 V/m to about 600 V/m.

6. The method of claim 5, wherein the electric field is less than 100 V/m.

7. The method of claim 1, wherein the electrical impulse comprises bursts of pulses with a frequency from about 1 burst per second to about 100 bursts per second.

8. The method of claim 7, wherein each of the bursts contains from 1 pulse to 20 pulses.

9. The method of claim 7 wherein the pulses are full sinusoidal waves.

10. The method of claim 7, wherein each of the pulses is from about 100 microseconds to about 1000 microseconds in duration.

11. The method of claim 10, wherein the duration of a pulse of the pulses within a burst of the bursts is about 200 microseconds, wherein a number of pulses per burst is from 4 to 6, and wherein a number of bursts per second is from 20 to 30.

12. The method of claim 1 further comprising:
generating an electric field at the vagus nerve above a threshold for generating an action potential within an A fiber or a B fiber of the vagus nerve and below a threshold for generating an action potential within a C fiber of the vagus nerve.

13. The method of claim 1 further comprising:
generating an electric field at the vagus nerve above a threshold for generating an action potential within a fiber of the vagus nerve responsible for activating a neural pathway causing a release of an inhibitory neurotransmitter within a brain of the patient.

14. The method of claim 1, wherein the frequency is from about 10 Hz to about 100 Hz.

15. The method of claim 1, wherein the electric current is transmitted transcutaneously for a daily time period of less than 24 hours.

16. The method of claim 1, wherein the housing includes a portion that is insulative, wherein the portion extends about the contact surface.

17. The method of claim 1, wherein the contact surface includes a dielectric material.

18. A method comprising:
positioning a contact surface of a housing in contact with an outer skin surface of a neck of the patient, wherein the housing houses a power source, an electrode, and a conductor, wherein the conductor is coupled to the power source and the electrode, and wherein the electrode is coupled to the contact surface;
generating an electric current with the power source; and
transmitting the electric current transcutaneously, as the contact surface is in contact with the outer skin surface of the neck of the patient, through the outer skin surface of the neck of the patient, from the power source through the conductor, the electrode, and the contact surface to a vagus nerve in the patient non-invasively, to generate an electrical impulse at the vagus nerve, wherein the electrical impulse comprises a frequency that modifies a neurodegenerative disorder of the patient.

\* \* \* \* \*